US008865643B2

(12) United States Patent
Clark et al.

(10) Patent No.: US 8,865,643 B2
(45) Date of Patent: Oct. 21, 2014

(54) RECOMBINANT SURFACTANT PROTEIN D COMPOSITIONS AND METHODS OF USE THEREOF

(75) Inventors: Howard Clark, Southampton (GB); Palaniyar Nadesalingam, Toronto (CA); Kenneth B. Reid, Oxford (GB); Peter Strong, Oxford (GB)

(73) Assignee: Medical Research Council, Swindon (GB)

( * ) Notice: Subject to any disclaimer, the term of this patent is extended or adjusted under 35 U.S.C. 154(b) by 234 days.

(21) Appl. No.: 13/020,607

(22) Filed: Feb. 3, 2011

(65) Prior Publication Data

US 2012/0010126 A1    Jan. 12, 2012

Related U.S. Application Data

(60) Division of application No. 10/830,959, filed on Apr. 23, 2004, now abandoned, which is a continuation-in-part of application No. PCT/GB02/04824, filed on Oct. 25, 2002.

(30) Foreign Application Priority Data

Oct. 25, 2001  (GB) .................................. 0125638.7
Apr. 26, 2002  (GB) .................................. 0209619.6

(51) Int. Cl.
*A61K 38/17* (2006.01)
*A61P 11/00* (2006.01)
*C07K 14/785* (2006.01)

(52) U.S. Cl.
CPC ..................................... *C07K 14/785* (2013.01)
USPC ............................. 514/1.5; 514/1.8; 514/15.5

(58) Field of Classification Search
None
See application file for complete search history.

(56) References Cited

U.S. PATENT DOCUMENTS

| 5,242,810 A | 9/1993 | Maraganore et al. |
| 5,273,896 A | 12/1993 | Pedersen et al. |
| 2003/0221199 A1* | 11/2003 | Whitsett ........................... 800/3 |

FOREIGN PATENT DOCUMENTS

| EP | 1108786 A1 | 6/2001 |
| WO | WO-95/31540 A1 | 11/1995 |
| WO | WO-00/23569 A1 | 4/2000 |
| WO | WO-0206301 A2 | 1/2002 |

OTHER PUBLICATIONS

Bruscia et al., "Macrophages directly contribute to the exaggerated inflammatory response in cystic fibrosis transmembrane conductance regulator -/- mice." *American Journal of Respiratory Cell and Molecular Biology*, 2009, vol. 40, p. 295-304.

Cai et al., "Recombinant SP-D carbohydrate recognition domain is a chemoattractant for human neutrophilis," *American Journal of Physiology*, 1999, vol. 276, No. part 1., p. L131-136.

Clark et al., "Surfactant protein D reduces alveolar macrophage apoptosis in vivo," *Journal of Immunology*, 2002, vol. 169, No. 6, p. 2892-2899.

The International Search Report (PCT/GB02/04824), dated Jul. 31, 2003.

Crouch et al., "Accumulation of Surfactant Protein D in Human Pulmonary Alveolar Proteinosis," *Amer. Journal of Pathology*, 1993, 142(1):241-248.

Crouch et al., "Genomic organization of human surfactant protein D (SP-D): SP-D is encoded on chromosome 10q22.2-23.1," *Journal of Biological Chemistry*, 1993, vol. 268, No. 4, p. 2976-2983.

Wang et al., "A recombinant polypeptide, composed of the alpha-helical neck region and the carbohydrate recognition domain of conglutinin, self-associates to give a functionally intact homotrimer," *FEBS Letters*, 1995, vol. 376, No. 1-2, p. 6-10.

Wang et al., "Inhibitory effect of pulmonary surfactant proteins A and D on allergen-induced lymphocyte proliferation and histamine release in children with asthma," *American Journal of Respiratory and Critical Care Medicine*, 1998, vol. 158, No. 2, p. 510-518.

Wang et al., "Interaction of human lung surfactant proteins A and D with mite (*Dermatophagoides pteronyssinus*) allergens," *Clin Exp. Immunol.*, vol. 106, 1996, pp. 367-373 (Abstract).

Yu et al., "Dermatophagoides-farinae-Induced Pulmonary Eosinophilic Inflammation in Mice," *Int. Arch. Allergy Immunol.*, 1997, 112:73-82.

Yu et al., "Early-Type Hypersensitivity-Associated Airway Inflammation and Eosinophilia Induced by *Dermatophagoides farinae* in Sensitized Mice," *Journal of Immunology*, 1996, 146:1923-1930.

Eda et al., "Structure of a truncated human surfactant protein D is less effective in agglutinating bacteria than the native structure and fails to inhibit haemagglutination by influenza A virus,", *Biochemical Journal*, 1997, vol. 323, No. 2, p. 393-399.

Eggleton et al., "Lung surfactant proteins involved in innate immunity," *Current Opinion in Immunology*, 1999, vol. 11., No. 1. p. 28-33.

Hakansson, et al., "Collectin structure: A review," *Protein Science*, 2000, vol. 9, pp. 1607-1617.

Hartshorn et al., "Enhanced anti-influenza activity of a surfactant protein D and serum conglutinin fusion protein," *American Journal of Physiology*, 2000, vol. 278, No. 1, part 1, p. L90-L98.

(Continued)

*Primary Examiner* — Lisa J Hobbs
(74) *Attorney, Agent, or Firm* — Marshall, Gerstein & Borun LLP

(57) ABSTRACT

We describe an rspd(n/CRD) polypeptide, fragment, homologue, variant or derivative thereof for use in a method of treatment or prophylaxis of a disease. A method of treating an individual suffering from a disease or preventing the occurrence of a disease in an individual is also described, in which the method comprises administering to the individual a therapeutically or prophylactically effective amount of an rspd (n/CRD) polypeptide, fragment, homologue, variant or derivative thereof. Preferably, the rspd (n/CRD) polypeptide and nucleic acid comprise SEQ ID NO: 1 and SEQ ID NO: 2, respectively.

3 Claims, 32 Drawing Sheets

(56) References Cited

OTHER PUBLICATIONS

Hodge et al., "Alveolar macrophages from subjects with chronic obstructive pulmonary disease are deficient in their ability to phaogcytose apoptotic airway epithelial cells." *Immunology and Cell Biology*, 2003, vol. 81, p. 289-296.

Hoppe et al., "A parallel three stranded a-helical bundle at the nucleation site of collagen triple-helix formation," *FEBS Letters*, 1994, 344:191-195.

Kishore et al, "The alpha-helical neck region of human lung surfactant protein D is essential for the binding of the carbohydrate recognition domains to lipopolysaccharides and phospholipids,"*Biochemical Journal*, 1996, vol. 318, No. 2, p. 505-511.

Levine et al., "Pulmonary collectins and innate host defense of the lung," *Microbes and Infection*, 2001, 3:161-166.

Lu et al., "Purification characterization and CDNA cloning of human lung surfactant protein D", *Biochemical Journal*, 1992, vol. 284, No. 3, p. 795-802.

Madan et al., "Surfactant proteins A and D protect mice against pulmonary hypersensitivity induced by *Aspergillus fumigatus* antigens and allergens." *J Clin Invest*. 2001, 107(4):467-75.

Postle et al. "Deficient hydrophilic lung surfactant proteins A and D with normal surfactant phospholipid molecular species in cystic fibrosis,", *American Journal of Respiratory Cell and Molecular Biology*, 1999, vol. 20, No. 1, p. 90-98.

Reid, "Interactions of surfactant protein D with pathogens, allergens and phagocytes," *Biochimica et Biophysica Acta*, 1998, vol. 1408, No. 2-3, p. 290-295.

Rust et al., "Human Surfactant Protein D: SP-D Contains a C-Type Lectin Carbohydrate Recognition Domain," *Archives of Biochemistry and Biophysics*, 1991, 290(1):116-126.

SwissProt accession No. P35247 PSPD_HUMAN, Feb. 1994.

* cited by examiner

FIGURE 6A
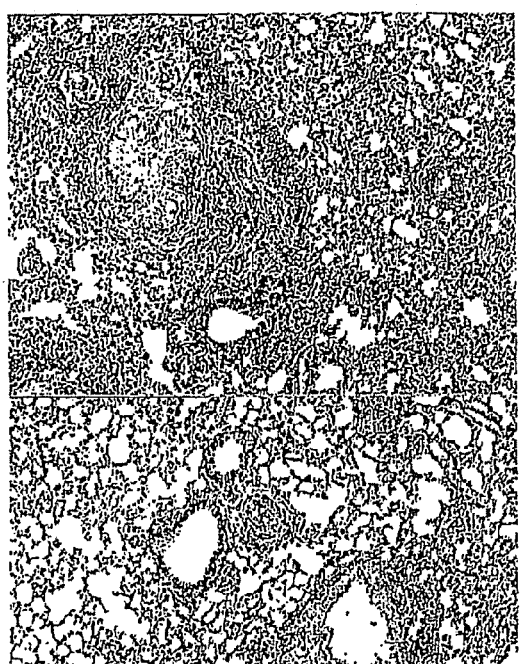
FIGURE 6B
FIGURE 6C
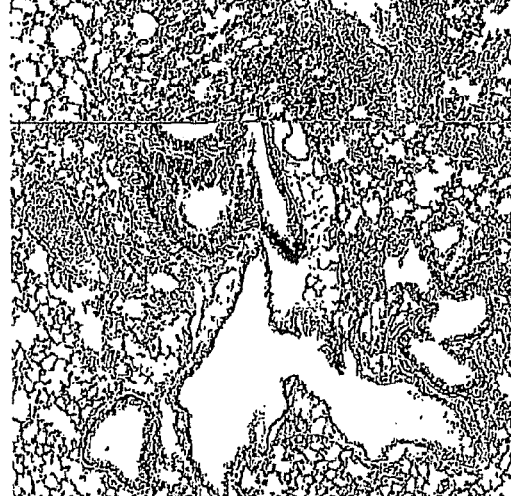

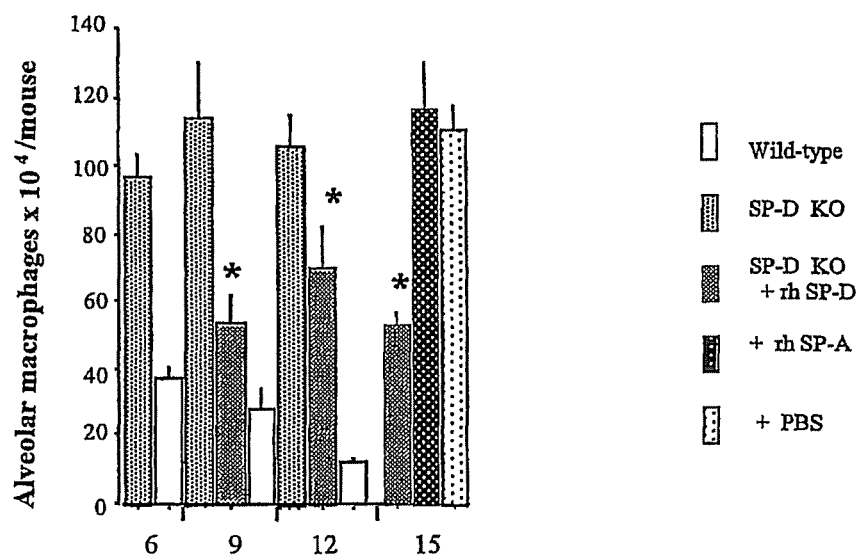

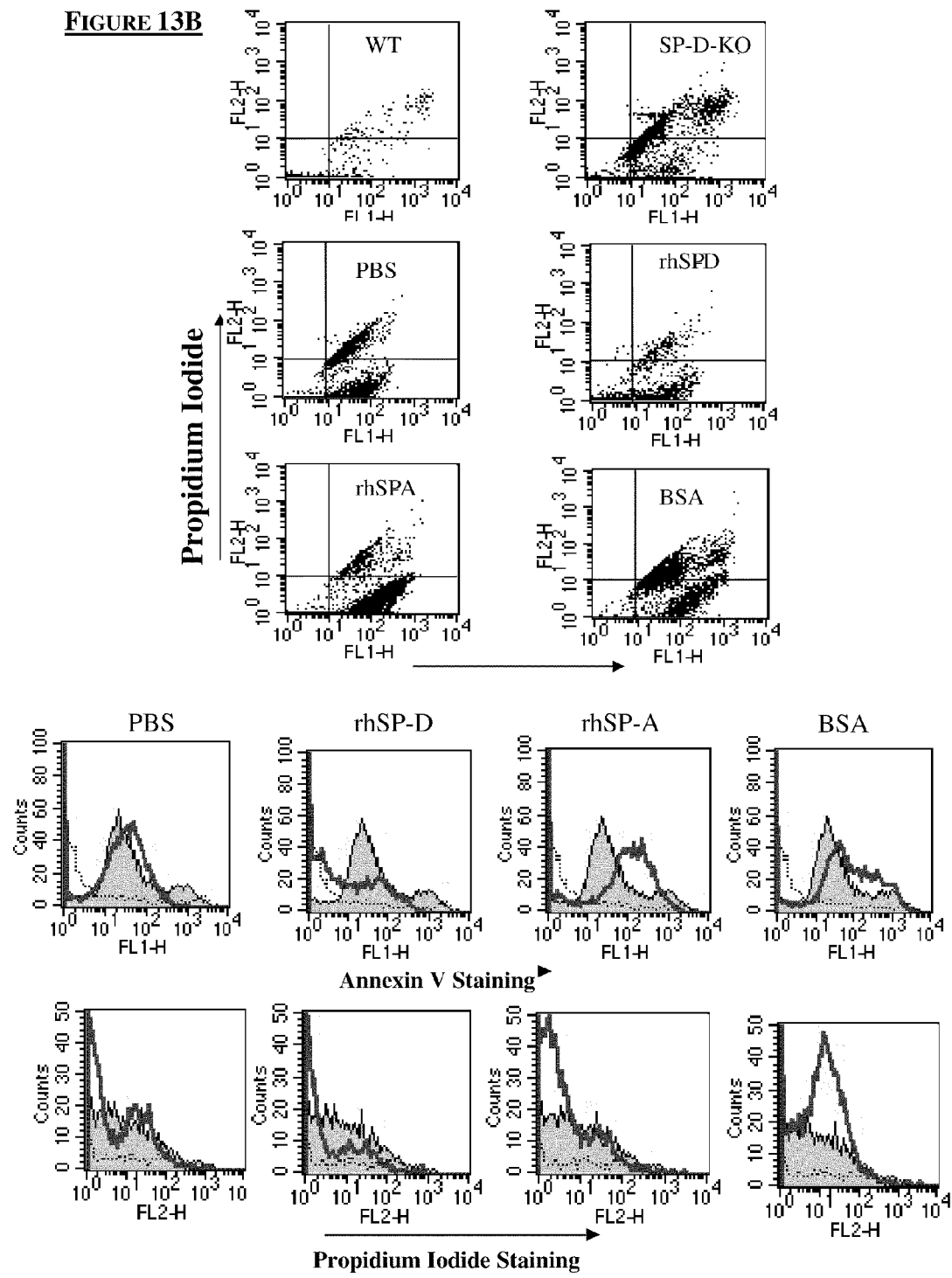

FIGURE 16A
Orange staining
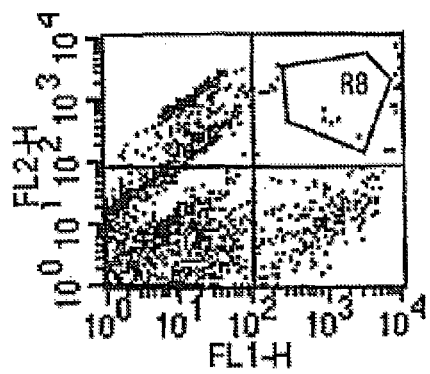 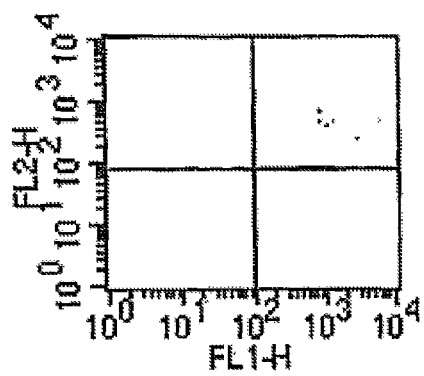
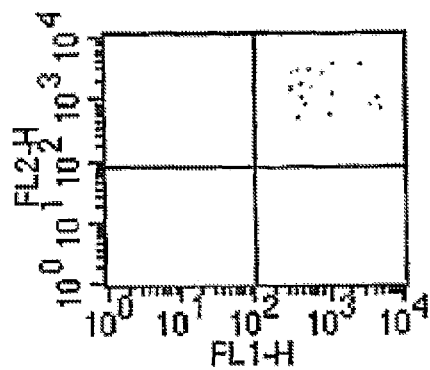 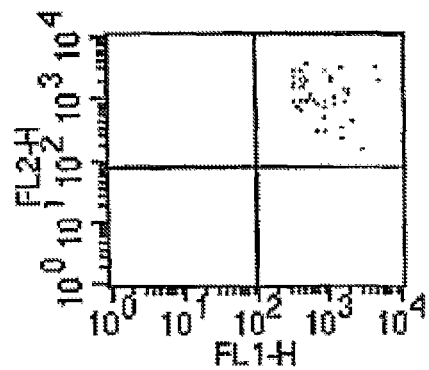
Green staining

SEQUENCE LISTING

```
<160> NUMBER OF SEQ ID NOS: 8

<210> SEQ ID NO 1
<211> LENGTH: 177
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Serine residue 2 differs from the Homo sapiens
      sequence, in which this residue is Proline.

<400> SEQUENCE: 1

Gly Ser Pro Gly Leu Lys Gly Asp Lys Gly Ile Pro Gly Asp Lys Gly
1               5                   10                  15

Ala Lys Gly Glu Ser Gly Leu Pro Asp Val Ala Ser Leu Arg Gln Gln
            20                  25                  30

Val Glu Ala Leu Gln Gly Gln Val Gln His Leu Gln Ala Ala Phe Ser
```

```
                35                  40                  45
Gln Tyr Lys Lys Val Glu Leu Phe Pro Asn Gly Gln Ser Val Gly Glu
     50                  55                  60

Lys Ile Phe Lys Thr Ala Gly Phe Val Lys Pro Phe Thr Glu Ala Gln
 65                  70                  75                  80

Leu Leu Cys Thr Gln Ala Gly Gly Gln Leu Ala Ser Pro Arg Ser Ala
                 85                  90                  95

Ala Glu Asn Ala Ala Leu Gln Gln Leu Val Val Ala Lys Asn Glu Ala
                100                 105                 110

Ala Phe Leu Ser Met Thr Asp Ser Lys Thr Glu Gly Lys Phe Thr Tyr
            115                 120                 125

Pro Thr Gly Glu Ser Leu Val Tyr Ser Asn Trp Ala Pro Gly Glu Pro
        130                 135                 140

Asn Asp Asp Gly Gly Ser Glu Asp Cys Val Glu Ile Phe Thr Asn Gly
145                 150                 155                 160

Lys Trp Asn Asp Arg Ala Cys Gly Glu Lys Arg Leu Val Val Cys Glu
                165                 170                 175

Phe

<210> SEQ ID NO 2
<211> LENGTH: 534
<212> TYPE: DNA
<213> ORGANISM: Homo sapiens

<400> SEQUENCE: 2
ggaagcccgg gattgaaggg ggacaaaggc attcctggag acaaaggagc aaagggagaa       60
agtgggcttc cagatgttgc ttctctgagg cagcaggttg aggccttaca gggacaagta      120
cagcaccctc caggctgctt tctctcagta taagaaagtt gagctcttcc caaatggcca      180
agtgtggggg agaagatttt caagacagca ggctttgtaa aaccatttac ggaggcacag      240
ctgctgtgca cacaggctgg tggacagttg gcctctccac gctctgccgc tgagaatgcc      300
gccttgcaac agctggtcgt agctaagaac gaggctgctt tcctgagcat gactgattcc      360
aagacagagg gcaagttcac ctaccccaca ggagagtccc tggtctattc caactgggcc      420
ccaggggagc ccaacgatga tggcgggtca gaggactgtg tggagatctt caccaatggc      480
aagtggaatg acagggcttg tggagaaaag cgtcttgtgg tctgcgagtt ctga           534

<210> SEQ ID NO 3
<211> LENGTH: 1128
<212> TYPE: DNA
<213> ORGANISM: Homo sapiens

<400> SEQUENCE: 3
atgctgctct tcctcctctc tgcactggtc ctgctcacac agccctggg ctacctggaa        60 gcagaaatga gacctactc ccacagaaca atgcccagtg cttgcaccct ggtcatgtgt       120
agctcagtgg agagtggcct gcctggtcgc gatggacggg atgggagaga gggccctcgg      180
ggcgagaagg gggacccagg tttgccagga gctgcagggc aagcagggat gcctggacaa      240
gctggcccag ttgggccaaa agggacaat ggctctgttg gagaacctgg accaagggga      300
gacactgggc caagtggacc tccaggacct cccggtgtgc ctggtccagc tgaagagaa      360 ggtgccctgg ggaagcaggg gaacatagga cctcagggca agccaggccc aaaaggagaa      420
gctgggccta aaggagaagt aggtgcccca ggcatgcagg gctcggcagg gcaagaggc      480 ctcgcaggcc ctaagggaga gcgaggtgtc cctggtgagc gtggagtccc tggaaacaca      540
```

-continued

```
ggggcagcag ggtctgctgg agccatgggt ccccagggaa gtccaggtgc caggggaccc      600
ccgggattga aggggacaa aggcattcct ggagacaaag gagcaaaggg agaaagtggg       660
cttccagatg ttgcttctct gaggcagcag gttgaggcct acagggaca agtacagcac      720 ctccaggctg ctttctctca gtataagaaa gttgagctct tcccaaatgg ccaaagtgtg     780
ggggagaaga ttttcaagac agcaggcttt gtaaaaccat ttacggaggc acagctgctg    840
tgcacacagg ctggtggaca gttggcctct ccacgctctg ccgctgagaa tgccgccttg   900
caacagctgg tcgtagctaa gaacgaggct gctttcctga gcatgactga ttccaagaca   960
gagggcaagt tcacctaccc cacaggagag tccctggtct attccaactg ggccccaggg  1020
gagcccaacg atgatggcgg gtcagaggac tgtgtggaga tcttcaccaa tggcaagtgg  1080
aatgacaggg cttgtggaga aaagcgtctt gtggtctgcg agttctga               1128
```

<210> SEQ ID NO 4
<211> LENGTH: 375
<212> TYPE: PRT
<213> ORGANISM: Homo sapiens

<400> SEQUENCE: 4

```
Met Leu Leu Phe Leu Leu Ser Ala Leu Val Leu Leu Thr Gln Pro Leu
1               5                  10                  15

Gly Tyr Leu Glu Ala Glu Met Lys Thr Tyr Ser His Arg Thr Met Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Ala Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Thr Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205

Ile Pro Gly Asp Lys Gly Ala Lys Gly Glu Ser Gly Leu Pro Asp Val
    210                 215                 220

Ala Ser Leu Arg Gln Gln Val Glu Ala Leu Gln Gly Gln Val Gln His
225                 230                 235                 240

Leu Gln Ala Ala Phe Ser Gln Tyr Lys Lys Val Glu Leu Phe Pro Asn
                245                 250                 255

Gly Gln Ser Val Gly Glu Lys Ile Phe Lys Thr Ala Gly Phe Val Lys
            260                 265                 270
```

```
Pro Phe Thr Glu Ala Gln Leu Leu Cys Thr Gln Ala Gly Gly Gln Leu
        275                 280                 285

Ala Ser Pro Arg Ser Ala Ala Glu Asn Ala Ala Leu Gln Gln Leu Val
290                 295                 300

Val Ala Lys Asn Glu Ala Ala Phe Leu Ser Met Thr Asp Ser Lys Thr
305                 310                 315                 320

Glu Gly Lys Phe Thr Tyr Pro Thr Gly Glu Ser Leu Val Tyr Ser Asn
                325                 330                 335

Trp Ala Pro Gly Glu Pro Asn Asp Asp Gly Ser Glu Asp Cys Val
                340                 345                 350

Glu Ile Phe Thr Asn Gly Lys Trp Asn Asp Arg Ala Cys Gly Glu Lys
                355                 360                 365

Arg Leu Val Val Cys Glu Phe
        370                 375

<210> SEQ ID NO 5
<211> LENGTH: 125
<212> TYPE: PRT
<213> ORGANISM: Homo sapiens

<400> SEQUENCE: 5

Val Glu Leu Phe Pro Asn Gly Gln Ser Val Gly Glu Lys Ile Phe Lys
1               5                   10                  15

Thr Ala Gly Phe Val Lys Pro Phe Thr Glu Ala Gln Leu Leu Cys Thr
                20                  25                  30

Gln Ala Gly Gly Gln Leu Ala Ser Pro Arg Ser Ala Ala Glu Asn Ala
            35                  40                  45

Ala Leu Gln Gln Leu Val Val Ala Lys Asn Glu Ala Ala Phe Leu Ser
        50                  55                  60

Met Thr Asp Ser Lys Thr Glu Gly Lys Phe Thr Tyr Pro Thr Gly Glu
65                  70                  75                  80

Ser Leu Val Tyr Ser Asn Trp Ala Pro Gly Pro Asn Asp Asp Gly
                85                  90                  95

Gly Ser Glu Asp Cys Val Glu Ile Phe Thr Asn Gly Lys Trp Asn Asp
            100                 105                 110

Arg Ala Cys Gly Glu Lys Arg Leu Val Val Cys Glu Phe
        115                 120                 125

<210> SEQ ID NO 6
<211> LENGTH: 28
<212> TYPE: PRT
<213> ORGANISM: Homo sapiens

<400> SEQUENCE: 6

Asp Val Ala Ser Leu Arg Gln Gln Val Glu Ala Leu Gln Gly Gln Val
1               5                   10                  15

Gln His Leu Gln Ala Ala Phe Ser Gln Tyr Lys Lys
            20                  25

<210> SEQ ID NO 7
<211> LENGTH: 24
<212> TYPE: PRT
<213> ORGANISM: Artificial Sequence
<220> FEATURE:
<223> OTHER INFORMATION: Preferred amino terminal sequence of
      rSPD(n/CRD) polypeptide.

<400> SEQUENCE: 7
```

-continued

```
Gly Ser Pro Gly Leu Lys Gly Asp Lys Gly Ile Pro Gly Asp Lys Gly
1               5                   10                  15

Ala Lys Gly Glu Ser Gly Leu Pro
            20

<210> SEQ ID NO 8
<211> LENGTH: 12
<212> TYPE: PRT
<213> ORGANISM: Aspergillus fumigatus

<400> SEQUENCE: 8

Ala Thr Trp Thr Cys Ile Asn Gln Gln Leu Asn Pro
1               5                   10
```

RECOMBINANT SURFACTANT PROTEIN D COMPOSITIONS AND METHODS OF USE THEREOF

CROSS-REFERENCE TO RELATED APPLICATIONS

This application is a divisional of U.S. application Ser. No. 10/830,959, filed Apr. 23, 2004, which is a continuation-in-part of PCT/GB02/04824, which was filed Oct. 25, 2002 and published in English, which application claimed the priority of Great Britain applications GB 0125638.7, filed Oct. 25, 2001, and GB 0209619.6, filed Apr. 26, 2002, the entireties of each of which are hereby incorporated by reference.

This invention relates to methods of treatment and diagnosis of disease, and molecules and compositions for use in such methods.

We disclose a recombinant fragment of Surfactant Protein D, as well as a nucleic acid encoding this protein. We demonstrate that this fragment retains the beneficial properties of Surfactant Protein D, and show that it may be used to treat various diseases. These diseases include inflammatory diseases, including chronic lung disease, neonatal chronic lung disease, asthma, including allergic asthma, particularly caused by house dust mite, as well as other diseases. The recombinant Surfactant Protein D fragment we disclose may also be used to treat allergies of various kinds.

SUMMARY

The present inventors have determined that SP-D binds to free nucleic acid, particularly DNA, via its carbohydrate binding activity. Recognition of free DNA is believed to be responsible for at least some of the beneficial effects of SP-D. Moreover, the inventors have determined that the DNA binding properties of SP-D, as well as other properties of this molecule, are retained in a recombinant fragment designated rSPD(n/CRD). According to a first aspect of the present invention, therefore, we provide an rSPD(n/CRD) polypeptide, fragment, homologue, variant or derivative thereof for use in a method of treatment or prophylaxis of a disease.

There is provided, according to a second aspect of the present invention, a method of treating an individual suffering from a disease or preventing the occurrence of a disease in an individual, the method comprising administering to the individual a therapeutically or prophylactically effective amount of an rSPD(n/CRD) polypeptide, fragment, homologue, variant or derivative thereof.

The disease preferably comprises an inflammatory disease, preferably eczema.

The disease may comprise an inflammatory disease, preferably an inflammatory lung disease selected from the group consisting of: neonatal chronic lung disease, neonatal respiratory distress syndrome (RDS), adult respiratory distress syndrome, chronic obstructive airways disease (COPD), asthma, cystic fibrosis, pulmonary fibrosis, emphysema, interstitial inflammatory lung disease, sarcoidosis, pneumonia, chronic inflammatory lung disease, neonatal chronic inflammatory lung disease.

Preferably, the disease is selected from the group consisting of: neonatal chronic lung disease, pulmonary emphysema, chronic obstructive pulmonary disease, cystic fibrosis and asthma.

The disease may comprise an allergy. The allergy is preferably an allergy is to house dust mite (*Dermatophagoides* spp), preferably *Dermatophagoides pteronyssinus* or *Dermatophagoides farinae*, or to fungi or fungal spores, preferably *Aspergillus fumigatus*. The allergy is preferably selected from the group consisting of: a seasonal respiratory allergy, allergic rhinitis, hayfever, nonallergic rhinitis, vasomotor rhinitis, irritant rhinitis, an allergy against grass pollens, tree pollens or animal danders, an allergy associated with allergic asthma, a food allergy and allergic eye diseases.

The disease may be one which is associated with microbial infection, including bacterial infection and viral infection, preferably a microbial infection of the lung.

We provide, according to a third aspect of the present invention, a method of reducing airway hyperresponsiveness, serum IgE levels, or eosinopilia in an individual, the method comprising administering to the individual an rSPD(n/CRD) polypeptide, fragment, homologue, variant or derivative thereof.

As a fourth aspect of the present invention, there is provided method of reducing alveolar macrophage number in an individual, preferably by enhancing clearance of apoptotic alveolar macrophages, or by enhancing clearance of necrotic alveolar macrophages, or both, the method comprising administering to the individual an rSPD(n/CRD) polypeptide, fragment, homologue, variant or derivative thereof.

In preferred embodiments, the rSPD(n/CRD) polypeptide comprises, preferably consists of, a sequence shown in SEQ ID NO: 1.

Preferably, a nucleic acid encoding an rSPD(n/CRD) polypeptide, or a fragment, homologue, variant or derivative thereof, preferably a nucleic acid comprising a sequence shown in SEQ ID NO: 2, is administered to the individual.

We provide, according to a fifth aspect of the present invention, use of a rSPD(n/CRD) polypeptide, nucleic acid, fragment, homologue, variant or derivative thereof in a method of treatment or prophylaxis of a disease.

The present invention, in a sixth aspect, provides a recombinant polypeptide comprising a SP-D fragment having a sequence shown in SEQ ID NO: 1, or a fragment, homologue, variant or derivative thereof.

In a seventh aspect of the present invention, there is provided a nucleic acid comprising a sequence encoding a recombinant polypeptide according to the sixth aspect of the invention. Preferably, the nucleic acid comprises the sequence shown in SEQ ID NO: 2.

According to an eighth aspect of the present invention, we provide a vector, preferably an expression vector, comprising a nucleic acid sequence according to the seventh aspect of the invention.

We provide, according to a ninth aspect of the invention, a host cell transformed with a vector according to the eighth aspect of the invention. There is provided, in accordance with a tenth aspect of the present invention, a pharmaceutical composition comprising a recombinant polypeptide according to the sixth aspect of the invention, a nucleic acid according to the seventh aspect of the invention, a vector comprising a nucleic acid according to the eighth aspect of the invention, or a host cell according to the ninth aspect of the invention, together with a pharmaceutically acceptable carrier or diluent.

As an eleventh aspect of the invention, we provide a method of identifying a molecule which binds to an rSPD(n/CRD) polypeptide, the method comprising exposing a rSPD(n/CRD) polypeptide, fragment, homologue, variant or derivative thereof to a candidate molecule and detecting whether the candidate molecule binds to the rSPD(n/CRD) polypeptide, etc.

According to a twelfth aspect of the present invention, we provide a method of identifying an agonist or antagonist of an rSPD(n/CRD) polypeptide, the method comprising: (a) providing a cell or organism; (b) exposing the cell or organism to an rSPD(n/CRD) polypeptide, nucleic acid, or a fragment, homologue, variant or derivative thereof; (c) exposing the cell to a candidate molecule; and (d) detecting an rSPD(n/CRD) mediated effect.

The rSPD(n/CRD) mediated effect is preferably selected from the group consisting of: reduction of peripheral blood eosinophilia, reduction of serum IgE levels, reduction of serum IgG1 levels, reduction in airway hyperresponsiveness, reduction in alveolar macrophage number, reduction of phospholipid levels in lavage, down-regulation of Eotaxin expression, reduction in MCP-1 expression, down-regulation of MIP-1α expression, and down-regulation of MTP-2 expression. The method preferably further comprises isolating or synthesising a selected or identified molecule.

There is provided, according to a thirteenth aspect of the present invention, a molecule identified or selected using a method according to the twelfth aspect of the invention.

We provide, according to a fourteenth aspect of the present invention, composition comprising an rSPD(n/CRD) polypeptide, nucleic acid, or a fragment, homologue, variant or derivative thereof, together with one or more of the following components: a lung extract, preferably a bovine, preferably, calf lung extract, or a component thereof a phospholipid, preferably a phosphatidylcholine or a disaturated phosphatidylcholine, a fatty acid, a surfactant-associated protein, preferably a surfactant-associated protein B or a surfactant-associated protein C, a cetyl alcohol, a long-chain repeating alcohol, tyloxapol, colfosceril palmitate (dipalmitoylphosphatidylcholine), palmitic acid, tripalmitin, poractant alfa and sodium chloride.

As a fifteenth aspect of the present invention, there is provided use of an rSPD(n/CRD) polypeptide, nucleic acid, or a fragment, homologue, variant or derivative thereof in surfactant replacement therapy.

We provide, according to a sixteenth aspect of the present invention, an rSPD(n/CRD) polypeptide, nucleic acid, or a fragment, homologue, variant or derivative thereof in surfactant replacement therapy for use in surfactant replacement therapy.

According to a seventeenth aspect, there is provided the use of SP-D or a fragment thereof in the manufacture of a composition for the treatment of a condition involving the production of free DNA on the surface of cells. SP-D and fragments thereof, including rSPD(n/CRD), bind to DNA via their carbohydrate binding capacity. The fragments of SP-D accordingly advantageously retain the carbohydrate binding ability of native SP-D. The invention moreover provides a method for treating a patient suffering from a condition involving the production of free DNA on the surface of cells comprising administering to a patient in need of such treatment a pharmaceutically effective amount of SP-D or a fragment thereof.

The invention provides the use of SP-D or a fragment thereof in the manufacture of a composition for the treatment of a chronic infection which results in the accumulation of free nucleic acid in the lung. For example, the infection may be a bacterial, viral or fungal infection.

The invention moreover provides the use of SP-D or a fragment thereof in the manufacture of a composition for the treatment of cystic fibrosis. In cystic fibrosis, free nucleic acid is produced by bacterial cells in the lung, which leads to bacterial bio-film formation and persistent bacterial lung infection. SP-D and fragments thereof also act to opsonise many pulmonary pathogens, increasing the effectiveness of cystic fibrosis treatment.

In a further aspect, there is provided the use of SP-D or a fragment thereof in the manufacture of a composition for the clearance of necrotic and apoptotic cells. Such cells have DNA at their surfaces, which is bound by SP-D and fragments thereof for phagocyte-mediated clearance. Thus, the invention extends to compositions for the treatment of lung diseases and conditions such as COPD, chronic inflammation and chronic asthma using SP-D or fragments thereof and to methods for treating a patient suffering from a selected from the group consisting of cystic fibrosis, lung diseases, COPD, chronic inflammation, chronic bacterial infection, chronic viral infection, chronic fungal infection and chronic asthma comprising administering to a patient in need of such treatment a pharmaceutically effective amount of SP-D or a fragment thereof.

In a still further aspect, there is provided the use of SP-D or a fragment thereof in the manufacture of a composition for the treatment of autoantibody production in autoimmune diseases; as well as a method for treating a patient suffering from an autoimmune disease comprising administering to a patient in need of such treatment a pharmaceutically effective amount of SP-D or a fragment thereof.

Free DNA or DNA debris from necrotic or apoptotic cells can act as an autoantigen, resulting in autoantibody production. Clearance of such free DNA by SP-D and fragments thereof reduces autoantibody production. Other aspects of the invention are set out in the independent and dependent claims, as well as set out in the description.

BRIEF DESCRIPTION OF THE DRAWINGS

FIG. 1A depicts the structure a recombinant fragment of human SP-D (rSPD(n/CRD)). This is composed of trimers of the neck region and carbohydrate recognition domain (CRD) and has been expressed, purified and characterised in the MRC Immunochemistry Unit at Oxford University.

FIG. 1B. SDS-PAGE of 1 week culture filtrate of *Aspergillus fumigatus* showing a dominant 18 kDa band (Asp f 1).

FIG. 2A. Serum IgE in Afu mouse model measured 3 days after treatment with 5 daily doses of 10 μg rSPD(n/CRD) or PBS given intranasally after intranasal challenge with Afu 1 wcf and after re-challenge 1 week later with Afu alone. P=PBS treated nonsensitised mice, AP=PBS treated sensitised mice, AR=rSPD(n/CRD) treated sensitised mice, APrc=Afu rechallenged mice treated with PBS, ARrc=Afu rechallenged mice treated with rSPD(n/CRD).

FIG. 2B. Afu-specific IgE in Afu mouse model. As FIG. 2A above, but Afu-specific IgG1 is measured.

FIG. 3. Peripheral blood eosinophilia in Afu mouse model measured 1 day after treatment with 4 daily doses of 10 μg rSPD(n/CRD) or PBS given intranasally after intranasal challenge with Afu 1 wcf and after re-challenge 1 week later with Afu alone. P=PBS treated non-sensitised mice, AP=PBS treated sensitised mice, AR=rSPD(n/CRD) treated sensitised mice, APrc=Afu rechallenged mice treated with PBS, ARrc=Afu rechallenged mice treated with rSPD(n/CRD).

FIGS. 4A, 4B and 4C. Cytokines in Afu mouse model measured 1 day after treatment with 2 daily doses of 10 μg rSPD(n/CRD) given intranasally alter intranasal challenge with Afu 1 wcf. FIG. 4A IL-12 measured in the spleen, FIG. 4B IFN-γ measured in the spleen and FIG. 4C IL-4 measured in the spleen. P=PBS treated non-sensitised mice, AP=PBS treated sensitised mice, AR=rSPD(n/CRD) treated sensitised mice, AA=rhSP-A treated sensitised mice.

FIGS. 5A and 5B. Airway hyper-responsiveness in Afu mouse model. Mice are treated with 4 daily doses of 10 μg rSPD(n/CRD) given intranasally after intranasal challenge with Afu 1 wcf. Plethysmography is measured 2 hours after an intranasal re-challenge with Afu 1 wcf alone given 3 days after completion of treatment. Figures A Dose response to increasing doses of methacholine. FIG. 5B Response to 30 mg/ml methacholine after treatment with 4 daily doses of 10 μg rSPD(n/CRD) or rhSP-A given intranasally after intranasal challenge with Afu 1 wcf. P=PBS treated non-sensitised mice, AP=PBS treated sensitised mice, AR=rSPD(n/CRD) treated sensitised mice, AA=rfhSP-A treated sensitised mice.

FIGS. 6A and 6B. Afu mouse model H&E stained lung sections of sensitised mice after treatment FIG. 6A with PBS FIG. 6B with rSPD(n/CRD) or c nonsensitised mouse treated with PBS.

FIG. 7A. An analysis of IL-12 in the lung homogenates of Der p sensitised mice after treatment measured by intracellular cytokine staining followed by FACS analysis for the percentage of highly stained cells (PE>1000) positive for IL-12. PBS non-sensitised mice treated with PBS. HP=sensitised mice treated with PBS. HR=sensitised mice treated with 10 μg rSP-D (N/CRD).

FIG. 7B. An analysis of IL-12 in the spleen homogenates of Der p sensitised mice after treatment measured by intracellular cytokine staining followed by FACS analysis for the percentage of highly stained cells (PE>1000) positive for IL-12. PBS=non-sensitised mice treated with PBS. HP=sensitised mice treated with PBS. HR=sensitised mice treated with 10 μg rSP-D (N/CRD). HB=sensitised mice treated with 10 μg BSA.

FIG. 7C. An analysis of IFN-γ in the spleen homogenates of Der p sensitised mice after treatment measured by intracellular cytokine staining followed by FACS analysis for the percentage of highly stained cells (PE>1000) positive for IFN-γ. PBS=non-sensitised mice treated with PBS. HP=sensitised mice treated with PBS. HR=sensitised mice treated with 10 μg rSP-D (N/CRD).

FIG. 7D. An analysis of TNF-α in the spleen homogenates of Der p sensitised mice after treatment measured by intracellular cytokine staining followed by FACS analysis for the percentage of highly stained cells (PE>1000) positive for TNF-α. PBS=non-sensitised mice treated with PBS. HP=sensitised mice treated with PBS. HR=sensitised mice treated with 10 μg rSP-D (N/CRD).

FIG. 8A (entitled "Average Penh response to a 1 min challenge with 20 mg/ml methacholine on the 4th day of treatment") is a graph showing the effect of treatment with rSPD (n/CRD) on the airway hyperresponsiveness (AHR) of allergic mice, measured on the last day of 4 days of treatment. The allergic mice are sensitised to Dermatophagoides pteronyssinus. The PBS control represents non-sensitised mice treated with PBS. Average Perth response to a 1 minute challenge with 20 mg/ml methacholine on the $4^{th}$ day of treatment is shown. X-axis: left: PBS control, middle: Der p-PBS, right: Der p-rSPD; Y-axis: % Penh above background.

FIG. 8B (entitled "Airway hyperresponsiveness in allergic mice induced by methacholine challenge") is a graph showing the dose response to methacholine, following allergen re-challenge 4 days after treatment with PBS or rSPD(n/CRD). The allergic mice are sensitised to Dermatophagoides pteronyssinus. The PBS-PBS control represents non-sensitised mice treated with PBS. Airway hyperresponsiveness (AHR) is measured in allergic mice induced by methacholine challenge. X-axis: methacholine (mg/ml); diamonds: PBS-PBS, squares: Der p-PBS, triangles: Der p-rSPD.

FIG. 9 is a graph showing the effect of rSP-D (N/CRD) treatment on alveolar macrophage number, following lavage. X-axis: age in weeks; Y-axis: alveolar macrophage number× $10^4$ per mouse lavage.

FIG. 10A shows a cytospin of cells in bronchoalveolar lavage. Alveolar macrophages are stained with Malachite green (upper panels) or crystal violet (lower panels) after cytospin. Morphology is shown for no treatment (upper left panels), BSA treated (upper right panels) and r-SP-D treated (lower panels).

FIG. 10B shows a cyto spin of cells in bronchoalveolar lavage. Upper left: untreated cells from SP-D deficient mice; upper right: cells from wild-type mice; lower left: cells from SP-D deficient mice treated with BSA; lower right: cells from SP-D deficient mice treated with rSP-D FIG. 11 (entitled "Phospholipid in cell-free lavage supernatant per mouse") is a graph showing the effect of rSP-D (N/CRD) treatment on total BAL phospholipid levels. Phospholipid in cell-free lavage supernatant is shown per mouse. X-axis: age in weeks; Y-axis: phospholipid in μg per mouse.

FIG. 12 (entitled "Chemokine mRNA levels in SP-D KO mice compared to WT and the effect of treatment with rSP-D") are graphs showing chemokine mRNA levels in SP-D knockout mice compared to wild type and the effect of treatment with rSP-D(N/CRD).

FIG. 13B shows the typical patterns of annexin V and PI staining of macrophages from SP-D deficient mice compared to wild-type mice.

FIGS. 16A and 16B show enhanced phagocytosis of apoptotic (orange labelled) macrophages by freshly isolated green macrophages.

Figure 18:
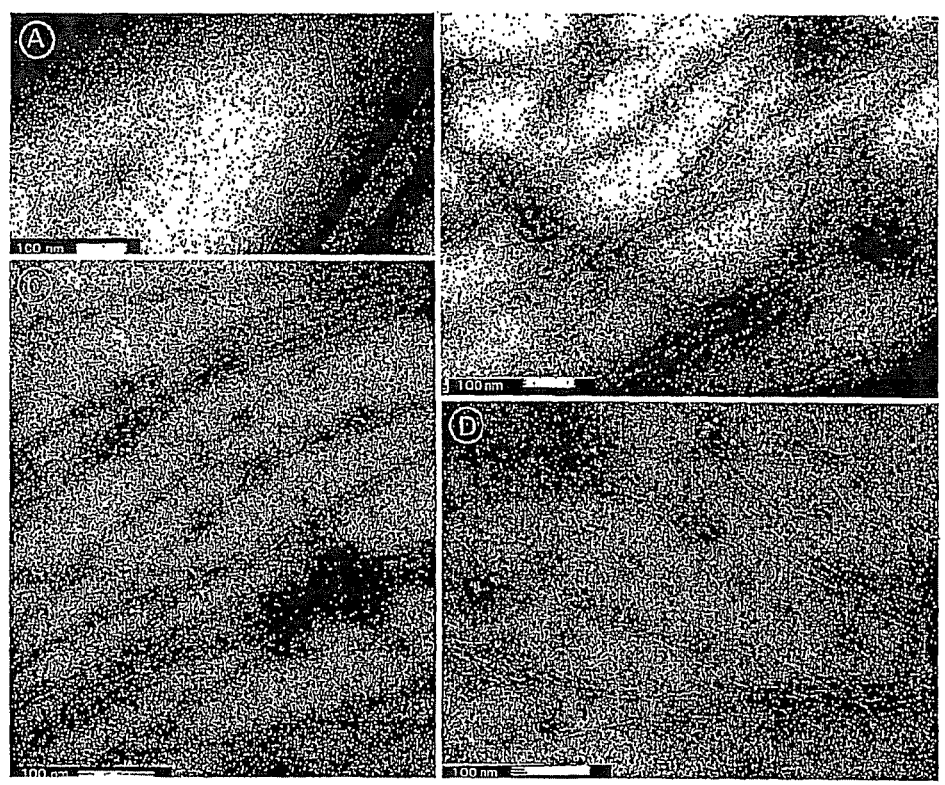

FIG. 18 shows negatively stained transmission electron microscopic images of genomic DNA and complexes between SP-D and DNA. A, genomic DNA; B & C, genomic DNA complexed with rSPD(n/CRD); D, genomic DNA complexed with native SP-D.

Figure 19:
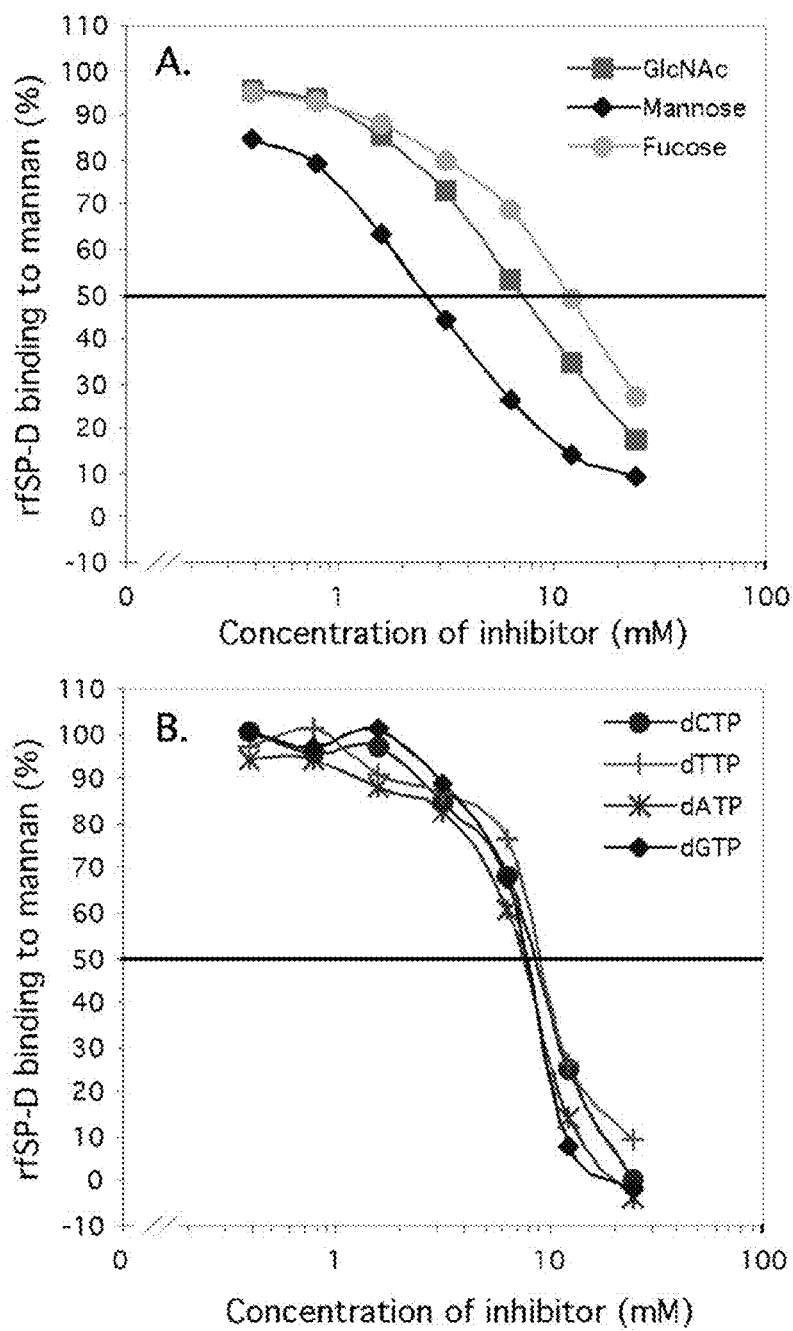

FIG. 19 demonstrates binding between rSPD(n/CRD) and mannan is competed by deoxyribonucleotides. A fixed concentration of rSPD(n/CRD) (100 μg/mL) was allowed to bind to biotinylated mannan that was immobilised on a SA BIAcore chip in the presence of indicated concentrations of hexoses (A) or dNTPs (B) in 5 mM $CaCl_2$-containing saline buffer.

Figure 20:
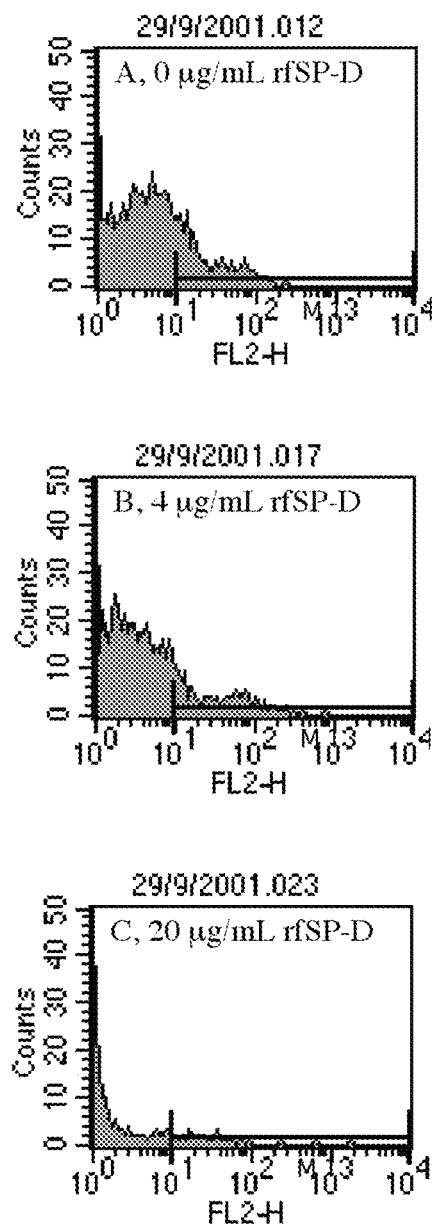

FIG. 20 shows inhibition of propidum iodide binding by rSPD(n/CRD).

Figure 21:
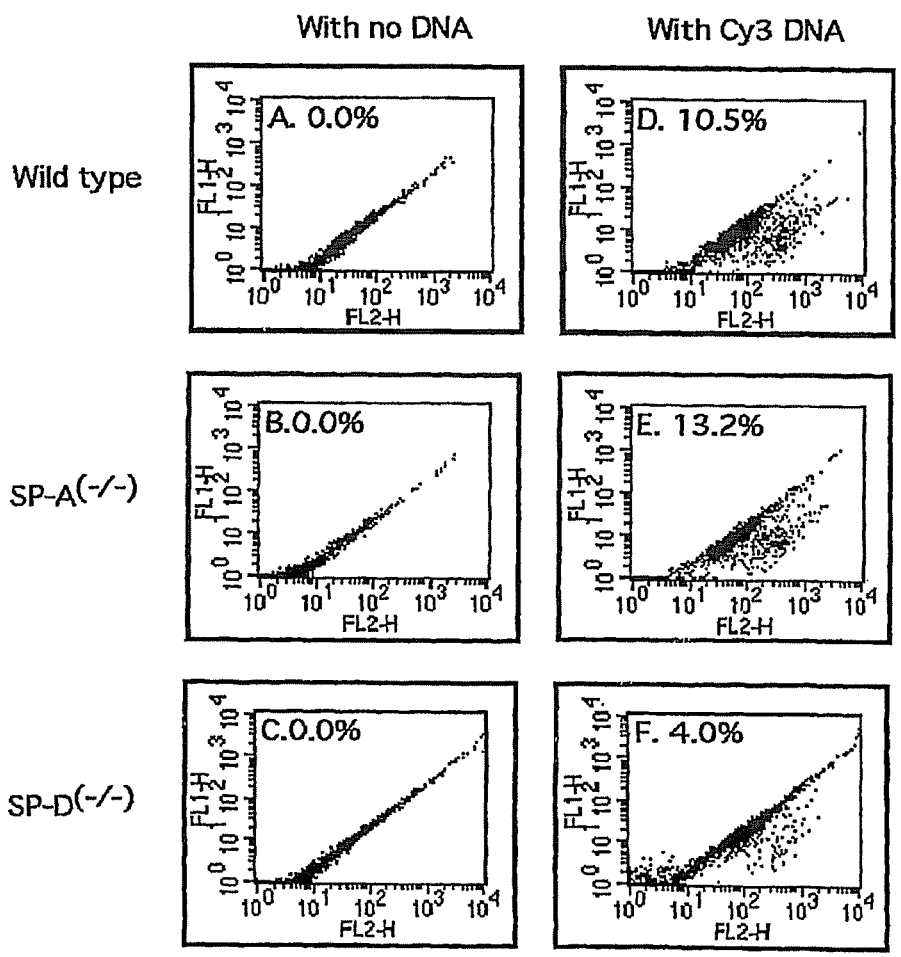

FIG. 21 shows that alveolar macrophages isolated from SP-D knock-out mouse are defective in clearing DNA. Alveolar macrophages were isolated from the lung lavage of wild-type (A,D) or SP-A knock-out mice (SP-A($-/-$)) (B,E) or SP-D knockout mice (SP-D($-/-$)) (C,F), washed and incubated with either buffer (A,B,C) or Cy3-labelled (red) lung DNA (D,E,F). The uptake of DNA was monitored by FACS at FL2-H and graphed against a non-specific FL1-H. The proportion of alveolar macrophages that took up the DNA was indicated in the figure (D,E,F).

DETAILED DESCRIPTION

We disclose the sequence and method of production of a recombinant SP-D fragment, referred to here as "rSPD(n/CRD) polypeptide". As far as we are aware, the sequence and production of rSPD(n/CRD) polypeptide has not previously been made known. We show that rSPD(n/CRD) polypeptides are capable of associating with each other and forming timers in solution.

In a highly preferred embodiment, we describe the use of rSPD(n/CRD) polypeptide, nucleic acid, or a fragment, homologue, variant or derivative thereof for use as a surfactant replacement therapy, particularly for neonates. rSPD(n/CRD) polypeptide, nucleic acid, or a fragment, homologue, variant or derivative thereof may suitably be employed for the treatment of neonatal lung diseases, particularly, neonatal chronic lung diseases.

We demonstrate that rSPD(n/CRD) polypeptide reduces peripheral blood eosinophilia and total serum IgE levels, as well as IgG1 levels, when administered to knock-out mice lacking Surfactant Protein D and challenged with allergen. rSPD(n/CRD) polypeptide is therefore suitable for use as a modulator of allergic hypersensitivity reactions in individuals. rSPD(n/CRD) polypeptide is also suitable for use in treating any disease or syndrome characterised in peripheral blood eosinophilia, elevated serum IgE levels, elevated IgG1 levels, or any combination of these.

rSPD(n/CRD) polypeptide may also be used for regulation of macrophage mediated inflammation in the lung, as well as in the defence against invasion by pathogens and in modulating inflammatory responses to infection and allergenic stimuli.

Mice, for example C57Bl16 wild-type mice, sensitised and challenged with house dust mite allergen show airway hyperresponsiveness characteristic of allergic asthma. Administration of rSPD(n/CRD) polypeptide to such mice reduces airway hyperresponsiveness. Accordingly, rSPD(n/CRD) polypeptide may be administered to individuals to treat any disease or syndrome in which airway hyperresponsiveness occurs, including allergic asthma.

Other diseases for which treatment of rSPD(n/CRD) polypeptide may be employed include skin conditions, for example, eczema (which is a Th2 mediated disease), as well as allergies in general. Such allergies include food allergies, for example against allergens such as egg, tree nut, peanut, and milk. Other common allergens include pollens, dust, mould, and mildew, as well as insect, domestic animal (dog, cat, bird), and plant allergens. Also included are seasonal respiratory allergies, commonly referred to as hay fever, aeroallergens, which include house dust mite, fungal spores, grass pollens, tree pollens and animal danders.

Other categories of allergies, which may be treated with rSPD(n/CRD) are those which might benefit from the reduction in airway hyperresponsiveness, serum IgE and eosinophilia which are major factors in producing the symptoms of allergy. This includes the treatment of allergic asthma. rSPD(n/CRD) may also be used as an effective treatment for conditions that would benefit from the up-regulation of the cell-mediated immune system. This includes anti-microbial action and the treatment of lung infections.

rSPD(n/CRD) may be used as an effective treatment for conditions that would benefit from the up-regulation of the activity of Natural Killer cells and the secretion of the cytokine IFNγ by cells of the immune system. This includes the treatment of lung cancer and other cancers and neoplasms.

rSPD(n/CRD) may also be used as an effective treatment for conditions that would benefit from the supplementation of endogenous natural SP-D with rSPD(n/CRD). This includes the treatment of conditions in which the level of endogenous natural SP-D is abnormally low. This includes the treatment of neonates with disorders of the lung surfactant system in which the level of endogenous natural SP-D is abnormally low. This also includes the treatment of cystic fibrosis patients in which the level of endogenous natural lung SP-D is abnormally low. This also includes the treatment of patients with other infections of the lung in which the level of endogenous natural SP-D is abnormally low.

In a further embodiment, SP-D's anti-allergic properties can be harnessed to combat allergic eye disease. The invention thus provides SP-D, or a fragment thereof such as rSPD(n/CRD), for the treatment of allergic eye conditions.

We have measured surfactant protein D levels in human tears and found this to be 132 ng/ml. The fact that SP-D has anti-allergic properties as set forth herein and is present in human tear fluid suggests that the protein is involved in the natural anti-allergic effect of tears. SP-D or rSP-D(n/CRD) can be added to, for example, contact lens solution to help offset irritation/inflammation by contact lenses. Moreover, it is a valuable addition in the treatment of for example Sjogren's syndrome—an autoimmune disease characterised by dry eyes dry mouth (caused by autoantibodies to human salivary and lacrimal gland components). This is currently treated with artificial tear supplementation (such as hypermellose eye drops) and the addition of SP-D or fragments thereof to such formulations enhances the protective effect of artificial tears against eye infections and corneal inflammation.

Where reference is made to rSPD(n/CRD) above, this should be taken to refer to the polypeptide itself or a fragment, homologue, variant or derivative thereof.

Where reference is made to a treatment of a disease, this should be taken to include reference to alleviation of a symptom of that disease. Preferably, substantially all of the symptoms of an individual having that disease are alleviated or removed. "Disease" should be taken to include any syndrome, as well as any condition affecting the health or well-being of an individual. Preferably, an individual to which an rSPD(n/CRD) polypeptide, fragment, homologue, variant or derivative thereof is administered is relieved to at least one symptom of the disease or condition, i.e., he reverts substantially to the state of a normal unaffected individual. This may be assessed by a physician using a relevant clinical parameter. For example, airway hyperresponsiveness may be measured using the methods set out in the Examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, Sambrook, J., E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); Roe, B., J. Crabtree, and A. Kahn, 1996, *DNA Isolation and Sequencing: Essential Techniques*, John Wiley & Sons; Polak, J. M. and James O'D.

McGee, 1990, *In Situ Hybridization: Principles and Practice*; Oxford University Press; M. J. Gait (Editor), 1984, *Oligonucleotide Synthesis: A Practical Approach*, Irl Press; and, Lilley, D. M. J. and J. E. Dahlberg, 1992, *Methods of Enzymology: DNA Structure Part A: Synthesis and Physical Analysis of DNA*, Methods in Enzymology, Academic Press. Each of these general texts is herein incorporated by reference.

Surfactant Protein D rSPD(n/CRD)

Surfactant Protein D has been identified and characterised previously, in for example Rust et al., 1991, *Human surfactant protein D: SP-D contains a C-type lectin carbohydrate recognition domain*, Archives of Biochemistry and Biophysics 290 (1):116-126; Lu et al., 1992, *Purification, Characterization and cDNA Cloning of Human Lung Surfactant Protein D*, Biochem. J. 284:785-802; Crouch et al., 1993, *Genomic organization of human surfactant protein D (SP-D). SP-D is encoded on chromosome 10q22.2-23.1*, The Journal of Biological Chemistry 268 (4): 2976-2983; Kolble et al., 1993, *Assignment of the human pulmonary surfactant protein D gene (SFTP4) to 10q22-q23 close to the surfactant protein A gene cluster*, Genomics 17 (2):294-298.

Where the terms "Surfactant Protein D", "SP-D", "hSP-D" and "natural SP-D" are used, these should be taken to refer to any Surfactant Protein D polypeptide or nucleic acid (as the context requires). Preferably, however, these terms should be taken to refer to human Surfactant Protein-D, for example, the sequences disclosed in the above references, or in GenBank accession numbers NM_003019.1, XM_005776.2, X65018.1 and L05485.1. Most preferably, the Surfactant Protein D is a human Surfactant Protein D having the GenBank accession numbers NM_003019.1. The nucleic acid and amino acid sequences of such a human SP-D are shown in SEQ ID NO: 3 and SEQ ID NO: 4 respectively.

Recombinant Surfactant Protein D rSPD(n/CRD) Polypeptides

We provide for a polypeptide fragment of Surfactant Protein D (SP-D), which we refer to as rSPD(n/CRD). The sequence of such a rSPD(n/CRD) polypeptide is shown in SEQ ID NO: 1. rSP-D (N/CRD) is also referred to in this document as "rhSP-D", and the two terms should be regarded as synonymous.

Where the term rSP-D is employed, this should be taken to refer generally to recombinant SP-D, whether corresponding to full length SP-D, preferably human SP-D (expressed in a recombinant manner), or a fragment of this. Preferably, the term rSP-D should be taken to refer to a recombinant fragment of SP-D, preferably human SP-D. Preferably, and where the context requires, "rSP-D" should be taken to refer to the recombinant SP-D fragment rSPD(n/CRD) described above.

It will be understood that polypeptides disclosed here are not limited to the particular rSPD(n/CRD) sequence shown in SEQ ID NO: 1, but also include fragments thereof. Particularly preferred fragments include those having one or more biological activities of rSPD(n/CRD).

Furthermore, the rSPD(n/CRD) polypeptides also generally include any recombinant fragment of SP-D, preferably human SP-D, which lacks the N-terminal domain and/or the collagen domain, preferably both. Thus, in a preferred embodiment, the rSPD(n/CRD) polypeptide is a recombinant fragment of SP-D, preferably human SP-D depicted in SEQ ID NO: 4, which lacks substantially lacks residues 1-178. In a further preferred embodiment, the rSPD(n/CRD) polypeptide is a recombinant fragment of SP-D, preferably human SP-D sequence shown in SEQ ID NO: 4, comprising substantially residues 179-355.

In a preferred embodiment, the proline residue corresponding to position 200 of the human SP-D sequence (SEQ ID NO: 4) is replaced by another residue. Preferably, the proline residue is replaced with a uncharged polar residue, for example, a cysteine, serine, threonine or methionine residue. In a highly preferred embodiment, the proline residue is replaced with a serine residue. Thus, the rSPD(n/CRD) polypeptide may comprise a sequence shown in SEQ ID NO: 1.

Fragments, homologues, variants and derivatives of each of the above sequences are also included.

In preferred embodiments, the rSPD(n/CRD) polypeptide comprises a "head" region or carbohydrate recognition domain (CRD), comprising substantially the following residues:

VELFPNGQSVGEKIFKTAGFVK-PFTEAQLLCTQAGGQLASPRSAAENAALQQLV VAKNEAAFLSMTDSKTEGKFTYPT-GESLVYSNWAPGEPNDDGGSEDCVEIFTNG KWN-DRACGEKRLVVCEF (SEQ ID NO: 5) Preferably, the rSPD (n/CRD) polypeptide comprises means for multimerisation, preferably trimerisation, with another rSPD(n/CRD) polypeptide. Such means may include for example, a biotin moiety which interacts with and binds to an avidin or streptavidin moiety on another rSPD(n/CRD) polypeptide.

In further preferred embodiments, the rSPD(n/CRD) polypeptide further comprises a "neck" region comprising substantially the following residues:

```
DVASLRQQVEALQGQVQHLQAAFSQYKK        (SEQ ID NO: 6)
```

Preferably, such a neck region is N terminal to the carbohydrate recognition domain (CRD).

In a preferred embodiment, the rSPD(n/CRD) polypeptide further comprises at least one Gly-Xaa-Yaa stretch, preferably a sequence comprising a plurality of Gly-Xaa-Yaa repeats, most preferably a sequence comprising 8 Gly-Xaa-Yaa repeats. In a preferred embodiment, the rSPD(n/CRD) polypeptide further comprises a N-terminal sequence comprising substantially GSPGLKGDKGIPGDKGAKGESGLP (SEQ ID NO: 7).

In a highly preferred embodiment, the rSPD(n/CRD) polypeptide comprises, preferably consists of, a sequence shown in SEQ ID NO: 1. Thus, as used in this document, the term "rSPD(n/CRD) polypeptide" should preferably be taken to refer to the sequence below:

```
                                     (SEQ ID NO: 1)
GSPGLKGDKGIPGDKGAKGESGL P DVASLRQQVEALQGQVQHLQAAFS

QYKKVELFPNGQSVGEKIFKTAGFVKPFTEAQLLCTQAGGQLASPRSAA

ENAALQQLVVAKNEAAFLSMTDSKTEGKFTYPTGESLVYSNWAPGEPND

DGGSEDCVEIFTNGKWNDRACGEKRLVVCEF
```

(SEQ ID NO: 1), as well as a fragment, homologue, variant or derivative thereof. A (G-Xaa-Yaa)$_8$ motif is present at amino acids 1-24, a "neck" domain is present at amino acids 25-53, and a "head" domain is present at amino acids 54-177. Nucleotide sequences of SEQ ID NO:2 corresponding to these domains are: (G-Xaa-Yaa)$_8$, 1-72; "neck," 73-156; and "head," 157-534.

The polypeptides disclosed also include homologous sequences obtained from any source, for example related viral/bacterial proteins, cellular homologues and synthetic peptides, as well as variants or derivatives thereof. Thus polypeptides also include those encoding homologues of rSPD(n/CRD) from other species including animals such as mammals (e.g. mice, rats or rabbits), especially primates, more especially humans. More specifically, homologues include human homologues.

Thus, we disclose variants, homologues or derivatives of the amino acid sequence of rSPD(n/CRD) sequence shown in SEQ ID NO: 1, as well as variants, homologues or derivatives of a nucleotide sequence encoding such amino acid sequences.

Preferably, the rSPD(n/CRD) polypeptides, variants, homologues, fragments and derivatives disclosed here comprise one or more properties of rSPD(n/CRD), preferably one or more biological activities of rSPD(n/CRD). Thus, the variants, etc. preferably comprise one or more activities including but not limited to, carbohydrate binding activity, multimerisation activity, including trimerisation activity, down-regulation of chemokines, reduction of airway hyperresponsiveness, reduction in alveolar macrophage number, reduction in phospholipid level, when administered to an animal lacking SP-D, increased clearance of apoptotic and/or necrotic macrophages, reduction in peripheral blood eosinophilia, reduction in serum IgE, reduction in serum IgG1, as well as any of the biological activities or properties disclosed in the Examples.

In the context of this document, a homologous sequence is taken to include an amino acid sequence which is at least 15, 20, 25, 30, 40, 50, 60, 70, 80 or 90% identical, preferably at least 95 or 98% identical at the amino acid level over at least 50 or 100, preferably 200, 300, 400 or 500 amino acids with the sequence of rSPD(n/CRD) shown in SEQ ID NO: 1. In particular, homology should typically be considered with respect to those regions of the sequence known to be essential for protein function rather than nonessential neighbouring sequences. This is especially important when considering homologous sequences from distantly related organisms.

Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These publicly and commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid.—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid., pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The terms "variant" or "derivative" in relation to the amino acid sequences of the present invention includes any substitution of, variation of, modification of, replacement of, deletion of or addition of one (or more) amino acids from or to the sequence providing the resultant amino acid sequence retains substantially the same activity as the unmodified sequence, preferably having at least the same activity as the rSPD(n/CRD) polypeptide shown in SEQ ID NO: 1.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains of the polypeptides described here. Functional domains of rSPD(n/CRD) include the collagen domain, the neck region and the carbohydrate recognition domain. Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
|  |  | I L V |
|  | Polar - uncharged | C S T M |
|  |  | N Q |
|  | Polar - charged | D E |
|  |  | K R |
| AROMATIC |  | H F W Y |

As an example, relative to SEQ ID NO: 1, each of the substitutions G59A, I66L, F76Y, E78D and Q80N represent conservative substitutions.

Polypeptides also include fragments of the full length sequence of Surfactant Protein D. Preferably fragments comprise at least one epitope. Methods of identifying epitopes are well known in the art. Fragments will typically comprise at least 6 amino acids, more preferably at least 10, 20, 30, 50 or 100 amino acids.

Polypeptides also include fragments of the full length sequence of Surfactant Protein D (SEQ ID NO: 4) or rSPD (n/CRD) (SEQ ID NO: 1) that retain one or more biological activities of the polypeptide of SEQ ID NO: 4 or SEQ ID NO: 1. Preferably fragments comprise at least one epitope. Methods of identifying epitopes are well known in the art. An epitope will typically comprise at least 6 amino acids, more preferably at least 10, 20, 30, 50, or 100 amino acids.

As used herein, the phrase "retain one or more biological activities" means that a fragment has at least 20% or one or more biological activities of the full length rSPD(n/CRD) of SEQ ID NO: 1.

Fragments of rSPD(n/CRD) include, for example, polypeptides comprising amino acids 4-177, 7-177, 10-177, 13-177, 16-177, 19-177, 22-177, 25-177, 30-177, 35-177, 40-177, 45-177, 50-177, 53-177, 60-177, 70-177, 80-177, 90-177, 100-177, 110-177, 120-177, 130-177, 140-177, 1-176, 1-175, 1-174, 1-173, 1-172, 1-171, 1-170, 1-160, 1-150, 1-140, 1-130, 1-120, 1-110, 1 100, 1-90, 1-80, 1-70, 1-60, 25-176, 25-175, 25-174, 25-173, 25-172, 25-171, 25-170, 25-160, 25-150, 25-140, 25-130, 25-120, 25-110, 25-100, 25-90, 25-80, 25-70, 54-177, 54-176, 54-175, 54-174, 54-173, 54-172, 54-170, 54-160, 54-150, 54-140, 54-130, 54-120, 54-110, 54-100, 54 90, 54-80 and 54-700 of SEQ ID NO: 1, and corresponding fragments of SEQ ID NO: 4. The above-noted fragments and others are encoded by the corresponding nucleic acid fragment sequences found within SEQ ID NO: 2 and/or SEQ ID NO: 3.

As used herein, the terms "reducing," "reduces," "decreasing," "decreases," "down-regulating" or "down-regulation," when applied to a symptom of a disease or disorder or to a measurable parameter, e.g., alveolar macrophage number, expression of a gene, etc., means at least a 10% reduction relative to the symptom or parameter measured in a system, model or individual not administered an rSPD(n/CRD) polypeptide.

As used herein, the terms "enhances," "enhancing," "increases" or "increasing," when applied to a measurable parameter, e.g., apoptotic or necrotic macrophage clearance, etc., means at least a 10% reduction relative to the parameter measured in a system, model or individual not administered an rSPD(n/CRD) polypeptide.

Recombinant SP-D, including r-SP-D(N/CRD) and its fragments, homologues, variants and derivatives, are typically made by recombinant means, for example as described below in the Examples. However they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the function of the protein of interest sequence. Proteins may also be obtained by purification of cell extracts from animal cells.

The rSPD(n/CRD) polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A rSPD(n/CRD) variant, homologue, fragment or derivative may also be in a substantially purified form, in which case it will generally comprise the protein in a preparation in which more than 90%, e.g. 95%, 98% or 99% of the protein in the preparation is a protein.

The rSPD(n/CRD) polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

A rSPD(n/CRD) polypeptides, variants, homologues, fragments and derivatives disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise:

(a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The rSPD(n/CRD) polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the rSPD(n/CRD) polypeptides, variants, homologues, fragments and derivatives disclosed here are expressed may be used in assay systems to identify candidate substances which interfere with or enhance the functions of the polypeptides in the cell.

Recombinant Surfactant Protein D rSPD(n/CRD) Nucleic Acids

We provide for a nucleic acid encoding a rSPD(n/CRD) polypeptide, which we refer to as a "rSPD(n/CRD) nucleic acid". We also provide nucleic acids encoding variants, homologues, derivatives and fragments of rSPD(n/CRD), as well as fragments, homologues, derivatives and variants of rSPD(n/CRD) nucleic acids.

Preferably, the rSPD(n/CRD) nucleic acid is derived from a natural SP-D sequence, for example, the human SP-D sequence shown in SEQ ID NO: 3. More preferably, the rSPD(n/CRD) nucleic acid lacks sequence encoding the N-terminal domain and/or the collagen domain, preferably both. In a preferred embodiment, the rSPD(n/CRD) nucleic acid is a recombinant fragment of SP-D, preferably human SP-D depicted in SEQ ID NO: 3, which lacks substantially lacks residues 1-594, or any fragment, homologue, variant or derivative thereof. In a further preferred embodiment, the rSPD(n/CRD) nucleic acid is a recombinant fragment of SP-D, preferably human SP-D sequence shown in SEQ ID NO: 3, comprising substantially residues 595-1128. Fragments, homologues, variants and derivatives of each of the above sequences are also included.

In a preferred embodiment, a triplet encoding the proline residue corresponding to position 200 of the human SP-D sequence (SEQ ID NO: 4) is replaced by a codon encoding another residue. Preferably, the proline residue is replaced with a uncharged polar residue, for example, a cysteine, serine, threonine or methionine residue. In a highly preferred embodiment, the proline residue is replaced with a serine residue. Thus, preferably the rSPD(n/CRD) nucleic acid may comprise a codon encoding serine at position 598 to 560 of the human SP-D sequence shown in SEQ ID NO: 3. Such a replacement codon may therefore include AGC, AGT, TCA, TCC, TCG and TCT. Most preferably the replacement codon comprises AGC.

Preferably, such a rSPD(n/CRD) nucleic acid encodes the rSPD(n/CRD) polypeptide having the sequence shown in SEQ ID NO: 1. A rSPD(n/CRD) nucleic acid preferably comprises, more preferably consists of, a sequence as set out in SEQ ID NO: 2.

As used here in this document, the terms "polynucleotide", "nucleotide", and nucleic acid are intended to be synonymous with each other. "Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides. It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

rSPD(n/CRD) nucleic acids, variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of this document, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence. Preferably said variant, homologues or derivatives code for a polypeptide having biological activity.

As indicated above, with respect to sequence homology, preferably there is at least 50 or 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

We further describe nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Hybridization conditions are based on the melting temperature (Tm) of the nucleic acid binding complex, as taught in Berger and Kimmel, 1987, Guide to Molecular Cloning Techniques, Methods in Enzymology, Vol 152, Academic Press, San Diego, Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

In a preferred aspect, we provide nucleotide sequences that can hybridise to the rSPD(n/CRD) nucleic acids, fragments, variants, homologues or derivatives under stringent conditions (e.g. 65° C. and 0.1×SSC {1×SSC=0.15 M NaCl, 0.015 M $Na_3$ Citrate pH 7.0).

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

Polynucleotides which are not 100% homologous to the sequences of the present invention but which are also included can be obtained in a number of ways. Other variants of the sequences may be obtained for example by probing DNA libraries made from a range of individuals, for example individuals from different populations. For example, SPD homologues may be identified from other individuals, or other species. Further recombinant SP-D nucleic acids and polypeptides may be produced by identifying corresponding positions in the homologues, and synthesising or producing the molecule as described elsewhere in this document. Furthermore, the collagen region, neck region and carbohydrate binding domain in such homologues may be identified, for example, by sequence gazing or computer assisted comparisons, and selected for combination into or production of a recombinant SP-D which is non-human, but which has one or more biological activities of rSPD(n/CRD)

In addition, other viral/bacterial, or cellular homologues of SP-D particularly cellular homologues found in mammalian cells (e.g. rat, mouse, bovine and primate cells), may be obtained and such homologues and fragments thereof in general will be capable of selectively hybridising to human SP-D. Such homologues may be used to design non-human rSPD (n/CRD) nucleic acids, fragments, variants and homologues. Mutagenesis may be carried out by means known in the art to produce further variety.

Sequences of SP-D homologues may be obtained by probing cDNA libraries made from or genomic DNA libraries from other animal species, and probing such libraries with probes comprising all or part of any of the rSPD(n/CRD) nucleic acids, fragments, variants and homologues, or other fragments of SP-D under conditions of medium to high stringency.

Similar considerations apply to obtaining species homologues and allelic variants of the polypeptide or nucleotide sequences disclosed here.

Variants and strain/species homologues may also be obtained using degenerate PCR which will use primers designed to target sequences within the variants and homologues encoding conserved amino acid sequences within the sequences of the rSPD(n/CRD) nucleic acids. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences. It will be appreciated by the skilled person that overall nucleotide homology between sequences from distantly related organisms is likely to be very low and thus in these situations degenerate PCR may be the method of choice rather than screening libraries with labelled fragments the rSPD(n/CRD) sequences.

In addition, homologous sequences may be identified by searching nucleotide and/or protein databases using search algorithms such as the BLAST suite of programs.

Alternatively, such polynucleotides may be obtained by site directed mutagenesis of characterised sequences, for example, rSPD(n/CRD) nucleic acids, or variants, homologues, derivatives or fragments thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 8, 9, 10, or 15, preferably at least 20, for example at least 25, 30 or 40 nucleotides in length, and are also encompassed by the term "polynucleotides" as used herein.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Polynucleotides or primers may carry a revealing label. Suitable labels include radioisotopes such as $^{32}P$ or $^{35}S$, enzyme labels, or other protein labels such as biotin. Such labels may be added to polynucleotides or primers and may be detected using by techniques known per se. Polynucleotides or primers or fragments thereof labelled or unlabeled may be used by a person skilled in the art in nucleic acid-based tests for detecting or sequencing polynucleotides in the human or animal body.

Such tests for detecting generally comprise bringing a biological sample containing DNA or RNA into contact with a probe comprising a polynucleotide or primer under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this and other formats can be found in for example WO89/03891 and WO90/13667.

Tests for sequencing nucleotides, for example, the rSPD(n/CRD) nucleic acids, involve bringing a biological sample containing target DNA or RNA into contact with a probe comprising a polynucleotide or primer under hybridising conditions and determining the sequence by, for example the Sanger dideoxy chain termination method (see Sambrook et al.).

Such a method generally comprises elongating, in the presence of suitable reagents, the primer by synthesis of a strand complementary to the target DNA or RNA and selectively terminating the elongation reaction at one or more of an A, C, G or T/U residue; allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

Nucleic Acid Vectors

Polynucleotides, for example those described here, can be incorporated into a recombinant replicable vector. The vector may be used to replicate the nucleic acid in a compatible host cell. Thus in a further embodiment, we provide a method of making polynucleotides by introducing a polynucleotide into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors may be transformed or transfected into a suitable host cell as described below to provide for expression of a protein. This process may comprise culturing a host cell transformed with an expression vector as described above under conditions to provide for expression by the vector of a coding sequence encoding the protein, and optionally recovering the expressed protein. Vectors will be chosen that are compatible with the host cell used.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the polypeptide include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells, such as insect cells, may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Polynucleotides may also be inserted into the vectors described above in an antisense orientation to provide for the production of antisense RNA. Antisense RNA or other antisense polynucleotides may also be produced by synthetic means. Such antisense polynucleotides may be used in a method of controlling the levels of RNAs transcribed from genes comprising any one of the polynucleotides described here.

Host Cells

Vectors and polynucleotides comprising or encoding rSPD(n/CRD) nucleic acids, fragments, homologues, variants or derivatives thereof may be introduced into host cells for the purpose of replicating the vectors/polynucleotides and/or expressing the polypeptides encoded by the polynucleotides. Although the polypeptides may be produced using prokaryotic cells as host cells, it is preferred to use eukaryotic cells, for example yeast, insect or mammalian cells, in particular mammalian cells.

Vectors/polynucleotides may be introduced into suitable host cells using a variety of techniques known in the art, such as transfection, transformation and electroporation. Where vectors/polynucleotides are to be administered to animals, several techniques are known in the art, for example infection with recombinant viral vectors such as retroviruses, herpes simplex viruses and adenoviruses, direct injection of nucleic acids and biolistic transformation.

Protein Expression and Purification

Host cells comprising polynucleotides may be used to express polypeptides, such as rSPD(n/CRD) polypeptides, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Polypeptides can be extracted from host cells by a variety of techniques known in the art, including enzymatic, chemical and/or osmotic lysis and physical disruption.

Polypeptides may also be produced recombinantly in an in vitro cell-free system, such as the TnT™ (Promega) rabbit reticulocyte system.

Antibodies

The invention also provides monoclonal or polyclonal antibodies to polypeptides or fragments thereof. Thus, the present invention further provides a process for the production of monoclonal or polyclonal antibodies to an rSPD(n/CRD) polypeptide, fragment, homologue, variant or derivative thereof.

If polyclonal antibodies are desired, a selected mammal (e.g., mouse, rabbit, goat, horse, etc.) is immunised with an immunogenic polypeptide bearing an epitope(s) from a polypeptide. Serum from the immunised animal is collected and treated according to known procedures. If serum containing polyclonal antibodies to an epitope from a polypeptide contains antibodies to other antigens, the polyclonal antibodies can be purified by immunoaffinity chromatography. Techniques for producing and processing polyclonal antisera are known in the art. In order that such antibodies may be made, the invention also provides polypeptides or fragments thereof haptenised to another polypeptide for use as immunogens in animals or humans. Monoclonal antibodies directed against epitopes in the polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes in the polypeptides can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

Antibodies, both monoclonal and polyclonal, which are directed against epitopes from polypeptides are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the agent against which protection is desired.

Techniques for raising anti-idiotype antibodies are known in the art. These anti-idiotype antibodies may also be useful in therapy.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies may be used in method of detecting polypeptides present in biological samples by a method which comprises: (a) providing an antibody; (b) incubating a biological sample with said antibody under conditions which allow for the formation of an antibody-antigen complex; and (c) determining whether antibody-antigen complex comprising said antibody is formed. Suitable samples include extracts tissues such as brain, breast, ovary, lung, colon, pancreas, testes, liver, muscle and bone tissues or from neoplastic growths derived from such tissues.

Antibodies may be bound to a solid support and/or packaged into kits in a suitable container along with suitable reagents, controls, instructions and the like.

Assays

We disclose assays that are suitable for identifying substances which bind to rSPD(n/CRD) polypeptides, or fragments, homologues, variants or derivatives thereof.

In general, such binding assays involve exposing a rSPD(n/CRD) polypeptide, nucleic acid, or a fragment, homologue, variant or derivative thereof to a candidate molecule and detecting an interaction or binding between the rSPD(n/CRD) polypeptide, nucleic acid, or a fragment, homologue, variant or derivative thereof and the candidate molecule. The binding assay may be conducted in vitro, or in vivo.

We disclose assays for identifying substances which are capable of potentiating the activities of rSPD(n/CRD) polypeptide. Such compounds may be employed as agonists of rSPD(n/CRD) polypeptide, and may for example be co-administered to an individual to enhance any desired effect.

In general, an assay to identify such substances or compounds involves providing a cell or organism, exposing the cell or organism to a rSPD(n/CRD) polypeptide, nucleic acid, or a fragment, homologue, variant or derivative thereof, exposing the cell to a candidate molecule, and detecting an effect associated with rSPD(n/CRD). Any rSPD(n/CRD) polypeptide mediated effect, as disclosed in this document, particularly the Examples, may be detected.

In particular, the rSPD(n/CRD) polypeptide mediated effect is preferably chosen from the group consisting of: reduction of peripheral blood eosinophilia, reduction of serum IgB levels, reduction of serum IgG1 levels, reduction in airway hyperresponsiveness, reduction in alveolar macrophage number, reduction of phospholipid levels in lavage, down-regulation of Eotaxin expression, reduction in MCP-1 expression, down-regulation of MIP-1α expression, and down-regulation of MIP-2 expression.

In order to identify agonists, an additive or preferably synergistic effect is detected. Thus, while rSPD(n/CRD) polypeptide on its own is, for example, capable of reducing a level or number, or down-regulation of expression of a molecule, the assays identify molecules which further reduce the level, number or further down-regulate the expression of a molecule. Thus, preferably, the candidate molecule in conjunction with the rSPD(n/CRD) polypeptide, nucleic acid, or a fragment, homologue, variant or derivative thereof, down-regulates the expression of, or reduces the level or number, by more than 10%, more than 20%, more than 30%, more than 40%, more than 50%, more than 60%, more than 70%, more than 80%, more than 90%, or more compared to an rSPD(n/CRD) polypeptide on its own. Thus, for example, a candidate molecule suitable for use as an agonist is one which is capable of enhancing by 10% more the reduction of alveolar macrophage number achieved by rSPD(n/CRD) polypeptide on its own.

Conversely, assays to identify antagonists involve the detection of a reduction in rSPD(n/CRD) polypeptide mediated effect. Preferably, the down-regulation of expression or reduction in number or level achieved by rSPD(n/CRD) polypeptide is reduced in the presence of a suitable candidate molecule. Preferably, the reduction is at least 10%, preferably at least 20%, preferably at least 30%, preferably at least 40%, preferably at least 50%, preferably at least 60%, preferably at least 70%, preferably at least 80%, preferably at least 90%, or more compared to an rSPD(n/CRD) polypeptide on its own. Thus, for example, a candidate molecule suitable for use as an antagonist is one which is capable of reducing by 10% more the reduction of alveolar macrophage number achieved by rSPD(n/CRD) polypeptide on its own.

As an illustration, if N1 is the number of alveolar macrophages in an untreated organism, and N2 the number in an organism exposed to rSPD(n/CRD) polypeptide, nucleic acid, or a fragment, homologue, variant or derivative thereof, the alveolar macrophage number is decreased by $R=(N1-N2)/N1\times 100\%$. Agonists increase R, by a factor x, where x is greater than 1 (e.g., x=1, 1.1, 1.2, 1.3, 1.4, 1.5, 2, 3, 4, 5, 10, 20, 50, 100 etc); while antagonists decrease R, by a factor x, where x is less than 1 (e.g., x=0.9, 0.9, 0.7, 0.6, 0.5, 0.4, 0.3, 0.2, 0.1 etc).

For example, an organism may be exposed to a rSPD(n/CRD) polypeptide, nucleic acid, or a fragment, homologue, variant or derivative thereof and a candidate molecule, and the peripheral eosinophil level, or serum IgE or serum IgG1, or any combination, detected. Detection of airway hyperresponsiveness, or alvelar macrophage numbers, of an organism exposed to an rSPD(n/CRD) polypeptide, nucleic acid, or a fragment, homologue, variant or derivative thereof, together with a candidate molecule, may also be detected.

Preferred candidate molecules are those which provide an additive or synergistic effect in combination with rSPD(n/CRD).

Also disclosed are assays to identify antagonists of rSPD (n/CRD) polypeptide. Such assays involve detecting a reduced effect on exposure of a cell or organism to an rSPD (n/CRD) polypeptide, nucleic acid, or a fragment, homologue, variant or derivative thereof in conjunction with a candidate molecule.

In a preferred embodiment, the assays are conducted on whole organisms rather than cells. Preferably, the organism is one which suffers from a disease as disclosed in this document, or exhibits one or more symptoms of such a disease. In a highly preferred embodiment, the organism is one which does not express surfactant protein D. Preferably, such an organism comprises a disrupted or deleted SP-D gene. More preferably, the organism is a mouse (*Mus musculus*), preferably a SP-D knock-out mouse, made as described in Botas, C. et al., 1998, *Altered surfactant homeostasis and alveolar type II cell morphology in mice lacking surfactant protein D*. Proc. Natl. Acad. Sci. USA 95(20):11869-74.

Candidate Molecules

Suitable candidate molecules for use in the above assays include peptides, especially of from about 5 to 30 or 10 to 25 amino acids in size. Peptides from panels of peptides comprising random sequences or sequences which have been varied consistently to provide a maximally diverse panel of peptides may be used.

Suitable candidate molecules also include antibody products (for example, monoclonal and polyclonal antibodies, single chain antibodies, chimeric antibodies and CDR-grafted antibodies). Furthermore, combinatorial libraries, peptide and peptide mimetics, defined chemical entities, oligonucleotides, and natural product libraries may be screened for activity. The candidate molecules may be used in an initial screen in batches of, for example 10 types of molecules per reaction, and the molecules of those batches which show enhancement or reduction of a rSPD(n/CRD) polypeptide mediated effect tested individually.

Libraries

Libraries of candidate molecules, such as libraries of polypeptides or nucleic acids, may be employed in the methods and compositions described here. Such libraries are exposed a cell or organism in the presence of a rSPD(n/CRD) polypeptide, nucleic acid, or a fragment, homologue, variant or derivative thereof, and an rSPD(n/CRD) polypeptide mediated effect detected.

Selection protocols for isolating desired members of large libraries are known in the art, as typified by phage display techniques. Such systems, in which diverse peptide sequences are displayed on the surface of filamentous bacteriophage (Scott and Smith, 1990, supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of *E. coli* and as a result the resultant antibody fragments are displayed on the surface of the bacteriophage, typically as fusions to, bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al., 1990, supra; Kong et al., 1991, Proc. Nail. Acad. Sci. USA 88:4363; Clackson et al., 1991, Nature 352:624; Lowman et al., 1991, Biochemistry 30:10832; Burton et al., 1991, *Proc. Natl. Acad. Sci. USA* 88:10134; Hoogenboom et aL, 1991, Nucleic Acids Res. 19:4133; Chang et al., 1991, *J. Immunol.* 147:3610; Breitling et al., 1991, *Gene* 104:147; Marks et al., 1991, supra; Barbas et al., 1992, supra; Hawkins and Winter, 1992, *J. Immunol.* 22:867; Marks et al., 1992, *J. Biol. Chem.* 267:16007; Lerner et al., 1992, *Science* 258:1313, incorporated herein by reference). Such techniques may be modified if necessary for the expression generally of polypeptide libraries.

One particularly advantageous approach has been the use of scFv phage-libraries (Bird, R. E. et al., 1988, *Science* 242:423-6, Huston et al., 1988, Proc. Natl. Acad. Sci. USA 85:5879-5883; Chaudhary et al., 1990, Proc. Natl. Acad. Sci. USA 87:1066-1070; McCafferty et al., 1990, supra; Clackson et al., 1991, supra; Marks et al., 1991, supra; Chiswell et al., 1992, Trends Biotech. 10:80; Marks et al., 1992, supra).

Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described and are of use in the invention. These expression systems may be used to screen a large number of different members of a library, in the order of about $10^6$ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification. A similar technique may be used to identify DNA sequences which bind a predetermined human transcription factor (Thiesen and Bach, 1990, *Nucleic Acids Res.* 18:3203; Beaudry and Joyce, 1992, *Science* 257:635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randomly selected subunits. Combinatorial libraries may be screened for molecules which are capable of potentiating, enhancing, reducing or minimising the a rSPD(n/CRD) polypeptide mediated effect when exposed to a cell or organism.

Various combinatorial libraries of chemical compounds are currently available, including libraries active against proteolytic and non-proteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson, 1999, *Journal of Combinatorial Chemistry Vol* 1 No 4:235-282. Reference is also made to *Combinatorial peptide library protocols* (edited by Shmuel Cabilly, Totowa, N.J. Humana Press, c1998, *Methods in Molecular Biology*, v. 87).

Further references describing chemical combinatorial libraries, their production and use include The Chemical Generation of Molecular Diversity, Pavia, Michael R., Sphinx Pharmaceuticals, A Division of Eli Lilly (Published Jul. 1995); Combinatorial Chemistry: A Strategy for the Future—MDL Information Systems discusses the role its Project Library plays in managing diversity libraries (Published Jul. 1995); Solid Support Combinatorial Chemistry in Lead Discovery and SAR Optimization, Mjalli, Andan M. M. and Barry E. Toyonaga, Ontogen Corporation (Published Jul. 1995); Non-Peptidic Bradykinin Receptor Antagonists From a Structurally Directed Non-Peptide Library, Chakravarty, Sarvajit, Babu J. Mavunkel, Robin Andy, and Donald J. Kyle*, Scios Nova Inc. (Published Jul. 1995); Combinatorial Chemistry Library Design using Pharmacophore Diversity, Davies, Keith and Clive Briant, Chemical Design Ltd. (Published Jul. 1995); A Database System for Combinatorial Synthesis Experiments, James, Craig and David Weininger, Daylight Chemical Information Systems, Inc. (Published Jul. 1995); An Information Management Architecture for Combinatorial Chemistry, Davies, Keith and Catherine White, Chemical Design Ltd. (Published Jul. 1995); Novel Software Tools for Addressing Chemical Diversity, Pearlman, R. S., Laboratory for Molecular Graphics and Theoretical Modeling, College of Pharmacy, University of Texas (Published Jun./Jul. 1996); Opportunities for Computational Chemists Afforded by the New Strategies in Drug Discovery An Opinion, Connolly Martin, Yvonne, Computer Assisted Molecular Design Project, Abbott Laboratories (Published Jun./Jul. 1996); Combinatorial Chemistry and Molecular Diversity Course at the University of Louisville: A Description, Spatola, Arno F., Department of Chemistry, University of Louisville (Published Jun./Jul. 1996); Chemically Generated Screening Libraries: Present and Future, Pavia, Michael R., Sphinx Pharmaceuticals, A Division of Eli Lilly (Published Jun./Jul. 1996); Chemical Strategies For Introducing Carbohydrate Molecular Diversity Into The Drug Discovery Process, Sofia, Michael J., Transcell Technologies Inc. (Published Jun./Jul. 1996); Data Management for Combinatorial Chemistry, Zaborowski, Maryjo, Chiron Corporation and Sheila H. DeWitt, Parke-Davis Pharmaceutical Research, Division of Warner-Lambert Company (Published Nov. 1995); and The Impact of High Throughput Organic Synthesis on R&D in Bio-Based Industries, Devlin, John P. (Published Mar. 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the "bead" which interacts with the macromolecular target, and determination of the structure carried by the identified "bead" (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities). Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Candidate Substances

Suitable candidate substances include peptides, especially of from about 5 to 30 or 10 to 25 amino acids in size, based on the sequence of the polypeptides described in the Examples, or variants of such peptides in which one or more residues have been substituted. Peptides from panels of peptides comprising random sequences or sequences which have been varied consistently to provide a maximally diverse panel of peptides may be used.

Suitable candidate substances also include antibody products (for example, monoclonal and polyclonal antibodies, single chain antibodies, chimeric antibodies and CDR-grafted antibodies) which are specific for a polypeptide. Furthermore, combinatorial libraries, peptide and peptide mimetics, defined chemical entities, oligonucleotides, and natural product libraries may be screened for activity as inhibitors of binding of a polypeptide to the cell division cycle machinery, for example mitotic/meiotic apparatus (such as microtubules). The candidate substances may be used in an initial screen in batches of, for example 10 substances per reaction, and the substances of those batches which show inhibition tested individually. Candidate substances which show activity in in vitro screens such as those described below can then be tested in whole cell systems, such as mammalian cells which will be exposed to the inhibitor and tested for inhibition of any of the stages of the cell cycle.

Polypeptide Binding Assays

One type of assay for identifying substances that bind to a polypeptide involves contacting a polypeptide, which is immobilised on a solid support, with a non-immobilised candidate substance determining whether and/or to what extent the polypeptide and candidate substance bind to each other. Alternatively, the candidate substance may be immobilised and the polypeptide non-immobilised. This may be used to detect substances capable of binding to rSPD(n/CRD) polypeptides, or fragments, homologues, variants or derivatives thereof.

In a preferred assay method, the polypeptide is immobilised on beads such as agarose beads. Typically this is achieved by expressing the rSPD(n/CRD) polypeptide, or a fragment, homologue, variant or derivative thereof as a GST-fusion protein in bacteria, yeast or higher eukaryotic cell lines and purifying the GST-fusion protein from crude cell extracts using glutathione-agarose beads (Smith and Johnson, 1988). As a control, binding of the candidate substance, which is not a GST-fusion protein, to the immobilised polypeptide is determined in the absence of the polypeptide. The binding of the candidate substance to the immobilised polypeptide is then determined. This type of assay is known in the art as a GST pulldown assay. Again, the candidate substance may be immobilised and the polypeptide non-immobilised.

It is also possible to perform this type of assay using different affinity purification systems for immobilising one of the components, for example Ni-NTA agarose and histidine-tagged components.

Binding of the rSPD(n/CRD) polypeptide, or a fragment, homologue, variant or derivative thereof to the candidate substance may be determined by a variety of methods well-known in the art. For example, the non-immobilised component may be labeled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, more preferably from 1 to 100 nmol/ml. In the case of antibodies, the final concentration used is typically from 100 to 500 μg/ml, more preferably from 200 to 300 μg/ml.

DNA Binding

When released from the nuclear environment, nucleic acid such as DNA can cause inflammation in the surrounding tissues. Although several DNA-binding proteins are known, the proteins or receptors that involve in the clearance of DNA from the lung and other tissues are not clearly established. The present inventors have discovered that SP-D binds effectively to DNA (and total RNA) of bacterial, bacteriophage and chromosomal origin.

Electron microscopy shows that recombinant fragment of rSPD(n/CRD) (rSPD(n/CRD)) can efficiently bind DNA. Although not wishing to be bound by theory, the inventors have determined that nucleotides, the building blocks of DNA, can compete with mannan for binding to rSPD(n/CRD), suggesting that this protein can bind DNA via its carbohydrate binding activity. In addition, the presence of a short collagen-like fragment in this recombinant fragment may also provide added ability for it to bind DNA, effectively. Furthermore, rSPD(n/CRD) competes with propidium iodide for the binding of DNA on apoptotic cells indicating that the protein binds to the DNA found on the surface of these cells. Recognition of DNA on the surface is likely to be one of the important modes of clearing the apoptotic cells from the lung.

Several applications for SP-D and fragments thereof, especially rSPD(n/CRD), are mediated via the DNA-binding properties of these molecules. For example:

1) Several diseases, many of which involve chronic bacterial, fungal and viral infection result in the accumulation of free nucleic acid in lung. Cystic fibrosis is one such disease, and persistent infection in lung occurs only after bacterial bio-film formation, which requires extracellular free DNA. Since native SP-D and rSPD(n/CRD) bind free DNA, these proteins enhance the clearance of DNA and minimize bio-film formation. The rSPD(n/CRD) also opsonizes many pulmonary microbes, and acts potently to reduce or eliminate pathogen colonization in cystic fibrosis patients.

2) SP-D and rSPD(n/CRD) can bind to DNA. Therefore, cells that contain DNA on their surfaces, such as apoptotic and necrotic cells, are also recognized by SP-D and rSPD(n/CRD). These facts provide a mechanistic explanation by which the inflammation-causing cells are recognized by the rSPD(n/CRD) for phagocyte-mediated clearance, in vivo. SP-D and fragments thereof can be used to treat lung diseases and conditions such as COPD, chronic inflammation and chronic asthma.

3) Free DNA or DNA debris from necrotic and apoptotic cells can act as an autoantigen. Therefore, rSPD(n/CRD), in producing clearance of free DNA (or RNA) helps in reducing autoantibody production in autoimmune diseases.

Inflammatory Diseases

The term "inflammation" is used here to refer to the response of living tissue to damage. An rSPD(n/CRD) polypeptide, fragment, homologue, variant or derivative thereof may be used to treat inflammation, including an inflammatory disease, by administering an individual suffering from such a disease with the rSPD(n/CRD) polypeptide, fragment, homologue, variant or derivative thereof.

The causes of inflammation include physical damage, chemical substances, microorganisms or other agents. In a preferred embodiment, the rSPD(n/CRD) polypeptide, fragment, homologue, variant or derivative thereof is used to treat an inflammatory disease, although it may be used to treat any inflammation resulting from any cause.

The inflammatory response consists of changes in blood flow, increased permeability of blood vessels and escape of cells from the blood into the tissues. Acute inflammation is short-lasting, lasting only a few days. If it is longer lasting however, then it is referred to as chronic inflammation. Various examples of acute inflammation that you may be aware of are sore throat, reactions in the skin to a scratch or a burn or insect bite, and acute hepatitis and so on. However, there are occasional historical exceptions such as pneumonia, inflammation of the lung rather than pneumonitis and pleurisy, inflammation of the pleura, rather than pleuritis.

Microbial Infections

Viruses lead to death of individual cells by intracellular multiplication. Bacteria release specific exotoxins—chemicals synthesised by them which specifically initiate inflammation or endotoxins, which are associated with their cell walls. Additionally, some organisms cause immunologically-mediated inflammation through hypersensitivity reactions. Parasitic infections and tuberculous inflammation are instances where hypersensitivity is important.

Hypersensitivity Reactions

A hypersensitivity reaction occurs when an altered state of immunological responsiveness causes an inappropriate or excessive immune reaction which damages the tissues. All have cellular or chemical mediators similar to those involved in inflammation.

Physical Agents

Tissue damage leading to inflammation may occur through physical trauma, ultraviolet or other ionising radiation, burns or excessive cooling ("frostbite").

Irritant and Corrosive Chemicals

Corrosive chemicals (acids, alkalis, oxidising agents) provoke inflammation through gross tissue damage. However, infecting agents may release specific chemical irritants which lead directly to inflammation.

Inflammation typically involves at least one of the following features:

Tissue necrosis: Death of tissues from lack of oxygen or nutrients resulting from inadequate blood flow (infarction) is a potent inflammatory stimulus. The edge of a recent infarct often shows an acute inflammatory response. Redness (rubor): An acutely inflamed tissue appears red, for example skin affected by sunburn, cellulitis due to bacterial infection or acute conjunctivitis. This is due to dilatation of small blood vessels within the damaged area. Heat (calor): Increase in temperature is seen only in peripheral parts of the body, such as the skin. It is due to increased blood flow (hyperaemia) through the region, resulting in vascular dilatation and the delivery of warm blood to the area. Systemic fever, which results from some of the chemical mediators of inflammation, also contributes to the local temperature. Swelling (tumor): Swelling results from oedema, the accumulation of fluid in the extra vascular space as part of the fluid exudate, and to a much lesser extent, from the physical mass of the inflammatory cells migrating into the area. Pain (dolor): For the patient, pain is one of the best known features of acute inflammation. It results partly from the stretching and distortion of tissues due to inflammatory oedema and, in particular, from pus under pressure in an abscess cavity. Some of the chemical mediators of acute inflammation, including bradykinin, the prostaglandins and serotonin, are known to induce pain. Loss of function: Movement of an inflamed area is consciously and reflexly inhibited by pain, while severe swelling may physically immobilise the tissues.

Thus, we provide for the alleviation of a symptom of inflammation, including a symptom as listed above, by the administration of an rSPD(n/CRD) polypeptide, fragment, homologue, variant or derivative thereof to an individual suffering from inflammation or an inflammatory disease.

Inflammatory Lung Disease

In a highly preferred embodiment, a rSPD(n/CRD) polypeptide, fragment, homologue, variant or derivative thereof is used to treat an inflammatory lung disease.

As the term is used here, "inflammatory lung disease" should be taken to mean any disease or condition which involves inflammation of the lung, or any portion of the lung or associated systems such as the airway, trachea etc. The inflammatory lung disease may be acute or chronic, and may a result of or be accompanied by some other disease or syndrome. In a preferred embodiment, the inflammatory lung disease comprises a chronic inflammatory lung disease.

Examples of inflammatory lung diseases include neonatal chronic lung disease, neonatal respiratory distress syndrome (RDS), adult respiratory distress syndrome, chronic obstructive airways disease (COPD), asthma, cystic fibrosis, pulmonary fibrosis, emphysema, interstitial inflammatory lung disease, sarcoidosis, pneumonia, chronic inflammatory lung disease, neonatal chronic inflammatory lung disease.

Individuals suffering from such diseases may be treated by, or their symptoms relieved, by administration of a rSPD(n/CRD) polypeptide, fragment, homologue, variant or derivative thereof to the individual. Preferably, such treatment results in the clearance of alveolar macrophages, preferably apoptotic alveolar macrophages. Treatment may also further or in the alternative result in clearance of necrotic macrophages. Necrotic and apoptotic cells may be detected and distinguished by the assays as set out below.

Neonatal Chronic Lung Disease

Neonatal chronic lung disease is a multifactorial condition associated with recurrent inflammation and infection after premature birth. There are a number of factors carrying an increased risk of developing chronic lung disease including premature birth, prolonged ventilation, recurrent infection in the neonatal period, surfactant deficiency and increased inflammatory markers in the neonatal period, including the number of alveolar macrophages in tracheal suction samples. Premature infants are known to be deficient in surfactant proteins including SP-D.

Human neonatal chronic lung disease arises out of inflammatory damage and oxidative stress after prolonged assisted ventilation, typically after premature birth. Survival after premature birth has increased dramatically since the advent of artificial surfactant replacement therapy for the treatment of neonatal respiratory distress syndrome, but up to 40% of infants surviving after birth at less than 28 weeks gestation develop chronic inflammatory lung disease. Current surfactant replacement strategies do not include surfactant protein D. Lung damage in this setting is mediated by activated alveolar macrophages. SP-D deficient mice provide a model for macrophage mediated inflammation in the lung characterised by the presence of large numbers of activated alveolar macrophages.

We demonstrate in the Examples that intranasal administration of rSP-D(N/CRD) to SP-D deficient mice modulates the inflammatory process in the lungs by decreasing the number of activated macrophages and altering their phenotype. The results demonstrate a potent anti-inflammatory property of rSP-D(N/CRD) and indicate a direct clinical application of rSP-D(N/CRD) in the prevention of chronic inflammatory lung disease in neonates by direct administration or by including rSP-D(N/CRD) in the formulation of current surfactant therapies. Nucleic acids encoding rSPD(n/CRD), as well as fragments, homologues, variants and derivatives may also be employed. Chronic lung inflammation causing emphysema (e.g. in smokers, deficient in natural levels of SP-D) may also be treatable by administration of rSP-D(N/CRD).

We therefore provide for the treatment of neonatal chronic lung disease, or any symptom of such a disease, by the administration of an rSPD(n/CRD) polypeptide, fragment, homologue, variant or derivative thereof.

Surfactant Replacement Therapy

This section describes Surfactant Replacement Therapy, for which the rSPD(n/CRD) polypeptide, nucleic acid, or a fragment, homologue, variant or derivative thereof disclosed here are suitably used. In particular, the rSPD(n/CRD) polypeptide, nucleic acid, or a fragment, homologue, variant or derivative thereof may be employed for surfactant replacement therapy in the neonate.

Surfactant Replacement Therapy is described in detail in Respir. Care, 1994, 39(8):824-829, from which this section is derived. Guidelines for Surfactant Replacement Therapy have been issued, for example, the AARC Clinical Practice Guidelines. A clinician following such guidelines will be able to administer rSPD(n/CRD) polypeptide, nucleic acid, or a fragment, homologue, variant or derivative thereof as part of a programme of surfactant replacement therapy.

Natural, endogenous surfactant is a compound composed of phospholipids, neutral lipids, and proteins (1-5) that forms a layer between the alveolar surface and the alveolar gas and reduces alveolar collapse by decreasing surface tension within the alveoli. (3-5) Surfactant deficiency is almost always associated with the formation of hyaline membranes in the immature lung and the onset of respiratory distress syndrome (RDS)-a major cause of morbidity and mortality in premature infants. (3) Without surfactant, alveoli may never inflate or may collapse on expiration and require inordinate force to re-expand on inspiration, leading to the development of RDS. (3,5) The incidence of RDS is related more to lung immaturity than to gestational age. (6) However, in general, the more premature the infant, the less the surfactant production and the higher the probability for RDS. (4,6) Direct tracheal instillation of surfactant has been shown to reduce mortality and morbidity in infants with RDS. (7-25)

Surfactant can be extracted from animal lung lavage and from human amniotic fluid or produced from synthetic materials. According to the methods and compositions described here, rSPD(n/CRD) polypeptide, nucleic acid, or a fragment, homologue, variant or derivative thereof may be used for Surfactant Replacement Therapy, particulary in the neonate. rSPD(n/CRD) polypeptide, nucleic acid, or a fragment, homologue, variant or derivative thereof may be used alone, or in combination with known surfactant replacement therapies.

Two basic strategies for surfactant replacement have emerged: (1) prophylactic or preventive treatment in which surfactant is administered at the time of birth or shortly thereafter to infants who are at high risk for developing RDS and (2) rescue or therapeutic treatment in which surfactant is administered after the initiation of mechanical ventilation in infants with clinically confirmed RDS. (2,10-12,26,27).

Surfactant Replacement Therapy is typically administered by trained personnel in the delivery room or in a neonatal intensive care unit.

Indications for Surfactant Replacement Therapy 4.1 Prophylactic administration may be indicated in 4.1.1 infants at high risk of developing RDS because of short gestation (<32 weeks) (8,10-12,21,25-29) or low birth weight (<1,300 g), (21-25,28) which strongly suggest lung immaturity. 4.1.2 infants in whom there is laboratory evidence of surfactant deficiency such as lecithin/sphingomyelin ratio less than 2:1, (11,14,28,30,31) bubble stability test indicating lung immaturity, (15,32) or the absence of phosphatidylglycerol. (11,14,22-24,28,30) 4.2 Rescue or therapeutic administration is indicated in preterm or full-term infants 4.2.1 who require endotracheal intubation and mechanical ventilation because of 4.2.1.1 increased work of breathing as indicated by an increase in respiratory rate, substernal and suprasternal retractions, grunting, and nasal flaring. (8,11,14-16,29,33-35) 4.2.1.2 increasing oxygen requirements as indicated by pale or cyanotic skin color, agitation, and decreases in PaO2, SaO2, or SpO2 mandating an increase in FIO2 above 0. (4011,12,15,26,33,36-38) and 4.2.2 have clinical evidence of RDS, (13,39) including 4.2.2.1 chest radiograph characteristic of RDS, (8,11-16,33,34,36,37,40-42) 4.2.2.2 mean airway pressure greater than 7 cm H2O to maintain an adequate PaO2, SaO2, or SpO2. (11,14,15,26,43)

Contraindications

Surfactant Replacement Therapy is contraindicated for the following conditions: 5.1 the presence of congenital anomalies incompatible with life beyond the neonatal period, (8,14,15,26,28,29,31,33,36,41,44) 5.2 respiratory distress in infants with laboratory evidence of lung maturity. (9,14,27-29,33,36,41)

Hazards and complications arising from Surfactant Replacement Therapy include: 6.1 Procedural complications resulting from the administration of surfactant include 6.1.1 plugging of endotracheal tube (ETT) by surfactant; (2) 6.1.2 hemoglobin desaturation and increased need for supplemental O2; (11,33,41) 6.1.3 bradycardia due to hypoxia; (9,33,41,45) 6.1.4 tachycardia due to agitation, with reflux of surfactant into the ETT; (34,41 6.1.5 pharyngeal deposition of surfactant; 6.1.6 administration of surfactant to only one lung; 6.1.7 administration of suboptimal dose secondary to miscalculation or error in reconstitution. 6.2 Physiologic complications of surfactant replacement therapy include 6.2.1 apnea, (7,13,15) 6.2.2 pulmonary hemorrhage, (12,15,18,32,34,38,46,47 6.2.3 mucus plugs, (48) 6.2.4 increased necessity for treatment for PDA, (18,29,30 6.2.5 marginal increase in retinopathy of prematurity, (11) 6.2.6 barotrauma resulting from increase in lung compliance following surfactant replacement and failure to change ventilator settings accordingly. (30,49)

Surfactant administered prophylactically may be given to some infants in whom RDS would not have developed. (10,12,26,33) When surfactant is administered prophylactically in the delivery room, ETT placement may not have been verified by chest radiograph resulting in the inadvertent administration to only one lung or to the stomach. (26) Prophylactic surfactant administration may delay patient stabilization. (26) Atelectasis and lung injury may occur prior to therapeutic administration. (26,33) Tracheal suctioning should be avoided following surfactant administration. (9,11,13,14,27,33,38,44,50) Not all infants who are treated with a single dose of surfactant experience a positive response 39 or the response may be transient. Positioning recommended for surfactant administration may further compromise the unstable infant. (9,11,12,14,16,28,33,38-40)

A clinician may undertake an assessment of need to determine that valid indications are present. The following are typically done for this: 8.1 Assess lung immaturity prior to prophylactic administration of surfactant by gestational age and birth weight and/or by laboratory evaluation of tracheal or gastric aspirate. 8.2 Establish the diagnosis of RDS by chest radiographic criteria and the requirement for mechanical ventilation in the presence of short gestation and/or low birth weight. Assessment of outcome is conducted according to the following: 9.1 Reduction in FIO2 requirement (12,33,34,36-39,41,44) 9.2 Reduction in work of breathing (51) 9.3 Improvement in lung volumes and lung fields as indicated by chest radiograph (13,16,33,40) 9.4 Improvement in pulmonary mechanics (e.g., compliance, airways resistance, VT, VE, transpulmonary pressure) and lung volume (i.e., FRC) (42,43,50,52-59) 9.5 Reduction in ventilator requirements (PIP, PEEP, Paw) (2,8,9,12,13,27,30,33,36-39,41,44,50,52) 9.6 Improvement in ratio of arterial to alveolar PO2 (a/A PO2), oxygen index. (13,16,28,30,33,34,37-41,44)

Resources

Administration procedures recommended for specific preparations of surfactant should be adhered to. 10.1 Equipment (10-14,16,26-28,33,34,39,40,50,60) 10.1.1 Administration equipment 10.1.1.1 Syringe containing the ordered dose of surfactant, warmed to room temperature (11,12,16,38,40) 10.1.1.2 5-Fr feeding tube or catheter, or endotracheal tube connector with delivery port 10.1.1.3 Mechanical ventilator or manual ventilator (resuscitation bag) (8,16,33,36,38-40,44,50,52) 10.1.2 Resuscitation equipment 10.1.2.1 Laryngoscope and endotracheal tube (10-12,14,16,26,38) 10.1.2.2 Manual resuscitation bag (9-12,16,26-28,36,39,40,50) and airway manometer 10.1.2.3 Blended oxygen source (9,16,28,44) 10.1.2.4 Suction equipment (i.e., catheters, sterile gloves, collecting bottle and tubing, and vacuum generator) (9,33,50,60) 10.1.2.5 Radiant warmer ready for use 10.1.3 Monitoring equipment 10.1.3.1 Neonatal tidal volume monitor if available (50) 10.1.3.2 Airway pressure monitor 10.1.3.3 Pulse oximeter or transcutaneous PCO2 monitor (11,26,34,39-41,52) 10.1.3.4 Cardiorespiratory monitor 10.2 Personnel—Surfactant replacement therapy should be performed under the direction of a physician by credentialed personnel (e.g., CRTT, RRT, RN) who competently demonstrate 10.2.1 proper use, understanding, and mastery of the equipment and technical aspects of surfactant replacement therapy; 10.2.2 comprehensive knowledge and understanding of neonatal ventilator management and pulmonary anatomy and pathophysiology; 10.2.3 neonatal patient assessment skills, including the ability to recognize and respond to adverse reactions and/or complications of the procedure; 10.2.4 knowledge and understanding of the patient's history and clinical condition; 10.2.5 knowledge and understanding of airway management, 10.2.6 ability to interpret monitored and measured blood gas variables and vital signs; 10.2.7 proper use, understanding, and mastery of emergency resuscitation equipment and procedures; 10.2.8 ability to evaluate and document outcome (Section 9.0); 10.2.9 understanding and proper application of Universal Precautions.

Monitoring

The following should be monitored as part of surfactant replacement therapy. 11.1 Variables to be monitored during surfactant administration 11.1.1 Proper placement and position of delivery device 11.1.2 FIO2 and ventilator settings (8,9,11,13-15,27-29,33,36,38,44) 11.1.3 Reflux of surfactant into ETT (34,41) 11.1.4 position of patient (i.e., head direction) (9,11,33) 11.1.5 Chest-wall movement (6 1) 11.1.6 Oxygen saturation by pulse oximetry (11,26,34,39-41,52) 11.1.7 Heart rate, respirations, chest expansion, skin color, and vigor (16,26,27,34,41,45, 52) 11.2 Variables to be monitored after surfactant administration 11.2.1 Invasive and noninvasive measurements of arterial blood gases (8,9,11,12-16,26-29, 33,36,38,39,41,44) 11.2.2 Chest radiograph (11-16,28,36, 38-40,44) 11.2.3 Ventilator settings (PIP, PEEP, Paw) and FIO2 (8,9,11,13-16,28,29,33,36,38) 11.2.4 Pulmonary mechanics and volumes 11.2.5 Heart rate, respirations, chest expansion, skin color, and vigor (16,26,27,34,41,45,52) 11.2.6 Breath sounds (11,38) 11.2.7 Blood pressure 1. (3,16, 33,40,44,45)

Frequency

Repeat doses of surfactant are contingent upon the continued diagnosis of RDS. The frequency with which surfactant replacement is performed should depend upon the clinical status of the patient and the indication for performing the procedure. Additional doses of surfactant, given at 6- to 24-hour intervals, may be indicated in infants who experience increasing ventilator requirements or whose conditions fail to improve after the initial dose. (7,9,11,12,14,15,26,30,34,37, 39,52)

Infection Control 13.1 Universal Precautions (62) should be implemented. 13.2 Aseptic technique should be practiced. 13.3 Appropriate infection control guidelines for the patient should be posted and followed.

Cystic Fibrosis

We show in the Examples that rSPD(n/CRD) polypeptide is capable of reducing alveolar macrophage number. Accordingly, rSPD(n/CRD) polypeptide, nucleic acid, or a fragment, homologue, variant or derivative thereof may be administered in lung diseases in which alveolar macrophages play a role in the inflammatory process, for example, cystic fibrosis, asthma and emphysema. rSP-D (N/CRD) also has therapeutic properties in macrophage mediated inflammatory processes at other sites, e.g. in atherosclerosis.

Cystic fibrosis is a genetic disease affecting approximately both children and adults.

Cystic fibrosis causes the body to produce an abnormally thick, sticky mucus, due to the faulty transport of sodium and chloride (salt) within cells lining organs such as the lungs and pancreas, to their outer surfaces. The thick cystic fibrosis mucus also obstructs the pancreas, preventing enzymes from reaching the intestines to help break down and digest food.

Cystic fibrosis has a variety of symptoms. The most common are: very salty-tasting skin; persistent coughing, wheezing or pneumonia; excessive appetite but poor weight gain; and bulky stools. The sweat test is the standard diagnostic test for cystic fibrosis, which measures the amount of salt in the sweat. A high salt level indicates that a person has cystic fibrosis.

The treatment of cystic fibrosis depends upon the stage of the disease and which organs are involved. One means of treatment, chest physical therapy, requires vigorous percussion (by using cupped hands) on the back and chest to dislodge the thick mucus from the lungs. Antibiotics are also used to treat lung infections and are administered intravenously, via pills, and/or medicated vapors which are inhaled to open up clogged airways. When cystic fibrosis affects the digestive system, the body does not absorb enough nutrients. Therefore, people with cystic fibrosis may need to eat an enriched diet and need to take both replacement vitamins and enzymes.

According to the methods and compositions described here, a symptom of a patient suffering from cystic fibrosis is alleviated by administration of rSPD(n/CRD) polypeptide, fragment, homologue, variant or derivative thereof. The symptom of cystic fibrosis preferably includes any of the symptoms listed above. Preferably, a patient suffering from cystic fibrosis is treated by administration of such a polypeptide, homologue, fragment or derivative.

Allergies

Existing treatments for allergies typically involve the long-term use of steroids to depress the immune system. There are undesirable side effects with long-term steroid therapy. We demonstrate that rSPD(n/CRD) polypeptide, nucleic acid, or a fragment, homologue, variant or derivative thereof may be used to alleviate the symptoms of allergy, or to treat allergy.

Treatment with rSPD(n/CRD) appears to have no ill effects in mice and is unlikely to generate unwanted side-effects in humans. A short treatment course with rSPD(n/CRD) can reverse the underlying allergic sensitisation leading to effective immunotherapy. This is a significant improvement on existing desensitisation immunotherapy protocols which typically involve a series of injections of allergen over a period of years.

Allergies suitable for treatment with rSPD(n/CRD) polypeptide, nucleic acid, or a fragment, homologue, variant or derivative thereof include a seasonal respiratory allergy, allergic rhinitis, hayfever, nonallergic rhinitis, vasomotor rhinitis, irritant rhinitis, an allergy against grass pollens, tree pollens or animal danders, an allergy associated with allergic asthma, and food allergies. In particular, and as described elsewhere, rSPD(n/CRD) polypeptide, nucleic acid, or a fragment, homologue, variant or derivative thereof may be used to treat allergies to house dust mite (*Dermatophagoides* spp), preferably *Dermatophagoides pteronyssinus* or *Dermatophagoides farinae*, or to fungi or fungal spores, preferably *Aspergillus fumigatus*. Preferably, the allergens are comprised in faeces of *Dermatophagoides* spp.

Asthma

Asthma is a respiratory condition characterized by episodes of airflow obstruction in the bronchial tubes. Symptoms caused by this obstruction include coughing, chest tightness, wheezing and shortness of breath. Although problems are often separated by symptom-free periods, asthma is a chronic illness.

A wide variety of "triggers" may initiate an episode of asthma. The most common triggers are allergens, aspirin and tartrazine, irritants, food additives and preservatives, viral respiratory infections and physical exertion.

Allergens are substances to which susceptible individuals may become allergic. They are a major source of problems in children and adults. Common allergens include plant pollen (tree, grass and weed), animal dander, house dust mites, molds and certain foods. When an allergic individual comes in contact with one of these allergens, a series of events causes the body to release certain chemicals (mediators), which then trigger asthma.

Ten to twenty percent of asthmatics experience a significant decrease in their lung function after taking aspirin; similar reactions can occur with a related group of medications called nonsteroidal anti-inflammatory agents and with tartrazine (yellow food dye #5). Cold air, smoke, industrial chemicals, perfume, paint and gasoline fumes are all examples of irritants that can provoke asthma, probably by stimulating irritant receptors in the respiratory tract. These receptors, in turn, cause the muscles surrounding the airway to constrict, resulting in an asthma attack. Rarely, food additives such as sulphites can trigger asthma. Viral respiratory infections are the leading cause of acute asthma attacks.

During an asthma attach, an asthmatic's hyperactive bronchial tubes narrow in response to certain triggers. During an attack, muscles surrounding the bronchial tubes contract, narrowing the air passages. Inflammation also occurs along the lining of the airways which produces swelling and further reduction of airway size. In addition, mucus glands along the inside of the air passages produce excess mucus which accumulates in the already narrowed air passages. The end result is that breathing, especially exhaling, becomes extremely difficult. Air becomes trapped behind the narrowed bronchial passages and there is a decrease in the oxygen available to the body.

Bronchodilators are the most commonly prescribed drugs to treat asthma. They relax the muscles surrounding the airways, resulting in dilation of the bronchial tubes. Bronchodilators may be inhaled, taken orally or injected. Cold, dry air, for example, inhaled during exercise through the mouth can also trigger asthma.

Current drugs used for treating the symptoms of asthma include long-acting theophyllines, inhaled or oral beta agonists, cromolyn and inhaled or oral steroids. For allergic asthmatics, immunotherapy (allergy shots) may offer relief from allergens that cannot be avoided. Immunotherapy increases a patient's tolerance to the allergens that prompt asthma symptoms.

Allergic Asthma

Asthma may also be triggered by exposure to allergens ("allergic asthma").

Allergic asthma is characterised by periods of airway hyperresponsiveness (AHR.) that occur in early phase and late phase hypersensitivity reactions in response to allergen provocation. The early phase response is mediated by the degranulation of airway mast cells with the release of histamine and other bronchoconstrictors. The late phase response begins after the influx of inflammatory cells such as eosinophils and lymphocytes and the subsequent release of inflammatory mediators and cytokines, which lead to chronic AHR.

House dust mite is one of the leading causes of allergic asthma (Platts-Mills, T. A. and M. D. Chapman, 1987, *Dust mites: immunology, allergic disease, and environmental control*, 3. Allergy Clin. Immunol. 80:755-75; Platts-Mills, T. A., E. B. Mitchell, M. D. Chapman, and P. W. Heymann, 1987, *Dust mite allergy: its clinical significance*, Hosp. Pract. (Off Ed) 22:91-3, 97-100; Pollart, S. M., M. D. Chapman, and T. A. Platts-Mills, 1987, *House dust sensitivity and environmental control*, Prim. Care. 14:591-603). An rSPD(n/CRD) polypeptide, fragment, homologue, variant or derivative thereof for example as described here, may be used to treat allergic asthma. Preferably, the rSPD(n/CRD) polypeptide, fragment, homologue, variant or derivative thereof is employed to treat allergy, or allergic asthma, caused by house dust mite.

House dust mite refers to any organisms of *Dermatophagoides* spp. Preferably, the *Dermatophagoides* organism is *Dermatophagoides pteronyssinus* or *Dermatophagoides farinae*. Allergic asthma may also develop as a result of exposure of an individual to fungi or fungal spores, and the methods and compositions described here include the treatment of such asthma or allergy, including allergy against *Aspergillus fumigatus* antigens.

Pulmonary Emphysema and Chronic Obstructive Pulmonary Disease

In a particular embodiment, an rSPD(n/CRD) polypeptide, fragment, homologue, variant or derivative thereof, for example as described here, is used to treat pulmonary emphysema or chronic obstructive pulmonary disease.

Emphysema is a massive public health problem for which there are no satisfactory treatments. Cigarette smoke induces alveolar macrophage apoptosis in vitro (Aoshiba, K., J. Tamaoki, and A. Nagai, 2001, *Acute cigarette smoke exposure induces apoptosis of alveolar macrophages*, Am. J. Physiol. Lung Cell. Mol. Physiol. 281:L1392) and in vivo (Aoshiba et al, supra) and Majo et al. has recently reported that apoptosis in lung tissue samples from smokers showed a bilinear relationship with the amount smoked, increasing sharply in smokers with emphysema and concludes that apoptosis might be one of the mechanisms of lung destruction leading to the development of emphysema Majo, J., H Ghezzo, and M. G. Cosio, 2001, *Lymphocyte population and apoptosis in the lungs of smokers and their relation to emphysema* Eur Respir J 17: 946. We propose that SP-D is deficient in smokers, and that this promotes apoptosis and contribute to emphysema in this patient group. We demonstrate that rSP-D(N/CRD) administration to SP-D deficient mice reduces apoptotic cell numbers; accordingly, rSP-D(N/CRD) therapy in humans can inhibit a mechanism contributing to emphysema provoked by cigarette smoking.

Cytokines

In a further embodiment, the rSPD(n/CRD) polypeptide, nucleic acid, fragment, homologue, variant or derivative thereof is used to modulate cytokine levels in an individual. Preferably, the level of inflammatory cytokines is down-regulated. Examples of inflammatory cytokines include Granulocyte-Macrophage-Colony stimulating factor (GM-CSF), as well as any cytokine that mediates migration of alveolar macrophages into the lung and act to increase cell proliferation.

Figure 14:
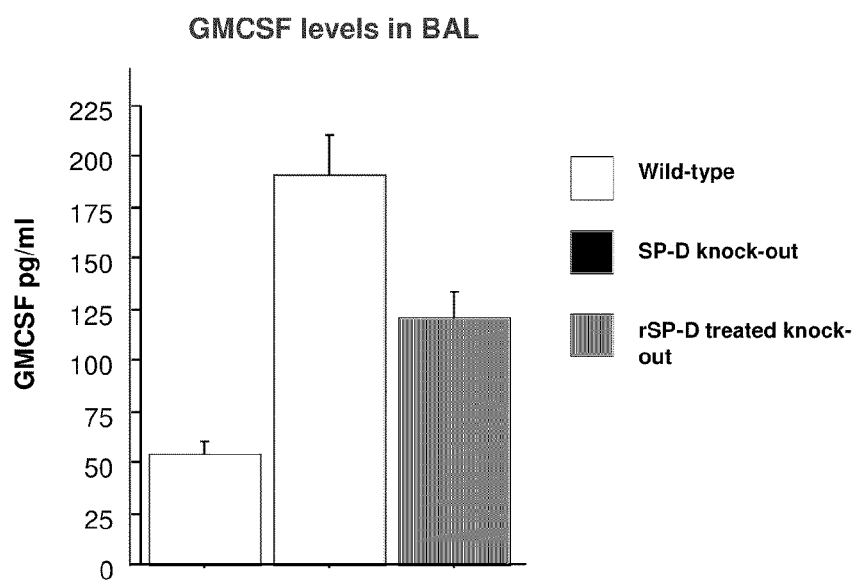
FIG. 14 is a graph showing GM-CSF concentrations in bronchoalveolar lavage of wild-type, SP-D knock-out mice and SP-D knock-out mice treated with rSPD(n/CRD).

Modulation of GM-CSF levels by administration of rSPD (n/CRD) polypeptide, nucleic acid, or a fragment, homologue, variant or derivative thereof is demonstrated in Example 9 (FIG. 14).

The term "cytokine" may be used to refer to any of a number of soluble molecules (e.g., glycoproteins) released by cells of the immune system, which act nonenzymatically through specific receptors to regulate immune responses. Cytokines resemble hormones in that they act at low concentrations bound with high affinity to a specific receptor. Preferably, the term "cytokine" refers to a diverse group of soluble proteins and peptides which act as humoral regulators at nano- to picomolar concentrations and which, either under normal or pathological conditions, modulate the functional activities of individual cells and tissues.

Particular examples of cytokines which are suitable for use in the methods and compositions described include interleukins, lymphokine, interferon, Colony Stimulating Factors (CSFs) such as Granulocyte-Colony Stimulating Factor (G-CSF), Macrophage-Colony stimulating factor (M-CSF) and Granulocyte-Macrophage-Colony stimulating factor (GM-CSF), GSF, Platelet-Activating Factors (PAF), Tumor Necrosis Factor (TNF). Thus, interleukins such as IL1, IL2 and IL4, as well as interferons such as IFN-$\alpha$, IFN-$\beta$ and IFN-$\gamma$ are included. Tumour necrosis factors TNF-$\alpha$ (cachetin), TNF-$\beta$ (lymphotoxin) may also be suitably employed.

Preferred cytokines are those which are capable of recruiting immune responses, for example, stimulation of dendritic cell or cytotoxic T cell activity, or which are capable of recruiting macrophages to the target site. In a highly preferred embodiment, the cytokine comprises IL-2, GM-CSF or GSF.

Apoptosis

According to the methods and compositions described here, administration of a rSPD(n/CRD) polypeptide, nucleic acid, or a fragment, homologue, variant or derivative thereof to an individual is capable of reducing the number of alveolar macrophages, in particular the number of apoptotic alveolar macrophages, or necrotic alveolar macrophages or both. Without seeming to be bound by a particular theory, we envisage that rSPD(n/CRD) polypeptide, nucleic acid, or a fragment, homologue, variant or derivative thereof achieves this by enhancing the clearance of apoptotic and/or necrotic macrophages for the body of the individual.

Preferably, treatment with rSPD(n/CRD) polypeptide, nucleic acid, or a fragment, homologue, variant or derivative thereof results in least 10% more clearance of apoptotic and/ or necrotic macrophages, preferably at least 20% more clearance. Most preferably, treatment with rSPD(n/CRD) polypeptide, nucleic acid, or a fragment, homologue, variant or derivative thereof results in at least 40%, 60%, 80% or more clearance of apoptotic and/or necrotic macrophages.

Cell death can occur by either of two distinct mechanisms, necrosis or apoptosis. In addition, certain chemical compounds and cells are said to be cytotoxic to the cell, that is, to cause its death.

"Necrosis" (also referred to as "accidental" cell death) refers to the pathological process which occurs when cells are exposed to a serious physical or chemical insult. Necrosis occurs when cells are exposed to extreme variance from physiological conditions (e.g., hypothermia, hypoxia) which may result in damage to the plasma membrane. Under physiological conditions direct damage to the plasma membrane is evoked by agents like complement and lytic viruses. Necrosis begins with an impairment of the cell's ability to maintain homeostasis, leading to an influx of water and extracellular ions. Intracellular organelles, most notably the mitochondria, and the entire cell swell and rupture (cell lysis). Due to the ultimate breakdown of the plasma membrane, the cytoplasmic contents including lysosomal enzymes are released into the extracellular fluid. Therefore, in vivo, necrotic cell death is often associated with extensive tissue damage resulting in an intense inflammatory response.

"Apoptosis" ("normal" or "programmed" cell death) refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies) which contain ribosomes, morphologically intact mitochondria and nuclear material. In vivo, these apoptotic bodies are rapidly recognised and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis".

Table 1 summarises the various observable differences between necrosis and apoptosis. Any of these differences, alone or in combination, may be assayed in order to determine whether cell death is occurring by apoptosis or by necrosis.

TABLE 1

Differential features and significance of necrosis and apoptosis.

| | Necrosis | Apoptosis |
|---|---|---|
| Morphological features | Loss of membrane integrity<br>Begins with swelling of cytoplasm and mitochondria<br>Ends with total cell lysis<br>No vesicle formation, complete lysis | Membrane blebbing, but no loss of integrity<br>Aggregation of chromatin at the nuclear membrane<br>Begins with shrinking of cytoplasm and condensation of nucleus<br>Ends with fragmentation of |

TABLE 1-continued

Differential features and significance of necrosis and apoptosis.

| | Necrosis | Apoptosis |
|---|---|---|
| | Disintegration (swelling) of organelles | cell into smaller bodies<br>Formation of membrane bound vesicles (apoptotic bodies)<br>Mitochondria become leaky due to pore formation involving proteins of the bcl-2 family. |
| Biochemical features | Loss of regulation of ion homeostasis<br>No energy requirement (passive process, also occurs at 4° C.)<br>Random digestion of DNA (smear of DNA after agarose gel electrophoresis)<br>Postlytic DNA fragmentation (=late event of death) | Tightly regulated process involving activation and enzymatic steps<br>Energy (ATP)-dependent (active process, does not occur at 4° C.)<br>Non-random mono- and oligonucleosomal length fragmentation of DNA (Ladder pattern after agarose gel electrophoresis)<br>Prelytic DNA fragmentation<br>Release of various factors (cytochrome C, AIF) into cytoplasm by mitochondria<br>Activation of caspase cascade<br>Alterations in membrane asymmetry (i.e., translocation of phosphatidyl-serine from the cytoplasmic to the extracellular side of the membrane) |
| Physiological significance | Affects groups of contiguous cells<br>Evoked by non-physiological disturbances (complement attack, lytic viruses, hypothermia, hypoxia, ischemica, metabolic poisons)<br>Phagocytosis by macrophages<br>Significant inflammatory response | Affects individual cells<br>Induced by physiological stimuli (lack of growth factors, changes in hormonal environment)<br>Phagocytosis by adjacent cells or macrophages<br>No inflammatory response |

Reference is made to the following documents, which describe apoptosis in detail, as well as various assays for measuring cell death by apoptosis: Schwartzman, R. A. and Cidlowski, J. A. (1993). Endocrine Rev. 14, 133; Vermes, I. and Haanan, C. (1994). Adv. Clin. Chem. 31, 177; Berke, G. (1991). Immunol. Today 12, 396; Krähenbühl, O. and Tschopp, J. (1991). Immunol. Today 12, 399; Van Furth, R. and Van Zwet, T. L. (1988). J. Immunol; Methods 108, 45. Cohen, J. J. (1993) Apoptosis. Immunol. Today 14, 126; Savill, J. S. et al. (1989). J. Clin. Invest. 83, 865; Wyllie, A. H. (1980). Nature 284, 555; Leist, M. et al. (1994) Biochemica No. 3, 18-20; Fraser, A. and Evan, G. (1996) Cell 85, 781-784; Duke, R. C. (1983). Proc. Natl. Acad. Sci. USA 80, 6361; Duke, R. C. & Cohen, J. J. (1986). Lymphokine Res. 5, 289; Trauth, B. C. et al. (1994) Eur. J. Cell. Biol. 63, 32, Suppl 40; Matzinger, P. (1991). J. Immunol; Methods 145, 185; Kaeck, M. R. (1993); Anal. Biochem. 208, 393; Prigent, P. et al. (1993). J. Immunol; Methods 160, 139; Huang, P. & Plunkett, W. (1992); Anal. Biochem. 207, 163 Bortner, C. D. et al. (1995) Trends Cell Biol. 5, 21; Gold, R. et al. (1994); Lab. Invest. 71, 219.

Apoptosis and cell mediated cytotoxicity are characterised by cleavage of the genomic DNA into discrete fragments prior to membrane disintegration. Accordingly, apoptosis may be assayed by measuring DNA fragmentation, for example, by observing the presence of DNA ladders. DNA fragments may be assayed, for example, as "ladders" (with the 180 bp multiples as "rungs" of the ladder) derived from populations of cells, or by quantification of histone complexed DNA fragments via, for example, ELISA. Such an assay relies on an one-step sandwich immunoassay to detect nucleosomes. The procedure involves pelleting cells by centrifugation and discarding the supernatant (which contains DNA from necrotic cells that leaked through the membrane during incubation). Cells are resuspended and incubated in lysis buffer. After lysis, intact nuclei are pelleted by centrifugation. An aliquot of the supernatant is transferred to a streptavidin-coated well of a microtiter plate, and nucleosomes in the supernatant are bound with two monoclonal antibodies, anti-histone (biotin-labelled) and anti-DNA (peroxidase-conjugated). Antibody-nucleosome complexes are bound to the microtiter plate by the streptavidin. The immobilised antibody-histone complexes are washed three times to remove cell components that are not immuno-reactive, and the sample is incubated with peroxidase substrate (ABTS®). The amount of colored product (and thus, of immobilized anti-body-histone complexes) is then determined spectrophotometrically.

Several proteases are involved in the early stages of apoptosis. Apoptosis may therefore also be assayed by detecting the presence of, in addition to, or instead of assaying the activity of, apoptosis-induced proteases such as caspases, e.g., caspase 3. Caspase activation can be analyzed in different ways, for example, by an in vitro enzyme assay of, for example, cellular lysates by capturing of the caspase and measuring proteolytic cleavage of a suitable substrate. Furthermore, caspases may be assayed by detection of cleavage of an in vivo caspase substrate such as PARP (Poly-ADP-Ribose-Polymerase). Cleaved fragments of PARP may be detected with a suitable antibody such as an anti PARP antibody. Protease assays and DNA fragmentation assays are especially suitable for assaying apoptosis in cell populations.

Methods for studying apoptosis in individual cells are also available, such as ISNT and TUNEL enzymatic labeling assays. As noted above, extensive DNA degradation is a characteristic event which often occurs in the early stages of apoptosis. Cleavage of the DNA yields double-stranded, low molecular weight DNA fragments (mono- and oligonucleosomes) as well as single strand breaks ("nicks") in high molecular weight-DNA. In TUNEL, such DNA strand breaks are detected by enzymatic labeling of the free 3'-OH termini with suitable modified nucleotides (such as X-dUTP, X=biotin, DIG or fluorescein). Suitable labeling enzymes include DNA polymerase (nick translation) in ISNT ("in situ nick translation") and terminal deoxynucleotidyl transferase (end labeling) in TUNEL ("TdT-mediated X-dUTP nick end labeling"; Huang, P. & Plunkett, W., 1992, Anal. Biochem. 207, 163; Bortner, C. D. et al., 1995, Trends Cell Biol. 5, 21).

Apoptosis may also be assayed by measuring membrane alterations, including: loss of terminal sialic acid residues from the side chains of cell surface glycoproteins, exposing new sugar residues; emergence of surface glycoproteins that may serve as receptors for macrophage-secreted adhesive molecules such as thrombospondin; and loss of asymmetry in cell membrane phospholipids, altering both the hydrophobicity and charge of the membrane surface. In particular, the human anticoagulant annexin V is a 35-36 kilodalton, Ca2+-dependent phospholipid-binding protein that has a high affinity for phosphatidylserine (PS). In normal viable cells, PS is located on the cytoplasmic surface of the cell membrane. However, in apoptotic cells, PS is translocated from the inner to the outer leaflet of the plasma membrane, thus exposing PS to the external cellular environment. Annexin V may therefore be used to detect phosphatidylserine asymmetrically exposed on the surface of apoptotic cells (Homburg, C. H. E. et al. 1995, Blood 85, 532; Verhoven, B. et al., 1995, J. Exp. Med. 182, 1597). Furthermore, DNA stains such as DAPI, ethidium bromide and propidium iodide, etc may be used for differential staining to distinguish viable and non-viable cells. Profiles of DNA content may also be used; thus, permeabilized apoptotic cells leak low molecular weight DNA, and detection of "sub-G1 peaks", or "A0" cells (cells with lower DNA staining than that of G1 cells) may be detected by, for example, flow cytometry. Morphological changes characteristic of apoptosis may also be detected in this manner.

Detection of apoptosis-related proteins such as ced-3, ced-4, ced-9 (Ellis, H. M. and Horvitz, H. R., 1986, Cell 44, 817-829; Yuan, J. Y. and Horvitz, H. R., 1990, Dev. Biol. 138, 33-41; Hentgartner, M. O., Ellis, R. E. and Horvitz, H. R., 1992, Nature 356, 494-499.), Fas(CD95/Apo-1; Enari et al., 1996, Nature 380, 723-726), Bcl-2 (Baffy, G. et al., 1993, J. Biol. Chem. 268, 6511-6519; Miyashita, T. and Reed, J. C., 1993, Blood 81, 151-157; Oltvai, Z. N., Milliman, C. L. and Korsmeyer, S. J., 1993, Cell 74, 609-619), p53 (Yonish-Rouach, E. et al., 1991, Nature 352, 345-347), etc by the use of antibodies may also be used to assay apoptosis.

Other Indications

The findings shown in the Examples support a therapeutic role for rSP-D N/CRD) in diseases in which the defective clearance or regulation of apoptotic and necrotic alveolar macrophages contributes to chronic pulmonary inflammation. Examples of such indications are discussed above, in particular, the setting of relative SP-D deficiency such as chronic lung disease of the premature newborn and in smokers (who have decreased SP-D levels) at risk of developing emphysema due to chronic lung inflammation.

The data presented in the Examples shows that SP-D is involved in the regulation and clearance of apoptotic cells, and that rSPD(n/CRD) polypeptide, nucleic acid, or a fragment, homologue, variant or derivative thereof may be used to enhance the clearance of apoptotic cells such as apoptotic alveolar macrophages. Accordingly, rSPD(n/CRD) polypeptide, nucleic acid, or a fragment, homologue, variant or derivative thereof may be used to treat atherosclerosis, abnormalities of development, for example, abnormal post natal lung development in neonatal lung disease following premature birth, a disease associated with defective remodelling of inflamed tissues, cellular proliferation and cancer.

Atherosclerosis

In a preferred embodiment of the invention, the inflammatory disease comprises atherosclerosis.

Atherosclerosis is a multi-factorial disease based on the action of various risk factors that become effective on an appropriate genetic background. Atherosclerosis is characterised by the formation of foam cells (i.e. macrophages and smooth muscle cells that have taken up chemically modified eg. Oxidised low density lipoproteins (oxLDL). We have demonstrated the lung phenotype of SP-D knock-out mice, as shown in the Examples, in particular that macrophages are highly abnormal and foamy and there are disturbances of phospholipid turnover in the lung. It is known that SP-D is present in appreciable amounts in the serum, especially in certain disease states.

We therefore provide that disruption of lipid turnover in the serum confers an increased risk of atherosclerosis. Accordingly, rSP-D (N/CRD) may be used to treat atherosclerosis.

Figure 17:
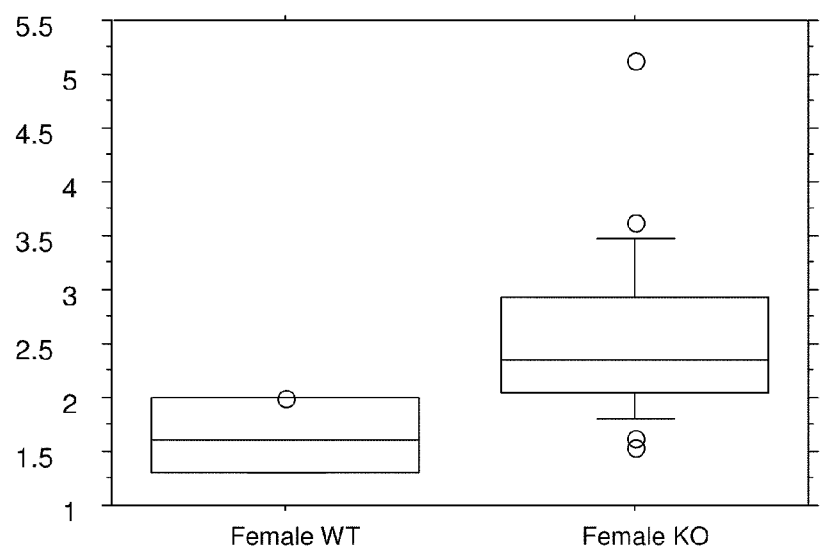
FIG. 17 shows plasma cholesterol levels in mM in wild-type and SP-D knock-out mice.

We have measured cholesterol levels in the serum of wild type and knock-out mice and show that cholesterol levels are higher in knock-out mice (See FIG. 17). High levels of cholesterol are known to confer an increased risk of atherosclerosis. We therefore disclose that supplementation with recombinant SP-D, for example, rSP-D (N/CRD) intravenously, corrects this abnormality.

Furthermore, it has recently been shown that apoptosis plays a major role in modulating the generation of atherosclerotic lesions in vascular cells (Martinet W, Kockx M M. *Apoptosis in atherosclerosis: focus on oxidized lipids and inflammation. Curr Opin Lipidol.* 2001 Oct.; 12(5):535-41; Kockx M M, Herman A G. *Apoptosis in atherosclerosis: beneficial or detrimental? Cardiovasc Res.* 2000 Feb.; 45(3): 736-46). Apoptosis of macrophages could be beneficial for plaque stability provided apoptotic bodies are removed. However apoptotic cells that are not scavenged in the plaque activate thrombin which could further induce intraplaque thrombosis. It can be concluded that apoptosis in primary atherosclerosis is detrimental since it could lead to plaque rupture and thrombosis. We show in the Examples that treatment with recombinant SP-D reduces numbers of apoptotic macrophages in the lungs of SP-D knock-out mice.

Therefore, a potential application of recombinant SP-D administered intravenously is the reduction of detrimental apoptotic cells (eg. Macrophages) in the vasculature, which may reduce the risk of development of atherosclerosis. rSP-D (N/CRD) can therefore be used to treat or prevent any one or more of the symptoms of atherosclerosis.

Pharmaceutical Compositions

We note that rSPD(n/CRD) polypeptides may be produced in large amounts at low cost in a bioactive form, allowing for the first time the development of rSP-D (N/CRD) containing surfactant formulations or of co-administration of rSP-D (N/CRD) separately by aerosolisation, nebulisation, intranasal or intratracheal administration. The preparation is stable and maintains bioactivity after freeze-drying and resuspension, facilitating storage. Unlike current therapy with corticosteroids which have undesirable systemic side effects, rSP-D (N/CRD) appears to have no ill effects in mice and is unlikely to generate side-effects in humans.

While it is possible for the composition comprising the rSPD(n/CRD) polypeptide or nucleic acid to be administered alone, it is preferable to formulate the active ingredient as a pharmaceutical formulation. We therefore also disclose pharmaceutical compositions comprising rSPD(n/CRD) polypeptide or nucleic acid, or a fragment, homologue, variant or derivative thereof. Such pharmaceutical compositions are useful for delivery of rSPD(n/CRD) polypeptide, nucleic acid, fragment, homologue, variant or derivative thereof to an individual for the treatment or alleviation of symptoms as described.

The composition may include the rSPD(n/CRD) polypeptide, nucleic acid, fragment, homologue, variant or derivative thereof, a structurally related compound, or an acidic salt thereof. The pharmaceutical formulations comprise an effective amount of rSPD(n/CRD) polypeptide, nucleic acid, fragment, homologue, variant or derivative thereof, together with one or more pharmaceutically-acceptable carriers. An "effective amount" of an rSPD(n/CRD) polypeptide, nucleic acid fragment, homologue, variant or derivative thereof is the amount sufficient to alleviate at least one symptom of a disease as described, for example, an inflammatory disease, preferably eczema, an inflammatory lung disease, neonatal chronic lung disease, neonatal respiratory distress syndrome (RDS), adult respiratory distress syndrome, chronic obstructive airways disease (COPD), asthma, cystic fibrosis, pulmonary fibrosis, emphysema, interstitial inflammatory lung disease, sarcoidosis, pneumonia, chronic inflammatory lung disease, neonatal chronic inflammatory lung disease, an allergy, allergy is to house dust mite (*Dermatophagoides* app, preferably *Dermatophagoides pteronyssinus* or *Dermatophagoides farinae*, or to fungi or fungal spores, preferably *Aspergillus fumigatus*, a seasonal respiratory allergy, allergic rhinitis, hayfever, nonallergic rhinitis, vasomotor rhinitis, irritant rhinitis, an allergy against grass pollens, tree pollens or animal danders, an allergy associated with allergic asthma, a food allergy, microbial infection, including bacterial infection and viral infection, preferably a microbial infection of the lung.

The effective amount will vary depending upon the particular disease or syndrome to be treated or alleviated, as well as other factors including the age and weight of the patient, how advanced the disease etc state is, the general health of the patient, the severity of the symptoms, and whether the rSPD (n/CRD) polypeptide, nucleic acid, fragment, homologue, variant or derivative thereof is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, The carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The pharmaceutical compositions disclosed here include those suitable for topical and oral administration, with topical formulations being preferred where the tissue affected is primarily the skin or epidermis (for example, psoriasis, eczema and other epidermal diseases). The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. As an example, an acute skin proliferation disease generally is treated with aqueous drying preparations, whereas chronic skin proliferation disease is treated with hydrating preparations. Soaks are the easiest method of drying acute moist eruptions. Lotions (powder in water suspension) and solutions (medications dissolved in a solvent) are ideal for hairy and intertriginous areas. Ointments or water-in-oil emulsions, are the most effective hydrating agents, appropriate for dry scaly eruptions, but are greasy and depending upon the site of the lesion sometimes undesirable. As appropriate, they can be applied in combination with a bandage, particularly when it is desirable to increase penetration of the agent composition into a lesion. Creams or oil-in-water emulsions and gels are absorbable and are the most cosmetically acceptable to the patient. (Guzzo et al, in Goodman & Gilman's Pharmacological Basis of Therapeutics, 9th Ed., p. 1593-15950 (1996)). Cream formulations generally include components such as petroleum, lanolin, polyethylene glycols, mineral oil, glycerin, isopropyl palmitate, glyceryl stearate, cetearyl alcohol, tocopheryl acetate, isopropyl myristate, lanolin alcohol, simethicone, carbomen, methylchlorisothiazolinone, methylisothiazolinone, cyclomethicone and hydroxypropyl methylcellulose, as well as mixtures thereof.

Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the rSPD(n/CRD) polypeptide, nucleic acid, fragment, homologue, variant or derivative thereof composition in the topical formulation is in an amount of about 0.5 to 50% by weight of the composition, preferably about 1 to 30%, more preferably about 2-20%, and most preferably about 5-10%. The concentration used can be in the upper portion of the range initially, as treatment continues, the concentration can be lowered or the application of the formulation may be less frequent. Topical applications are often applied twice daily. However; once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of active ingredient must penetrate a patient's skin in order to obtain a desired pharmacological effect. It is generally understood that the absorption of drug into the skin is a function of the nature of the drug, the behaviour of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (J. Pharm. Sci., 60:1175-1179 (1971) demonstrated that in vivo efficacy of topically applied steroids was proportional to the steroid penetration rate into dermatomed human skin in vitro.

A skin penetration enhancer which is dermatologically acceptable and compatible with the agent can be incorporated into the formulation to increase the penetration of the active compound(s) from the skin surface into epidermal keratinocytes. A skin enhancer which increases the absorption of the active compound(s) into the skin reduces the amount of agent needed for an effective treatment and provides for a longer lasting effect of the formulation. Skin penetration enhancers are well known in the art. For example, dimethyl sulfoxide (U.S. Pat. No. 3,711,602); oleic acid, 1,2-butanediol surfactant (Cooper, J. Pharm. Sci., 73:1153-1156 (1984)); a combination of ethanol and oleic acid or oleyl alcohol (EP 267,617), 2-ethyl-1,3-hexanediol (WO 87/03490); decyl methyl sulphoxide and Azone® (Hadgraft, Eur. J. Drug. Metab. Pharmacokinet, 21:165-173 (1996)); alcohols, sulphoxides, fatty acids, esters, Azone®, pyrrolidones, urea and polyoles (Kalbitz et al, Pharmazie, 51:619-637 (1996));

Terpenes such as 1,8-cineole, menthone, limonene and nerolidol (Yamane, J. Pharmacy & Pharmocology, 47:978-989 (1995)); Azone® and Transcutol (Harrison et al, Pharmaceutical Res. 13:542-546 (1996)); and oleic acid, polyethylene glycol and propylene glycol (Singh et al, Pharmazie, 51:741-744 (1996)) are known to improve skin penetration of an active ingredient.

Levels of penetration of an agent or composition can be determined by techniques known to those of skill in the art. For example, radiolabeling of the active compound, followed by measurement of the amount of radiolabeled compound absorbed by the skin enables one of skill in the art to determine levels of the composition absorbed using any of several methods of determining skin penetration of the test compound. Publications relating to skin penetration studies include Reinfenrath, W G and G S Hawkins. The Weaning Yorkshire Pig as an Animal Model for Measuring Percutaneous Penetration. In: Swine in Biomedical Research (M. E. Tumbleson, Ed.) Plenum, N.Y., 1986, and Hawkins, G. S. Methodology for the Execution of In Vitro Skin Penetration Determinations. In: Methods for Skin Absorption, B W Kemppainen and W G Reifenrath, Eds., CRC Press, Boca Raton, 1990, pp. 67-80; and W. G. Reifenrath, Cosmetics & Toiletries, 110:3-9 (1995).

For some applications, it is preferable to administer a long acting form of agent or composition using formulations known in the arts, such as polymers. The agent can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated.

Optionally, the topical formulations of this invention can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

The pharmaceutical composition can be administered in an oral formulation in the form of tablets, capsules or solutions. An effective amount of the oral formulation is administered to patients 1 to 3 times daily until the symptoms of the disease alleviated. The effective amount of agent depends on the age, weight and condition of a patient. In general, the daily oral dose of agent is less than 1200 mg, and more than 100 mg. The preferred daily oral dose is about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat the disease.

Other therapeutic agents suitable for use herein are any compatible drugs that are effective for the intended purpose, or drugs that are complementary to the agent formulation. The formulation utilized in a combination therapy may be administered simultaneously, or sequentially with other treatment, such that a combined effect is achieved.

Surfactant Therapy Compositions

The development of rSP-D (N/CRD) containing surfactant therapies may be applied to the treatment of neonatal respiratory distress syndrome, in place of current formulations or in conjunction with current formulations.

Current surfactant therapy for newborn respiratory distress syndrome includes the following:

Beractant (SURVANTA)

Beractant (SURVANTA) is a semisynthetic bovine lung extract containing phospholipids, fatty acids, and surfactant-associated proteins B (7 mcg/mL) and C (203 mcg/mL).

Beractant is delivered at a Pediatric Dose of 100 mg (ie, 4 mL)/kg divided in 4 aliquots administered at least 6 h apart (Intratracheal).

Calfactant (INFASURF)

Calfactant (INFASURF) is a natural calf lung extract containing phospholipids, fatty acids, and surfactant-associated proteins B. it is manufactured by Ross, and is delivered at (260 mcg/mL) and C (390 mcg/mL).

SURVANTA® (beractant) Intratracheal Suspension

SURVANTA® (beractant) is a sterile, non-pyrogenic pulmonary surfactant intended for intratracheal use. It is a natural bovine lung extract containing phospholipids, neutral lipids, fatty acids, and surfactant-associated proteins to which colfosceril palmitate (dipalmitoylphosphatidylcholine), palmitic acid, and tripalmitin are added to standardize the composition and to mimic surface-tension lowering properties of natural lung surfactant. The resulting composition provides 25 mg/mL phospholipids (including 11.0-15.5 mg/mL disaturated phosphatidylcholine), 0.5-1.75 mg/mL triglycerides, 1.4-3.5 mg/mL free fatty acids, and less than 1.0 mg/mL protein. It is suspended in 0.9% sodium chloride solution, and heat-sterilized. SURVANTA contains no preservatives. Its protein content consists of two hydrophobic, low molecular weight, surfactant-associated proteins commonly known as SP-B and SP-C. It does not contain the hydrophilic, large molecular weight surfactant-associated protein known as SP-A.

Infrasurf Intratracheal Suspension (Forest)

Infasurf® (calfactant) Intratracheal Suspension is a sterile, non-pyrogenic lung surfactant intended for intratracheal instillation only. It is an extract of natural surfactant from calf lungs which includes phospholipids, neutral lipids, and hydrophobic surfactant-associated proteins B and C (SP-B and SP-C). It contains no preservatives.

Infasurf® is an off-white suspension of calfactant in 0.9% aqueous sodium chloride solution. It has a pH of 5.0-6.0. Each milliliter of Infasurf® contains 35 mg total phospholipids (including 26 mg phosphatidylcholine of which 16 mg is disaturated phosphatidylcholine) and 0.65 mg proteins including 0.26 mg of SP-B.

EXOSURF NEONATAL for Intratracheal Suspension (Glaxo Wellcome)

EXOSURF NEONATAL (colfosceril palmitate, cetyl alcohol, tyloxapol) for Intratracheal Suspension is a protein-free synthetic lung surfactant stored under vacuum as a sterile lyophilized powder. EXOSURF NEONATAL is reconstituted with preservative-free Sterile Water for Injection prior to administration by intratracheal instillation. Each 10-mL vial contains 108 mg colfosceril palmitate, commonly known as dipalmitoylphosphatidylcholine (DPPC), 12 mg cetyl alcohol, 8 mg tyloxapol, and 47 mg sodium chloride. Sodium hydroxide or hydrochloric acid may have been added to adjust pH. When reconstituted with 8 mL Sterile Water for Injection, the EXOSURF NEONATAL suspension contains 13.5 mg/mL colfosceril palmitate, 1.5 mg/mL cetyl alcohol, and 1 mg/mL tyloxapol in 0.1 N NaCl. The suspension appears milky white with a pH of 5 to 7 and an osmolality of 185 mOsm/kg.

The chemical names of the compounds of EXOSURF NEONATAL are as follows: colfosceril palmitate: (R)-4-hydroxy-N,N,N-trimethyl-10-oxo-7-[(1-oxohexadecyl)oxy]-3,5,9-trioxa-4-phosphapentacosan-1-aminium hydroxide inner salt, 4-oxide; cetyl alcohol: (1-hexadecanol); and tyloxapol: 4-(1,1,3,3-tetramethylbutyl)phenol polymer with formaldehyde and oxirane.

In EXOSURF NEONATAL, which is protein free, cetyl alcohol acts as the spreading agent for the DPPC on the air-fluid interface. Tyloxapol, a polymeric long-chain repeating alcohol, is a nonionic surfactant which acts to disperse both DPPC and cetyl alcohol. Sodium chloride is added to adjust osmolality.

Curosurf®

Brand Name: Curosurf® Active Ingredient: poractant alfa Strength(s): 120 mg of phospholipid/1.5 mL or 240 mg phospholipid/3 mL vials Dosage Form(s): Intrathracheal suspension Company Name: Dey, L P Availability: Prescription only, for professional use only *Date Approved by the FDA: Nov. 18, 1999.

Accordingly, we disclose the use of compositions including any of the ingredients of the therapies disclosed above, preferably an active ingredient, in conjunction with rSPD(n/CRD) polypeptide, nucleic acid, or a fragment, homologue, variant or derivative thereof, as a surfactant therapy. Thus, we disclose a composition comprising a lung extract together with an rSPD(n/CRD) polypeptide, nucleic acid, or a fragment, homologue, variant or derivative thereof. The lung extract may comprise a bovine, preferably, calf lung extract together with phospholipids (such as phosphatidylcholine and disaturated phosphatidylcholine) and/or fatty acids. The composition may further include a surfactant-associated protein, for example a surfactant-associated protein B or a surfactant-associated protein C. Other components such as cetyl alcohol, long-chain repeating alcohols, tyloxapol, colfosceril palmitate (dipalmitoylphosphatidylcholine), palmitic acid, and tripalmitin, poractant alfa and sodium chloride may also be added.

In particular, we disclose compositions corresponding to each of Beractant (Survanta®); Calfactant (Infasurf®); SURVANTA® (beractant); INFRASURF; EXOSURF NEONATAL; and CUROSURF; in which each composition further comprises a therapeutically effective amount of an rSPD(n/CRD) polypeptide, nucleic acid, or a fragment, homologue, variant or derivative thereof.

Further Aspects

Further aspects include the following:

A method of enhancing MCP-1 levels or MIP1α levels, or both, in an individual, the method comprising administering to the individual an rSPD(n/CRD) polypeptide, fragment, homologue, variant or derivative thereof.

A method of enhancing cytokine levels, preferably IFNγ levels, in an individual, the method comprising administering to the individual an rSPD(n/CRD) polypeptide, fragment, homologue, variant or derivative thereof.

A method of up-regulating a component of the cell-mediated immune system, or up-regulating the activity of natural killer cells, or both, in an individual by administration of an rSPD(n/CRD) polypeptide, fragment, homologue, variant or derivative thereof is also disclosed.

EXAMPLES

Example 1

Materials and Methods

Recombinant Surfactant Protein D Fragment (rSP-D (N/CRD))

The recombinant Surfactant Protein D Fragment (rSP-D (N/CRD)) used in these experiments is a truncated form of human SP-D. We expressed the fragment in *E. coli* from a plasmid containing cDNA for the fragment of human SP-D (the construct) inserted into a pET vector and transformed into *E. coli* for expression using standard fermentation procedures.

The construct is composed of a short stretch of 8 N-terminal Gly-XaaYaa triplets (shown in italics) with a substitution of serine for proline at position 2 followed by the 28 residue neck region (shown in bold) and the 125 residue Carbohydrate Recognition Domain (CRD) of human SP-D.

(SEQ ID NO: 1)
GSPGLKGDKGIPGDKGAKGESGLPDVASLRQQVEALQGQVQHLQAAFSQ

YKKVELFPNGQSVGEKIFKTAGFVKPFTEAQLLCTQAGGQLASPRSAAE

NAALQQLVVAKNEAAFLSMTDSKTEGKFTYPTGESLVYSNWAPGEPNDD

GGSEDCVEIFTNGKWNDRACGEKRLVVCEF

Figure 1A:
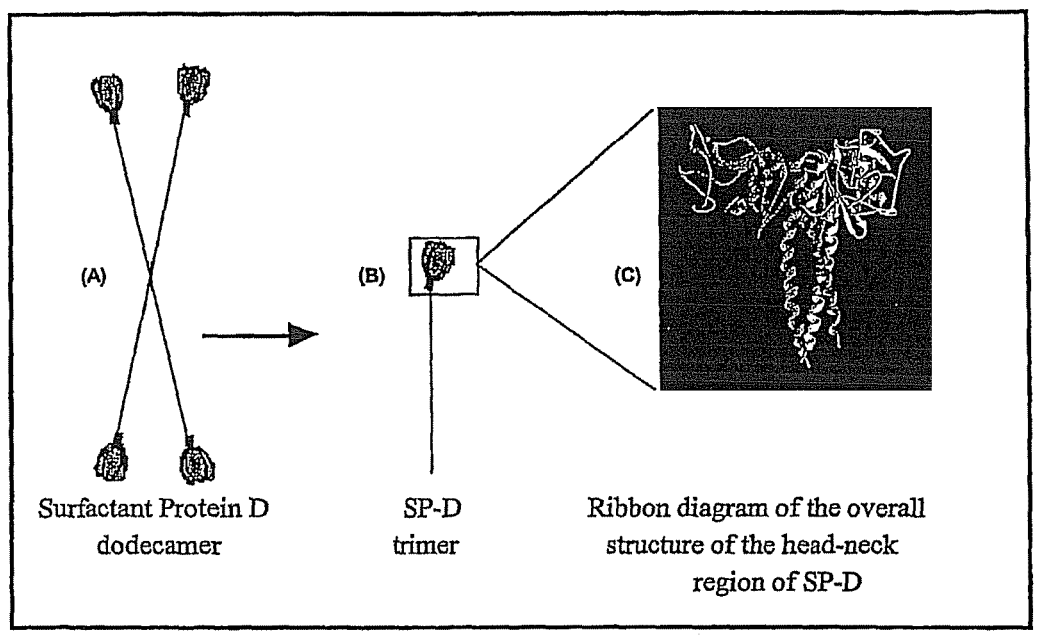

A schematic diagram showing the structure of rSP-D (N/CRD) is shown in FIG. 1A. (A): Surfactant Protein D dodecamer; (B): SP-D trimer; (C): Ribbon diagram of the overall structure of the head-neck region of SP-D.

A nucleic acid sequence encoding rSPD(n/CRD) polypeptide has the sequence shown in SEQ ID NO: 2.

Generation of Expression Construct of rSP-D (n/CRD) in pET Vector pET21d

A sequence encoding the human SP-D (neck/CRD) and including a short stretch encoding 8 N-terminal Gly-XaaYaa triplets was excised from a previously generated human SP-D clone pBCSK1 (Kishore, U., et al., *The alpha-helical neck region of human lung surfactant protein D is essential for the binding of the carbohydrate recognition domains to lipopolysaccharides and phospholipids*. Biochem J, 1996. 318 (Pt 2): p. 505-11.) by digestion with Xba 1 and Hind-3. The resulting fragment is then purified by agarose electrophoresis and ligated into a pET-21d vector (Novagen) which is digested with Nhe1 and Hind 3. The pET-21d vector is available from Novegen under catalogue number 69743-3. Its sequence is known in the art, and is described in for example, literature from Novagen.

Preparation of rSP-D (n/CRD)

The new construct so generated was then used to transform competent cells (DH5α). Plasmid DNA comprising this construct for rSP-D(neck/CRD) is purified after growth of cells from transformed colony by standard methods.

Plasmid containing cDNA for rSPD(n/CRD) (neck/CRD) in a pET vector is transformed into BL21(XDDE3) pLysS and a single colony selected and diluted into 1 ml LB supplemented with 100 µg/ml ampicillin and 25 µg/ml chloramphenicol (LB+) This is further diluted 1000 fold and 100 µl spread onto an agar plate and incubated overnight. The resulting lawn of colonies is collected by scraping with a flat bladed spatula and re-suspended in 50 ml LB+. An aliquot of 5 ml of this is used to inoculate 2 L flasks containing 500 ml LB+. This procedure is found to be superior to the more common practice of growing up an overnight culture in growth medium. The growth of colonies on a stationary phase reduces the contact between cells and reduces the proportion of mutants in the inoculum which do not carry the expression plasmid.

It is also found to be important not to exceed 500 ml LB/2 L flask in order to achieve optimum expression levels. Cultures are grown to $A_{600}$ of 0.6-0.8 followed by induction with 0.4 mM IPTG for 2-3 hr.

Purification of Recombinant Surfactant Protein D Fragment rSP-D (n/CRD)

Cells are harvested by centrifugation and lysed in 20 mM Tris-HCl, 150 mM NaClNaCl, 5 mM EDTA, 0.1% v/v Triton X-100, 0.1 mM PMSF, pH 7.5) and sonicated for 3 minutes. The rSPD(n/CRD) is expressed in insoluble inclusion bodies and is harvested by centrifugation at 10000×g. This step is repeated three times and the purified inclusion body pellet, containing the rSPD(n/CRD), was solubilized in 100 ml of 8 M Urea, 100 mM 2-mercaptoethanol, pH 7.5 and clarified by high speed centrifugation.

The urea solution is diluted into 1 L 20 mM TrisHCl, pH 7.5 and 50 ml of Q Sepharose® anion exchange resin (Pharmacia) added and mixed at 20° C. for 30 min. The adsorbed resin was is into an FPLC column, washed extensively with 20 mM Tris-HCl, 150 mM NaCl, pH 7.5, and the rSPD(n/CRD) is eluted with 50 mM Tris-HCl, 500 mM NaCl, pH 7.5 The protein from the peak fractions is precipitated by a 10:1 dilution into acetone at 4° C. for 30 min. The precipitate is harvested by high speed centrifugation and dissolved in 100 ml of 8 M Urea and dialysed against 10 L of 20 mM Tris-HCl, 150 mM NaCl, 2 mM $CaCl_2$, pH 7.4, overnight at 4° C.

The dialysate is then mixed with 20 ml of maltose-agarose for several hours to over-night in 20 mM Tris-HCl, 10 mM $CaCl_2$, pH 7.4. This long incubation step probably facilitates the final stages of re-folding into active protein.

The maltose-agarose is packed into an FPLC column and washed with the same buffer containing 1M NaCl to remove non-specific proteins. The high salt wash elutes approximately 25-50% of the total $OD_{280}$ absorbing material bound to the column. SDS-PAGE shows traces of rSPD(n/CRD) (approximately 10%), which is presumably low affinity rSPD (n/CRD) that may not be fully folded into the correct 3D structure. As these preparations of rSPD(n/CRD) are to be used in structural studies and in experiments in mice, it is considered advisable not to include this fraction. In addition the total $OD_{280}$ absorbing material in the high salt is far greater than could be attributed to this rSPD(n/CRD) and is probably due to bacterial DNA and other substances that are deemed undesirable in a preparation for administering to animals.

The bound rSPD(n/CRD) was then eluted with 20 mM Tris-HCl, 150 mM NaCl, 0.02% (w/v) sodium azide pH 7.4, containing 5 mM EDTA to remove the Ca required for rSPD (n/CRD) CRD mediated binding.

The peak fractions are concentrated using an Amicon stirred cell with a 10 000 MWCO membrane to 5 ml and loaded onto a 100 ml Superose™ 12 gel filtration column (Pharmacia) in a running buffer of 20 mM Tris-HCl, 150 mM NaCl, 5 mM EDTA, 0.02% (w/v) sodium azide pH 7.4. The rSPD(n/CRD) eluted as a single peak corresponding to 60 kDa molecular weight.

This step allows the final dissociation of any impurities that might have co-purified to this stage and in the presence of EDTA any carbohydrates will dissociate from the rSPD(n/CRD) and would be expected to elute in the total inclusion volume of the column (100 ml) since they should have a lower molecular weight. This step also allows an assessment of the homogeneity of the protein preparation by the symmetry of the protein peak and absence of shoulders. Fractions outside the main peak are discarded. The pooled fractions are collected and concentrated to 2 mg/ml before proceeding to the next step. The recovery of rSPD(n/CRD) after gel filtration is typically 80% of the total $OD_{280}$ absorbing material loaded. This indicates that at least 20% of this is not due to rSPD(n/CRD) and reinforces the need for including gel filtration as a final step.

Endotoxin levels are reduced by passing the purified rSPD (n/CRD) in 20 mM Tris-HCl, 150 mM NaCl, 5 mM EDTA, 0.02% (w/v) sodium azide pH 7.4 through a 10 ml Polymixin B column Detoxi-Gel™, Pierce).

Modification of rSP-D by FITC Labelling

To assess in vitro binding to macrophages isolated by BAL of mice, rSP-D is labelled with the amine reactive probe FITC (Sigma) according to the manufacturer's instructions. Briefly, 50 µg of FITC is incubated with 1 mg rSP-D in 200 ml of 0.1M sodium bicarbonate buffer pH 9.0 at room temperature for 2 hours.

The labelled protein is then separated from free FITC using a G-25 column. FITC-rSP-D (20 µg/ml) is incubated with freshly isolated alveolar macrophages from wild-type and SP-D knock-out mice in binding buffer (10 mM Hepes, 140 mM NaCl, 2.5 mM $CaCl_2$) and assessed for co-labelling with propidium iodide or PB-labeled annexin V as outlined below by flow cytometry on a Consort™ 32 FACs System.

Preparation of *Aspergillus fumigatus* Antigen (Afu 1 wcf)

*Aspergillus fumigatus* (Afu) is grown in a synthetic medium (M199, Sigma Chemicals) as a stationary culture for 1 week at 37° C. Arrunda, et al, (Arruda, L. K., B. J. Mann, and M. D. Chapman. 1992. Selective expression of a major allergen and cytotoxin, Asp f I, in *Aspergillus fumigatus*. Implications for the immunopathogenesis of *Aspergillus*-related diseases. *J. Immunol.* 149:3354-9.) demonstrates that the expression of Asp f1, a major allergen, is maximal after 1 week and tends to diminish during longer incubation periods.

The 1 week culture is killed by adding 0.1% Thimerosal for 12 hours. The culture is filtered through glass wool and finally through a 0.45 µm membrane to remove all particulates and possible spores and then dialysed with 3 buffer changes against water. The dialysate is lypholised to give a brown powder.

There is a major band at 18 kDa, which corresponds to Asp f1. A band corresponding to Asp f2 (37 kDa) is also evident. The 18 kDa band is N-terminal sequenced giving the sequence ATWTCINQQLNP (SEQ ID NO: 8), corresponding to the N-terminal sequence for Asp f 1.

It is also demonstrated by ELISA that the 1-week culture filtrate (1 wcf) is recognised by human serum from Afu-allergic patients obtained from the National Institute of Biological Standards and Control.

Transgenic Strains

We have previously reported the generation of gene-targeted SP-D deficient mice (Botas, C., Poulain, F., Akiyama, J., Brown, C., Allen, L., Goerke, J., Clements, J., Carlson, E., Gillespie, A. M., Epstein, C. & Hawgood, S. (1998) *Proc Natl Acad Sci USA* 95, 11869-74.).

SP-D deficient mice backcrossed 10 generations into a C57B16 background are fed ad libitum and housed in isolators in a pathogen free environment in the Biomedical Services Unit, Oxford University. Pathogen-free C57B16 wild-type mice for control experiments are obtained from Harlan-OLAC, Shaw's farm, Bicester, Oxfordshire. All experimental protocols are approved by appropriate U.K. Home Office licensing authorities and by the University of Oxford Ethical Committee.

Administration of rSP-D, rSP-A, and Bovine Serum Albumin (BSA)

6-week old SP-D deficient mice underwent multiple intranasal administrations of protein or PBS alone over a period of 3-6 weeks using one of three protocols.

For each protein administration mice are lightly anaesthetised with isofluorane before rSP-D or control protein (30 µg, 25 µg, or 10 µg of rSP-D, rSP-A or BSA in 50 µl of PBS) is applied to the nares using a sterile micropipette. Mice are held upright after each dose until all of the fluid is inhaled. In the first treatment protocol twelve mice received 30 µg doses of rSP-D every three days from age six weeks. Six mice are sacrificed after three weeks for assay of alveolar macrophage number and alveolar phospholipid content. The remaining six mice in the treatment group completed six weeks of treatment before sacrifice and assay. In the second treatment protocol, mice are treated from age 12 weeks with 10 µg doses of rSP-D, rSP-A, BSA five times per week for three weeks before sacrifice and assay. Additional controls are untreated mice and mice treated with PBS. To assess the effect of treatment from age four weeks, before a significant increase in alveolar macrophage numbers occurs, six mice are treated in a third protocol for two weeks with 30 µg doses of rSP-D. These mice are sacrificed at age six weeks for assay of phospholipids and alveolar macrophage numbers, and compared to untreated age matched controls.

Bronchoalveolar Lavage (BAL)

For isolation of alveolar macrophages (for example for an apoptosis assay), 4-6 mice in each treatment group are sacrificed by asphyxiation with carbon dioxide and undergo bronchoalveolar lavage (BAL) with sterile RPMI.

A sterile cannula is inserted into the trachea and tied in position with thread. Using a 2 ml syringe, the lungs are lavaged with 1 ml volumes of lavage buffer, four times to yield a total lavage volume of approximately 3 ml. BAL fluid is then centrifuged at 250 g for 5 minutes at room temperature to pellet alveolar macrophages. Cells are washed by resuspension in 1 ml of PBS and pelleted again by centrifugation in a benchtop centrifuge at 1000 rpm for 2 minutes. Cells are then resuspended and incubated with FITC-labelled Annexin V and Propidium iodide for 10 minutes. Samples are then analysed for staining by FACS flow cytometry.

Cytospin Preparations of Alveolar Macrophages

Alveolar macrophages isolated by bronchoalveolar laveage using PBS with 0.25 mM EDTA and centrifugation at 250 g are resuspended in 1 ml of PBS. Aliquots are taken for total cell counting by hemocytometer after staining with malachite green or crystal violet and preparation of cytospin slides using standard procedures. Differential cell counts on cytospin preparations after staining with Diff-Quik® (Scientific Products, McGaw Park, Ill.) confirm that 98% of the cells isolated in this way are alveolar macrophages.

In Vitro Labelling of Mouse Alveolar Macrophages

Alveolar macrophages isolated from BAL of wild-type and knock-out mice are labelled in vitro with fluorescent green and orange cell tracker dyes. Cell Tracker™ Orange consisting of CMTMR (5-(and-6)(((4-chloromethy)benzoyl)amino) tetramethylrhodamine mixed isomers and Cell Tracker™.

Green (Molecular probes, Eugene, Oreg.) consisting of CMFDA (5-chloromethylfluorescein diacetate) contain a mildly thiol reactive chloreomethyl group. Once inside the cell, the chloromethyl group reacts with intracellular thiols, transforming the probe into a cell impermeant fluorescent dye ether adduct. Excess unconjugated reagent passively diffuses to the extracellular medium. Cell Tracker™ Orange does not need esterase activity to be fluorescent, whereas cell tracker green is colourless until cleaved by intracellular esterases.

Bronchoalveolar Lavage Fluid Total Phospholipid and Protein Measurements

At the time points indicated in individual experiments, 4-6 mice in each treatment group are sacrificed by asphyxiation with carbon dioxide and underwent bronchoalveolar lavage (BAL) with sterile PBS containing 0.25 mM EDTA. The lungs are lavaged with 1 ml four times to yield a total lavage volume of approximately 3 ml. The BAL fluid is centrifuged at 250 g for 5 minutes at room temperature. Total protein concentration in the cell free supernatant is determined using bicinchoninic acid as a substrate. Cell free BAL fluid is extracted into chloroform methanol and the total phospholipid derived from the phosphorous concentration.

rSP-D Levels in Mouse BAL Fluid

Serial dilutions of cell free BALF from rSP-D treated mice are analysed for rSP-D content by standard sandwich ELISA methodology using biotinylated and non-biotinylated, monospecific, polyclonal antibodies raised against recombinant human SP-D. This antibody showed no cross reactivity with mouse SP-A or mouse SP-D. Standard curves using recombinant human SP-D are used to calculate the absolute amounts of alveolar rSP-D recovered at specific time points alter administration.

Flow Cytometry and Detection of Apoptotic and Necrotic Cells

Cells isolated from BAL of SP-D deficient mice with RPMI are resuspended in PBS and analysed on a Consort™ 32 FACs System (Becton Dickinson Immunocytometry Systems, San Jose, Calif.) to characterise the macrophage population by size and granularity. Cell preparations with obvious blood staining are discarded. Apoptotic cells and necrotic cells are detected by annexin V and propidium iodide (PI) staining using an Annexin-V-FLUOS staining kit (Roche Diagnostics, Mannheim, Germany). Apoptotic and necrotic cells expose phosphatidylserine (PS), which is normally present on the inner cell membrane leaflet to the outer leaflet, allowing annexin V to bind to PS at the cell surface (Vermes, I., Haanen, C., Steffens-Nakken, H. & Reutelingsperger, C. (1995) *J Immunol Methods* 184, 39-51.). Cell aliquots are stained with fluorescent-labelled annexin V and counterstained with PI to detect primary or secondary necrotic cells. In co-labelling experiments, binding of FITC-labelled rSP-D to cells staining with PI or PE-labelled annexin V (Pharmingen, San Diego, Calif.) are also assessed after compensation for overlap of fluorescent signals.

Data Analysis

Results are given as means±standard errors of the mean (x±SE). Comparisons between groups of animals at individual time points are made with two-tailed t-tests assuming unequal variance. Significance is accepted at P<0.05.

Example 2

Modulation of Allergic Hypersentivity in a Murine Model of Allergic Hypersensitivity to *Aspergillus fumigatus*

The truncated form of human SP-D composed of timers of the neck and CRD domains, expressed and purified in *E. coli* and referred to as rSPD(n/CRD), is functionally active as a modulator of allergic hypersensitivity reactions in mice. In this present study, modulation of eosinophilia, serum IgE and IgG1, has been reproduced in C57BL/6, thus demonstrating that the effects are not peculiar to BALB/c mice.

The parameters measured in the present study are serum IgE and IgG1 and peripheral blood eosinophilia which are all significantly elevated in the mouse model of allergy to *Aspergillus fumigatus* allergens and all significantly reduced by intranasal treatment with rSPD(n/CRD).

Without seeming to be bound by any particular theory, it is proposed that rSPD(n/CRD) promotes a shift in the populations of T lymphocytes from Th2 to Th1. This culminates in the observed reduction in serum IgE and eosinophilia, which are major components in allergy.

Preparation of rSPD(n/CRD)

The cDNA for the neck/CRD, including a short region of the collagen stalk (8 Gly-X-Y) and representing residues 179-355 of the mature protein sequence is cloned from human lung library DNA and inserted into a pET-21d vector (Novagen, Nottingham). The plasmid is transformed into BL21 (λDE3) pLysS and a single colony selected and re-plated to give 100-400 colonies/plate. These are scraped and used to inoculate shake-flasks containing 500 ml LB medium supplemented with 100 µg/ml ampicillin and 25 µg/ml chloramphenicol and grown to an OD600 of 0.6-0.8 followed by induction with 0. mM IPTG for 2-3 hr. Cells are collected by centrifugation and lysed in 20 mM Tris-HCl, 150 mM NaCl, 5 mM EDTA, 0.1% v/v Triton X-100, 0.1 mM PMSF, pH 7.5) and sonicated for 3 minutes. The rSPD(n/CRD) is expressed in insoluble inclusion bodies and is collected by centrifugation and washed 4 times at 10000×g. The pellet is solubilized in 100 ml of 8 M Urea, 100 mM 2-mercaptoethanol, pH 7.5 and clarified by centrifugation and refolded by overnight dialysis against 10 L of 20 mM Tris-HCl, 150 mM NaCl, 5 mM CaCl$_2$ (TCB). Refolded rSPD(n/CRD) is separated from denatured rSPD(n/CRD) by absorption onto maltose-agarose (Sigma-Aldrich, Poole, UK) and eluted with 20 mM Tris-HCl, 150 mM NaCl, containing 5 mM EDTA after first washing the column with TCB containing 1M NaCl to remove impurities. Final purification is by gel filtration column (Superose™ 12, Amersham Pharmacia, UK)) in a running buffer of 20 mM Tris-HCl, 150 mM NaCl, 5 mM EDTA, 0.02% (w/v) sodium azide pH 7.4 (TSE). The rSPD(n/CRD) eluted as a single peak corresponding to 60 kDa molecular weight. Endotoxin levels are reduced by passing the purified rSPD(n/CRD) in through a 10 ml Polymixin B column (Detoxi-Gel™, Pierce & Warriner, UK) and only preparations containing less than 5 pg/µg rSPD(n/CRD) are used.

*Aspergillus fumigatus* Antigen (Afu 1 wcf)

Figure 1B:
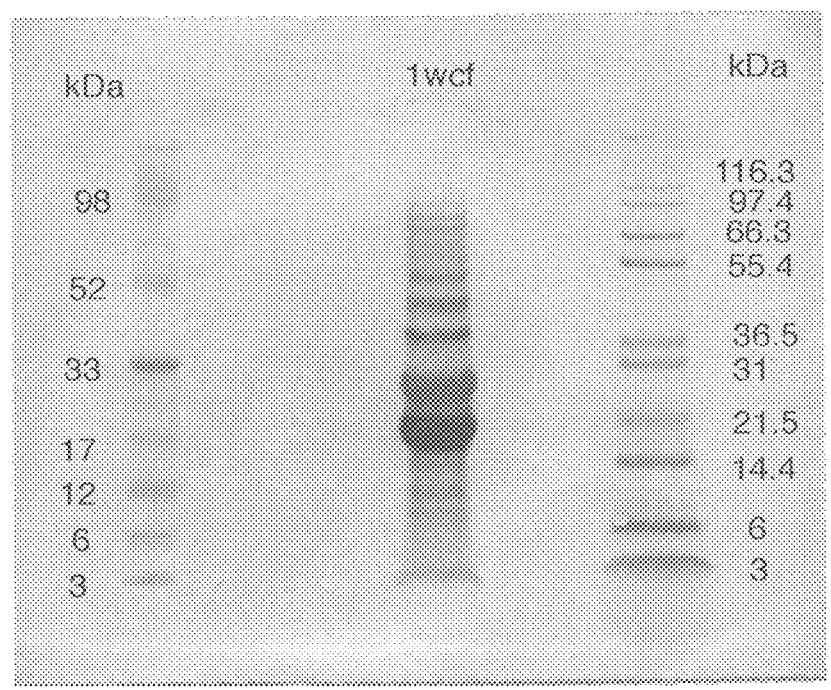

*Aspergillus fumigatus* (Mu) is grown in a synthetic medium (M199, Sigma Chemicals) as a stationary culture for 1 week at 37° C. Arruda, et al, [Arruda L K, Mann B J, Chapman M D. Selective expression of a major allergen and cytotoxin, Asp f I, in *Aspergillus fumigatus*. Implications for the immunopathogenesis of *Aspergillus*-related diseases. J Immunol 1992; 1493354-9] demonstrated that the expression of Asp f 1, a major allergen, is maximal after 1 week and tends to diminish during longer incubation periods. The 1 week culture is killed by adding 0.1% (w/v) Thimerosal for 12 hours at 4° C. The culture is filtered through glass wool and finally through a 0.45 µm membrane to remove all particulates and spores and then dialysed with 3 buffer changes against water. The dialysate is lypholised to give a brown powder. SDS PAGE (FIG. 1B) of 1 wcf revealed a major band at 18 kDa, which corresponds to Asp f 1. A band corresponding to Asp f 2 (37 kDa) is also evident. The 18 kDa band is N-terminal sequenced giving the sequence ATWTCINQQLNP (SEQ ID NO: 8), corresponding to the N-terminal sequence for Asp f 1. It is also demonstrated by ELISA that the 1-week culture filtrate (1 wcf) is recognised by human serum from Afu-allergic patients obtained from the National Institute of Biological Standards and Control.

Sensitisation

In this study, 6 week old female C57BL/6 mice are sensitised by intra-peritoneal (i.p.) injections of 200 µg Afu 1 wcf mixed with alum (1:4 v/v) in 100 µg PBS given once a week for 4 weeks.

Allergen Challenge and Treatment

Sensitised mice are challenged with 501.11 containing 10 µg of Afu 1 wcf given intranasally (i.n.). This is followed by treatment with PBS or 10 µg rSPD(n/CRD) in 50 µl PBS given in. Challenge and treatment are performed on a daily basis as described in the results. In some experiments, a control protein of full length recombinant human SP-A (kindly provided by Byk Gulden Pharmaceuticals) is used at a concentration of 10 µg/50 µl. In a separate experiment the fate of rSPD(n/CRD) is monitored by obtaining BAL from different mice at various times after intranasal application rSPD(n/CRD) in 50 µl PBS and assaying for rSPD(n/CRD) using a polyclonal antibody raised against rSPD(n/CBD) that does not recognise mouse SP-D or SP-A. These results show that at least 50% of rSPD(n/CRD) could be accounted for in the BAL taken 30 minutes after administration and none could be measured after 24 hrs.

Peripheral Blood Eosinophils

Blood is collected from the tail vein of the mice (n=4-8/group) for estimation of eosinophils. Total leukocyte count is measured with an automatic cell counter and the proportion of eosinophils is determined by differential counting of May-Grunwald-Giemsa stained blood smears. Results are expressed as $10^6$ cells/ml.

Serum IgE and Afu-specific IgG1

Total serum IgE is measured by sandwhich ELISA (BD PharMingen, Cowley, UK) in blood serially diluted from a maximum dilution of 1:20 to give values, which are linear with respect to a standard curve of mouse IgE. Results are expressed in µg/ml. Afu-specific IgG1 is measured by ELISA using 96-well plates coated with Afu allergen extract. Antibody is detected with HRP-labeled anti-mouse IgG1. Results are expressed as relative absorbance units (OD450).

Endogenous Mouse SP-D and SF-A in the Lung

Immediately after humane sacrifice by $CO_2$ asphyxiation, broochoalveolar lavage is performed with 3×1 ml PBS, which are pooled and the volumes adjusted by addition of PBS to 4 ml for all samples and centrifuged to remove cells. SP-D and SP-A are measured by ELISA using polyclonal antibodies raised against recombinant mouse SP-D and SP-A (kindly provided by Dr. P. Lawson). These antibodies are shown not to cross-react with human SP-D or SP-A and are specific for mouse SP-D or SP-A, respectively. Results are expressed as µg/ml of BAL.

Intracellular Cytokine Staining.

After treatment, mice are humanely sacrificed by $CO_2$ asphyxiation and their spleens removed and homogenized in PBS. The homogenate is filtered and red blood cells lysed with ammonium chloride lysing reagent (BD Pharmingen) and fixed with 4% (v/v) paraformaldehyde for 20 mins. The cells are washed with PBS supplemented with 3% (v/v) heat inactivated fetal calf serum with 0.1% (w/v) sodium azide (FSB), re-suspended in 10% DMSO (v/v) in FSB and stored at −80° C. Cells are permeabilized with Cytoperm™ wash buffer (CPB, BD Biosciences, Cowley, UK) for 15 mins at 4° C. and aliquots of $10^6$ cells are blocked by incubation for 30 mins at 4° C. with CPB supplemented with 50 µg/ml rat IgG. Intracellular cytokines are stained with 1 µg PE-conjugated anti-mouse cytokine monoclonal antibody (BD Biosciences) incubated for 60 mins at 4° C. The cells are washed with CPB followed by FSB and re-suspended in 500 □l FSB. Flow cytometry is performed with a FACScan flow cytometer (Beckton Dickinson, Mountain View, Calif.) using CellQuest software. Data are collected for 20000 cells. The average FSC of spleen cells is 100 in all cases. Stained cells (FSC>100, FL2>100) are gated and the proportion of these cells staining intensely for PE (PE>1000) is calculated. Results are expressed as the % intensely stained cells after subtraction of background fluorescence for unstained cells incubated with rat IgG (% PE>1000).

Lung Histology

Immediately after treatment, the lungs of 2-4 mice from each treatment group are fixed in 10% (v/v) neutral buffered formalin and sent for independent analysis. Lungs are embedded in paraffin, sectioned and stained with hematoxylin and eosin. The slides are evaluated for peribronchial inflammation and scores are assigned on a scale of 0-4, corresponding to a score of normal to severe, respectively [Sur S, Wild J S, Choudhury B K et al. Long term prevention of allergic lung inflammation in a mouse model of asthma by CpG oligodeoxynucleotides. J Immunol 1999; 162:6284-93.].

Whole Body Plethysmography.

In this study, airway hyperresponsiveness is measured using unrestrained whole body plethysmography [Hamelmann E, Schwarze J, Takeda K et al. Noninvasive measurement of airway responsiveness in allergic mice using barometric plethysmography. Am J Respir Crit. Care Med 1997; 156:766-75] with a four-chamber system (Buxco, Sharon, Conn.). Mice are first challenged with intranasal antigen and allowed to recover for 2 hours before being placed into the chambers and their breathing monitored for 10 mins. When acclimatized, their baseline response is measured for 5 mins. The mice are then subjected to 1 min of aerosolised PBS, followed by progressively increasing doses of methacholine (5, 10, 20, 30, 40 mg/ml PBS). Responses are recorded for 5 mins in every case with a short interval between to allow return to baseline Penh. Each group contained 4-8 mice. Results are presented as the average % elevation in Penh over baseline after a challenge of methacholine.

Statistics

Results are the average for 4-8 mice/group and error bars are ±SEM. Significance is determined by Student's 2-tailed t-test. Significance is accepted for $P<0.05$.

Example 2 Results

Results on treatment of sensitised mice with recombinant SP-D are shown in FIGS. 2, 3, 4 and 5.

Figure 2A:
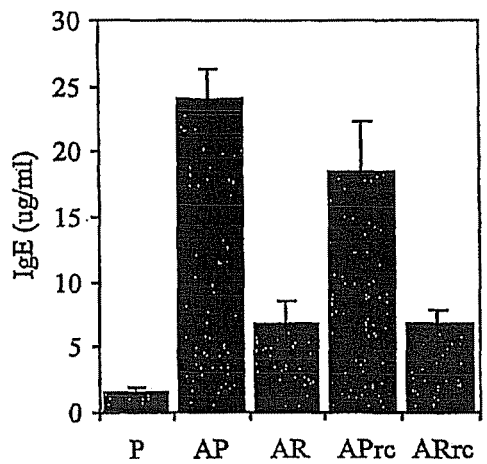
Figure 2B:
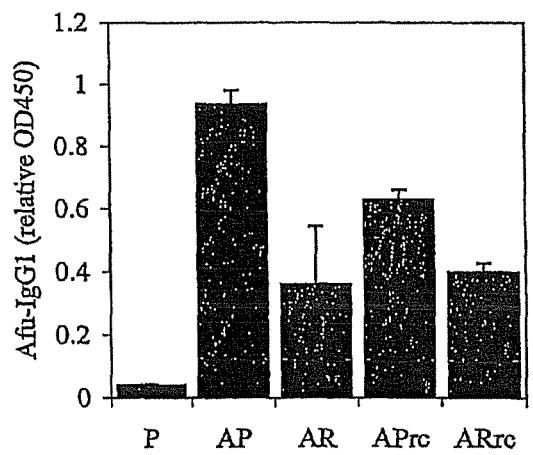
Figure 3:
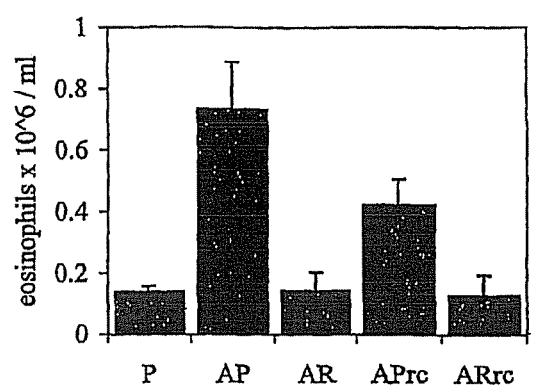

Serum IgE, Afu-specific IgG1 and peripheral blood eosinophilia are reduced by rSPD(n/CRD) in a different genetic background To determine if treatment with rSPD(n/CRD) is effective in a different genetic background an ABPA model is established in C57BL/6 mice and to determine if rSPD(n/CRD) could modulate allergic hypersensitivity during allergen challenge the sensitised mice are first challenged with 10 µg Afu 1 wcf and treated 1 hour later. Serum IgE measured 3 days after treatment with 5 daily doses of 10 µg rSPD(n/CRD), given intranassaly to allergen challenged mice is significantly reduced ($P<0.001$) and this reduction is maintained after re-challenge with 3 daily doses of 10 µg Afu 1 wcf given the following week (FIG. 2A). A similar significant reduction is also measured in Afu-specific IgG1 (FIG. 2B) and peripheral blood eosinophilia measured alter treatment of allergen challenged mice and re-challenge with allergen alone the following week (FIG. 3).

Treatment with rSPD(n/CRD) Results in Elevation in IL-12 and IFN-γ and a Reduction in IL-4

Figure 4A:
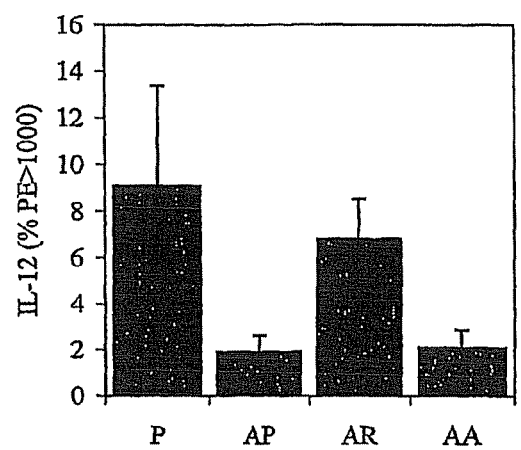
Figure 4B:
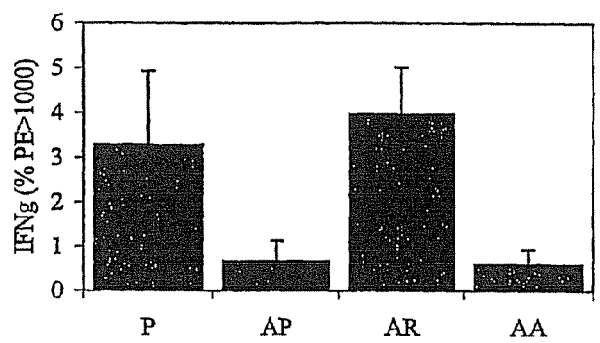
Figure 4C:
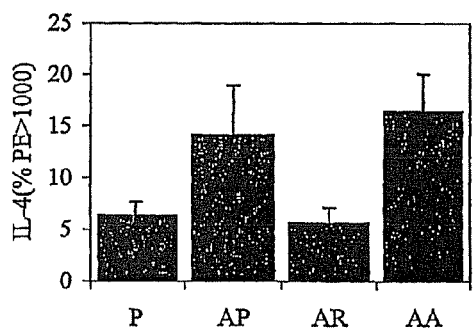

The reduction in IgE and peripheral blood eosinophilia suggests a systemic modulation at the cytokine level and these cytokines are measured by intracellular staining. IL-12 (FIG. 4A) measured in the spleen, 1 day alter treatment for 2 days with 10 µg rSPD(n/CRD), given intranasally to allergen challenged mice is significantly reduced ($P<0.05$) as is IFN-γ (FIG. 4B). Measurement of IL-4 showed a decrease to the level measured in non-sensitised mice (FIG. 4C). The same treatment with rhSP-A (recombinant human surfactant protein A, SP-A) did not produce these effects. Treatment with rSPD(n/CRD) results in reduced airway hyperresponsiveness.

Figure 5A:
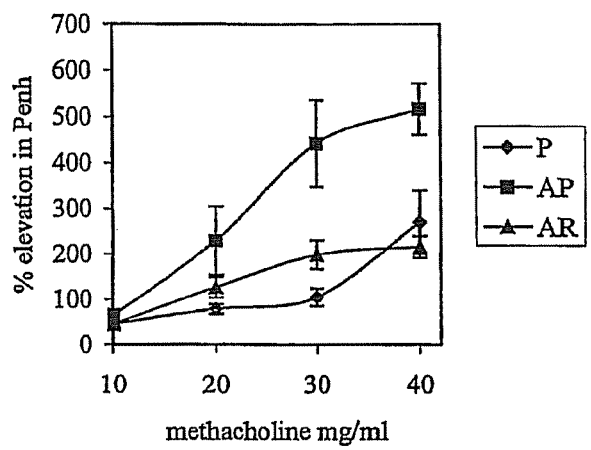
Figure 5B:
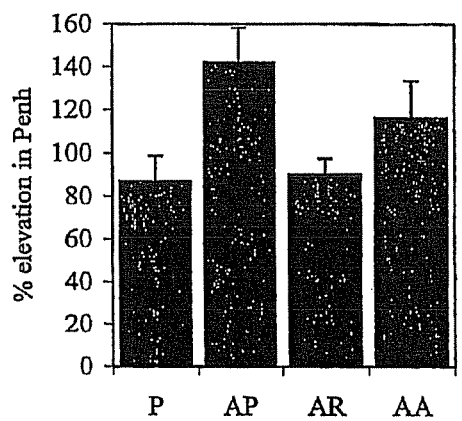

Mice treated with 4 daily doses of 10 µg rSPD(n/CRD) given 1-2 hours after allergen challenge showed a significant reduction ($P<0.05$) in airway hyperresponsiveness on re-challenge with allergen 3 days after completion of treatment (day 7) in all methacholine doses tested (FIG. 5A). Mice treated with 10 µg rhSP-A (recombinant human surfactant protein A) in the same way did not show a significant reduction in AHR (FIG. 5B).

Treatment with rSPD(n/CRD) Results in Reduced Lung Inflammation

Of the sensitised mice in this study 4 of the 6 PBS treated mice had a score of 2+ and of the 5 in the rSPD(n/CRD) treatment group 4 had a score of 1. The score for non-sensitised mice is 0. Lung sections illustrate the reduction in cellular infiltration into the lungs (FIG. 6).

Endogenous Mouse SP-D and SP-A.

Endogenous levels of SP-D measured in the BAL of allergic mice are elevated 6 fold from a level of 0.25±0.015 µg/ml in BAL from normal mice to 1.4±0.15 µg/ml, while no difference is found for the level of endogenous SP-A which is measured at 1.3±0.1 µg/ml in normal, sensitised and treated mice BAL. Treatment with 5 daily doses of 10 µg rSPD(n/CRD) did not produce any change in the level of endogenous SP-D or SP-A levels.

Example 3

Modulation of Allergic Hypersentivity in a Murine Model of Allergic Hypersensitivity to House Dust Mite (*Dermatophagoides pteronyssinus*)

Derp/IL-2/Lung

Figure 7A:
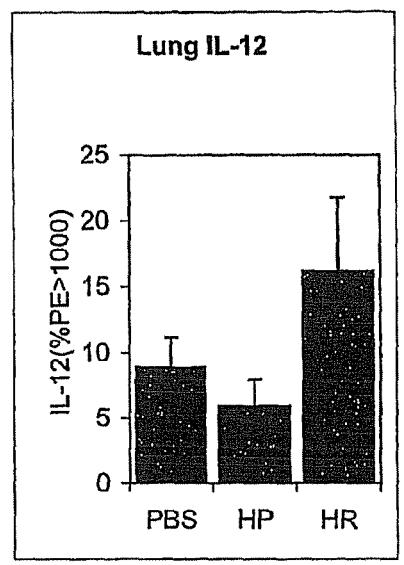

FIG. 7A shows that intranasal treatment with rSP-D (N/CRD) results in an enhancement in the IL-12 response to allergen challenge in the lungs of Der p allergic mice An analysis of IL-12 in the lung homogenates of Der p sensitised mice after treatment measured by intracellular cytokine staining followed by FACS analysis for the percentage of highly stained cells (PE>1000) positive for IL-12. PBS=non-sensitised mice treated with PBS. HP=sensitised mice treated with PBS. HR=sensitised mice treated with 10 µg rSP-D (N/CRD). Sensitised mice were first challenged with 50 AU of Der p allergen extract given intranasally. Treatment was by intranasal instillation of 10 µg rSP-D (N/CRD) given shortly after challenge. Challenge and treatment were repeated on 4 consecutive days. Mice were re-challenged with Der p alone 4 days after treatment and sacrificed the following day.

Derp/IL-2/Spleen

Figure 7B:
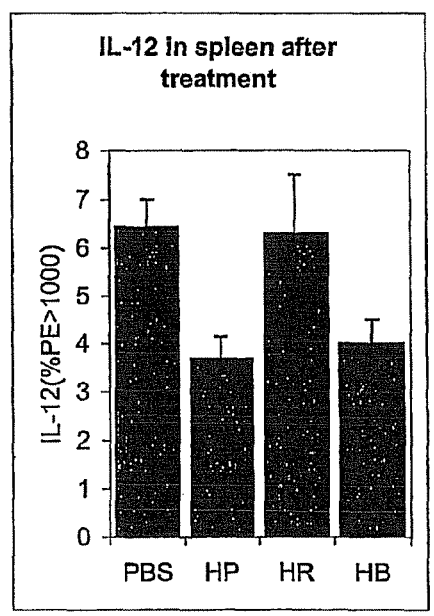

FIG. 7B shows evidence that intranasal treatment with rSP-D (N/CRD) results in an enhancement in the IL-12 response to allergen challenge in the spleen of Der p allergic mice.

An analysis of IL-12 in the spleen homogenates of Der p sensitised mice after treatment measured by intracellular cytokine staining followed by FACS analysis for the percentage of highly stained cells (PE>1000) positive for IL-12. PBS=non-sensitised mice treated with PBS. HP=sensitised mice treated with PBS. HR=sensitised mice treated with 10 µg rSP-D (N/CRD). HB=sensitised mice treated with 10 µg BSA. Sensitised mice were first challenged with 50 AU of Der p allergen extract given intranasally. Treatment was by intranasal instillation of 10 µg rSP-D (N/CRD) given shortly after challenge. Challenge and treatment were repeated on 4 consecutive days. Mice were re-challenged with Der p alone 4 days after treatment and sacrificed the following day. (n=4-8/group. 1.7× elevation.).

Derp/INF-α/Spleen

Figure 7C:
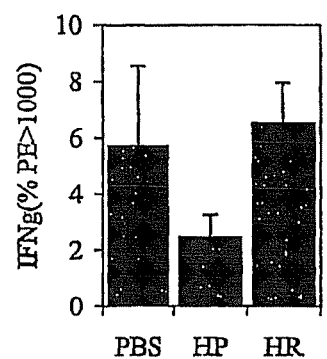

FIG. 7C shows evidence that intranasal treatment with rSP-D (N/CRD) results in an enhancement in the IFN-γ response to allergen challenge in the spleens of Der p allergic mice.

An analysis of IFN-γ in the spleen homogenates of Derp sensitised mice after treatment measured by intracellular cytokine staining followed by FACS analysis for the percentage of highly stained cells (PE>1000) positive for IFN-γ. PBS non-sensitised mice treated with PBS. HP=sensitised mice treated with PBS. HR=sensitised mice treated with 10 µg rSP-D (N/CRD). Sensitised mice were first challenged with 50 AU of Der p allergen extract given intranasally. Treatment was by intranasal instillation of 10 µg rSP-D (N/CRD) given shortly after challenge. Challenge and treatment were repeated on 4 consecutive days. Mice were re-challenged with Der p alone 4 days after treatment and sacrificed the following day. (n=4-8/group. P<0.05. 2.7× elevation).

Derp/TNF-α/Spleen

Figure 7D:
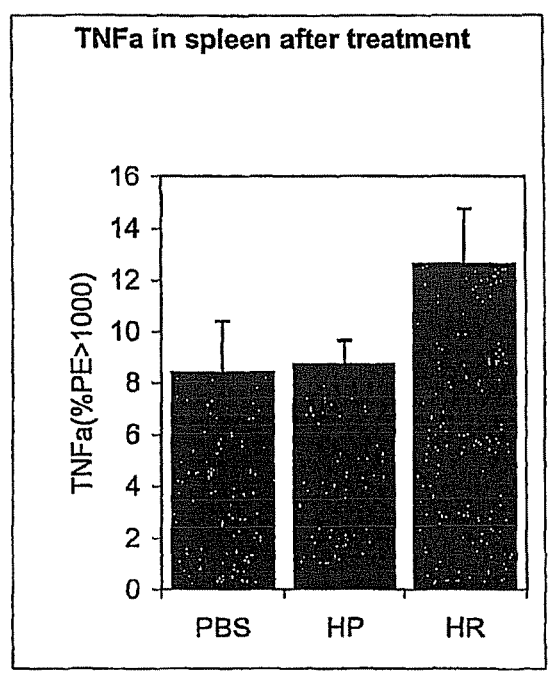

FIG. 7D shows evidence that intranasal treatment with rSP-D (N/CRD) results in an enhancement in the TNF-α response to allergen challenge in the spleens of Der p allergic mice.

An analysis of TNF-α in the spleen homogenates of Der p sensitised mice alter treatment measured by intracellular cytokine staining followed by FACS analysis for the percentage of highly stained cells (PE>1000) positive for TNF-α. PBS non-sensitised mice treated with PBS. HP=sensitised mice treated with PBS. HR=sensitised mice treated with 10 µg rSP-D (N/CRD). Sensitised mice were first challenged with 50 AU of Der p allergen extract given intranasally. Treatment was by intranasal instillation of 10 µg rSP-D (N/CRD) given shortly after challenge. Challenge and treatment were repeated on 4 consecutive days. Mice were re-challenged with Der p alone 4 days after treatment and sacrificed the following day. (n=4-8/group. 1.5× elevation).

Example 4

Effect of Treatment with rSPD(n/CRD) on Airway Hyperresonsiveness in a Murine Model of Allergic Hypersensitivity to House Dust Mite (*Dermatophagoides pteronyssinus*)

Allergic asthma is characterised by periods of airway hyperresonsiveness (AHR). AHR is known to alter breathing patterns including an extension of the expiration time, This change can be quantified by the measurement of enhanced expiratory pause (Penh).

In this study, airway hyperresponsiveness is measured using unrestrained whole body plethysmography with a 4 chamber system (Buxco, Sharon, Conn., USA). A constant bias flow of air is drawn through the system in order to prevent accumulation of $CO_2$. As the mice breathe in the mouse chamber, pressure fluctuations are measured by transducers and compared to a reference chamber. These fluctuations are produced by changes in thoracic volume during the breathing cycle. Bronchoconstriction produces differences in the shape of the pressure excursions and is most pronounced during expiration. These shape changes can be quantified by the algorithm for enhanced pause (Penth), which represents a difficulty in expiration and is a characteristic of breathing in asthmatics.

$$Penh = \frac{Te - Tr}{Tr} \times \frac{PEP}{PIP}$$

Te is the expiratory time, Tr is the relaxation time, PEP is the peak expiratory pressure and PIP is the peak inspiratory pressure.

AHR is provoked by exposing the mice to nebulised methacholine, in situ. Methacholine (Acetyl-β-methylcholine chloride) is a metabolically stable analogue of the neurotransmitter acetylcholine and causes contraction of smooth muscle resulting in provoked bronchoconstriction. The provoked AER of asthmatic mice is measured by an increase in Penh relative to normal mice.

Methods

Sensitisation. Female C57BL/6 mice are sensitised by 4 weekly i.p. injections of standerdised Der p extract (Greer Labs., USA) with alum.

Induction of airway inflammation and treatment. Sensitised mice are given 50 allergy units of Der p extract in PBS, intra nasally (i.n), preceded by i.n. administration of PBS or 10 μg rSPD(n/CRD), referred to as sequential co-administration, on 4 successive days. Animals are allowed to recover for at least 30 mins before the second i.n. administration.

Whole body plethysmography. Mice re placed into the four chambers and their breathing monitored for 10 mins. When acclimatised, their baseline response is measured for 5 mins. Next, they are subjected to 1 mm of aerosolised PBS, followed by progressively increasing doses of methacholine. Responses are recorded for 5 mins in every case with a short interval between to allow return to baseline.

Statistics. Each group contains 4-8 mice. Penh is expressed as the average % increase over the baseline value for the mice in each group. Error bars are ±SEM. Significance is determiner by paired t-tests.

Example 4 Results

Figure 8A:
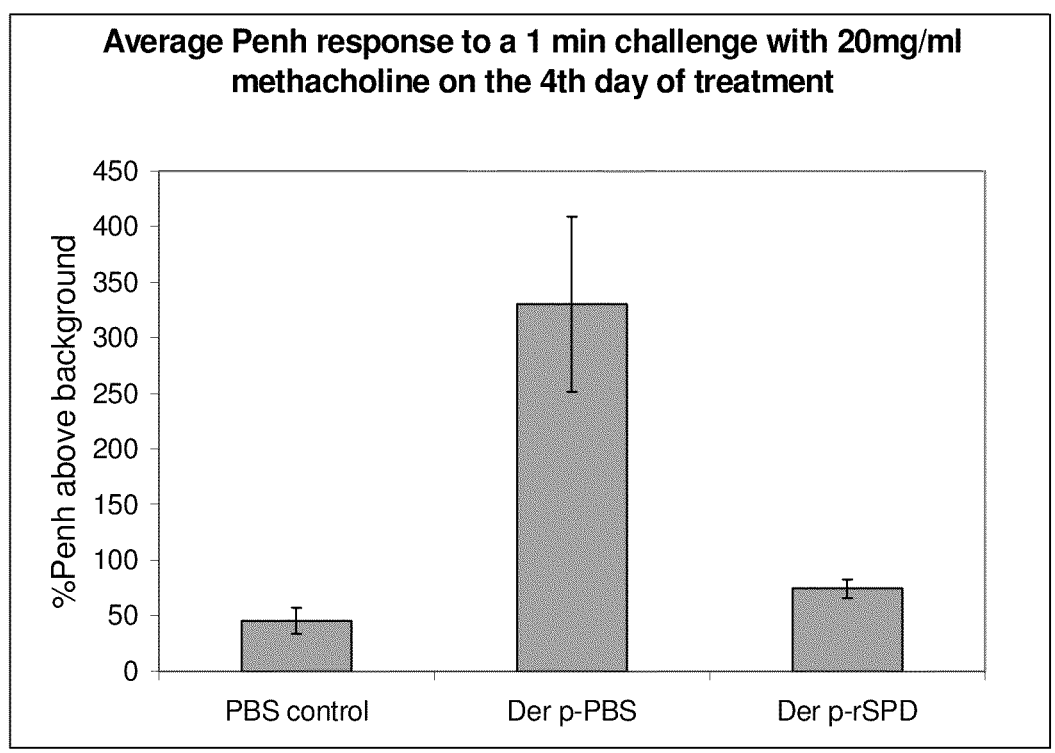
Figure 8B:
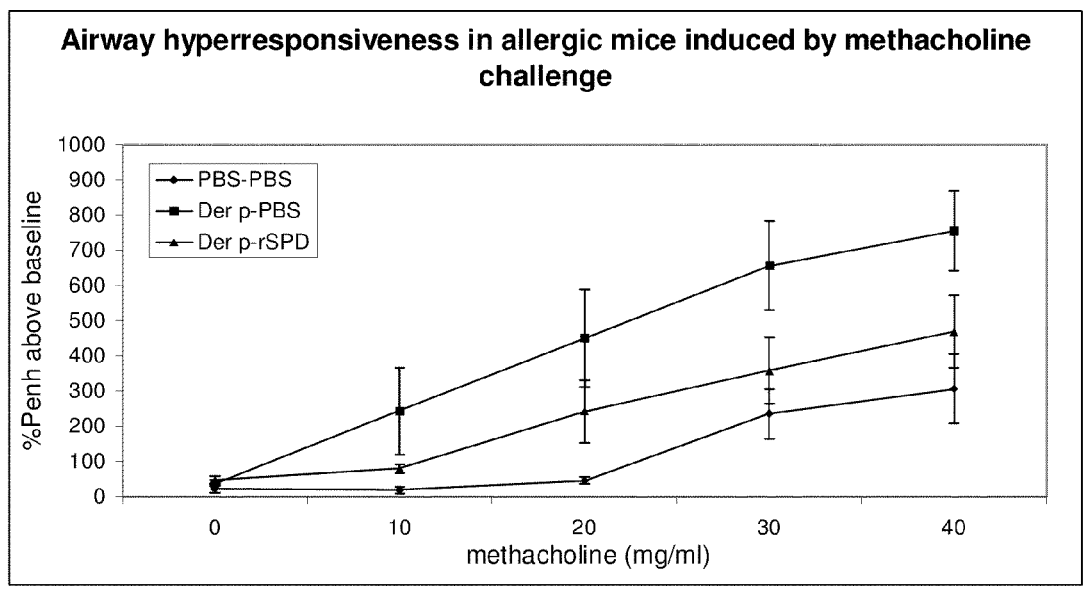

Treatment with rSPD(n/CRD) produces a significant decrease (p<0.001) in AHR as measured by the Penh response in whole body plethysmography, at the end of the treatment period (FIG. 8A; 20 mg/ml methacholine). This significant decrease was maintained when mice are re-challenged with allergen 4 days after treatment (p<0.002) as shown in FIG. 8B (methacholine dose response with re-challenge).

This study on a mice model of house dust mite allergy shows for the first time that intranasal administration of rSPD (n/CRD) significantly reduces airway hyperresponsiveness, which is a major feature of asthma. It provides evidence for the usefulness of rSPD(n/CRD) in treating the symptoms of reparatory allergic hypersensitivity reactions including allergic asthma.

It is of significance that rSPD(n/CRD) is able to reduce AHR even in the presence of sustained allergen exposure as demonstrated by its efficacy during the sequential co-administration with Der p allergen. This minors the situation encountered by seasonal allergic subjects or those constantly exposed to aeroallergens, which is a major problem in house dust mite allergy.

The most remarkable finding is that treatment with rSPD (n/CRD) has a long term effect on the underlying mechanisms as shown by the significantly reduced AHR on rechallenge with allergen alone. Thus treatment with rSPD(n/CRD) provides an effective desensitisation strategy for persons suffering from allergy and allergic asthma.

Example 5

Effect of Recombinant SP-D on Knock-Out Mice

The following three Examples describes experiments in which SP-D function is replaced in SP-D knock-out mice using recombinant human SP-D.

SP-D knock-out mice which express no SP-D, have an increased number of macrophages, many of which are abnormal in appearance. There is an excess of surfactant phospholipid in the alveolar space, indicating a chronic low grade inflammatory process in the absence of SP-D. These mice subsequently develop lung injury and fibrosis and emphysema and provide a model for the contribution made to lung injury and inflammation of SP-D deficiency (as seen in the premature infant and in smokers, patient groups with congenital and acquired SP-D deficiency, respectively). The effect on this inflammatory process of treatment with recombinantly expressed truncated fragment, human rSP-D (N/CRD), is assessed in SP-D knock-out mice.

SP-D knockout mice are produced as described in Botas, C., et al., *Altered surfactant homeostasis and alveolar type II cell morphology in mice lacking surfactant protein D*. Proc Natl Acad Sci USA, 1998. 95(20): p. 11869-74. Recombinant human SP-D is produced as described above.

Recombinant SP-D or BSA control is administered intranasally to mice from the age of 6 weeks. A total of 7 doses of 30 micrograms is given over 6 weeks, until the animals are 12 weeks old. Four mice re sacrificed after 3 weeks of treatment and underwent bronchoalveolar lavage for cell counts of alveolar macrophage number and phospholipid estimation. The experiments as described are repeated three times.

These Examples demonstrate that rSPD(n/CRD) may be used as an effective treatment for inflammatory lung disease.

Example 6

Effect of Recombinant SP-D on Knock-Out Mice as Assayed by Alveolar Macrophage Numbers The number of macrophages stained with Malachite green or crystal violet is counted in a haemocytometer and the morphology of the macrophages is assessed after cytospin.

FIG. 9 shows the number of alveolar macrophages counted in untreated mice and demonstrates that the number of cells is approximately three times those counted in wild type mice at 6 weeks and by 9 weeks and 12 weeks is almost four times wild-type. The number of macrophages is maintained in untreated knock-out mice, so that there are comparable numbers of cells harvested from the lavage at 16 weeks. However, alter treatment with rSP-D (N/CRD), the number of alveolar macrophages in SP-D knock-out BAL is reduced by approximately 50%, to levels roughly twice those seen in wild-type mice of comparable age. FIG. 9 also shows that alveolar macrophage numbers are increased in SP-D deficient compared to wild-type mice at 15 weeks.

The effect of treatment with rSP-D on the number of alveolar macrophages isolated from BAL fluid is shown. In contrast with treatment with rhSP-A, BSA or PBS, the number of macrophages is significantly decreased in rSP-D treated SP-D deficient mice at 9, 12, and 15 weeks. Macrophage numbers in rSP-D treated animals remain higher than in wild type mice at all ages.

Figure 10A:
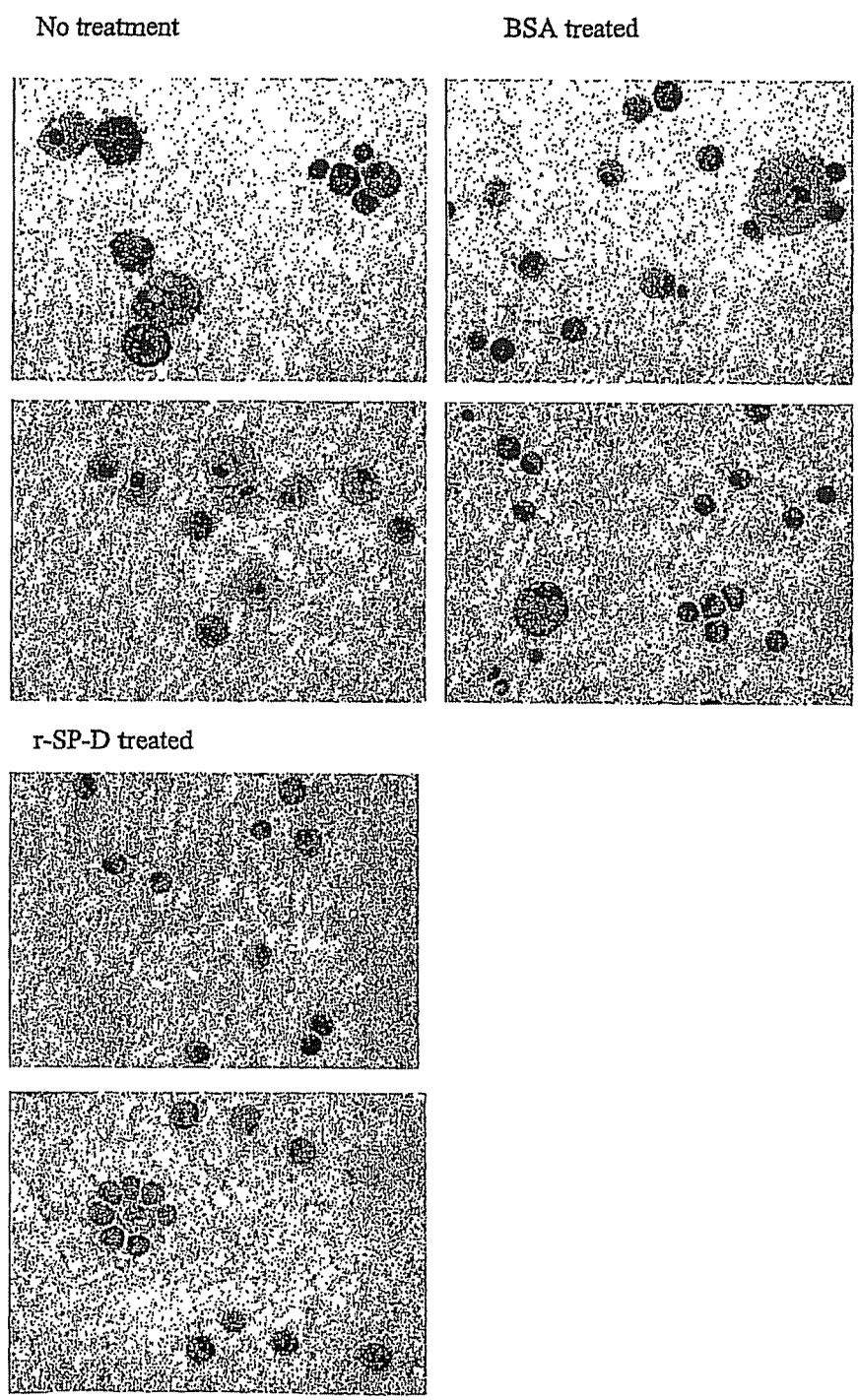

FIG. 10A shows a cytospin of cells in broncho-alveolar lavage. Cells are stained with Malachite green (upper panels) or crystal violet (lower panels). It is clear that there are fewer alveolar macrophages in rSP-D (N/CRD) treated mice and they have a more normal appearance with very few enlarged foamy macrophages visible per high power field, compared to untreated or BSA treated mice.

Figure 10B:
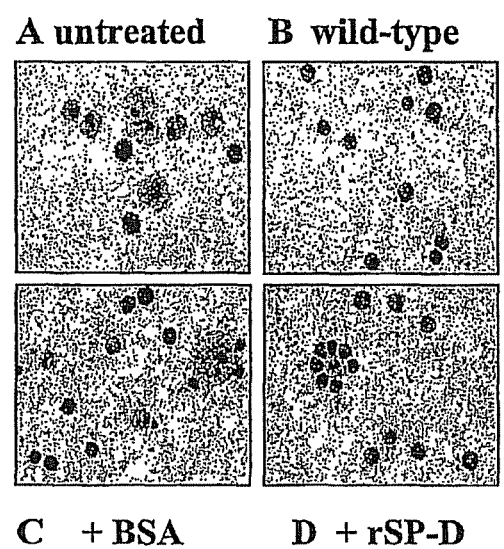

FIG. 10B shows a cytospin of cells in broncho-alveolar lavage. Cells from SP-D deficient mice are large, foamy and often multinucleated. In contrast from BSA or SP-A treated mice, alveolar macrophages from rSP-D treated mice are more frequently normal in appearance, with fewer enlarged and foamy cells. This effect is quantified by forward and side scatter flow cytometry.

Example 7

Effect of Recombinant SP-D on Knock-Out Mice as Assayed by Surfactant Phospholipid Analysis Phospholipid extraction is carried out from BAL and the phospholipid quantified by Bartlett phosphorus assay, as described in Bartlett, G. R., *Phosphorus assay in column chromatography*. J. Biol. Chem., 1959. 234: p. 466-468.

Figure 11:
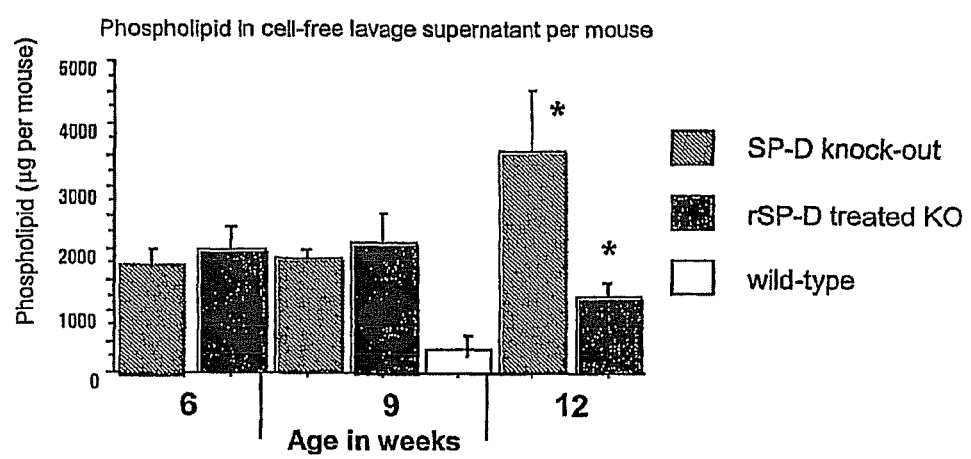

Results are shown in FIG. 11. There is no detectable difference in phospholipids assayed after 3 weeks of treatment in mice which had reached 9 weeks of age, whereas the amount of phospholipid recoverable in the lavage after 6 weeks of treatment is much reduced.

Further results relating to total phospholipid and protein measurements in cell free BAL are shown in FIG. 11B. There is a marked increase in BAL phospholipid levels in SP-D deficient mice by 6 weeks of age. There is no difference in phospholipid levels in mice receiving two weeks of treatment with rSP-D from age four weeks compared to untreated six-week old mice The same mice as used in the alveolar macrophage count experiment (FIG. 9) which are treated from age six weeks for three or six weeks are also assayed for cell free BAL phospholipid. There is no difference in BAL phospholipids after three weeks of treatment (sacrifice age nine weeks) compared to untreated nine-week old controls. However mice treated for six weeks (sacrificed for assay age 12 weeks) show a 50% reduction in excess phospholipid compared to untreated twelve week old controls ($P<0.05$). There is no significant effect of treatment on lavage total protein levels at any age.

Plasma cholesterol levels are determined in SP-D deficient mice, as shown in FIG. 17. This figure compares plasma cholesterol in mM between wild type mice and SP-D deficient mice. A paired test was conducted, with a hypothesised difference of 0. The mean difference is 0.988, the DF is 8, the T-value is −2.885 and the P-value is 0.0204.

Example 8

Effect of Recombinant SP-D on Knock-Out Mice as Assayed by Chemokine Levels

To evaluate possible mechanisms to explain the findings of reduced alveolar macrophage number, an apparently rSP-D specific effect, total RNA is isolated from rSP-D (N/CRD) treated knock-out mouse lungs and untreated controls and the levels of mRNA for a number of chemotactic factors assayed by ribonuclease protection assay using the mCK-5 multi probe template set from Phaminogen in accordance with the manufacturer's instructions. Ribonuclease protection assays are conducted on total lung RNA.

The results are normalised across samples to check for equal loading of total lung RNA using the mRNA signal for L32 and GAPDH. Each sample is loaded in duplicate in 2 concentrations, using 3 mice for each group.

Figure 12:
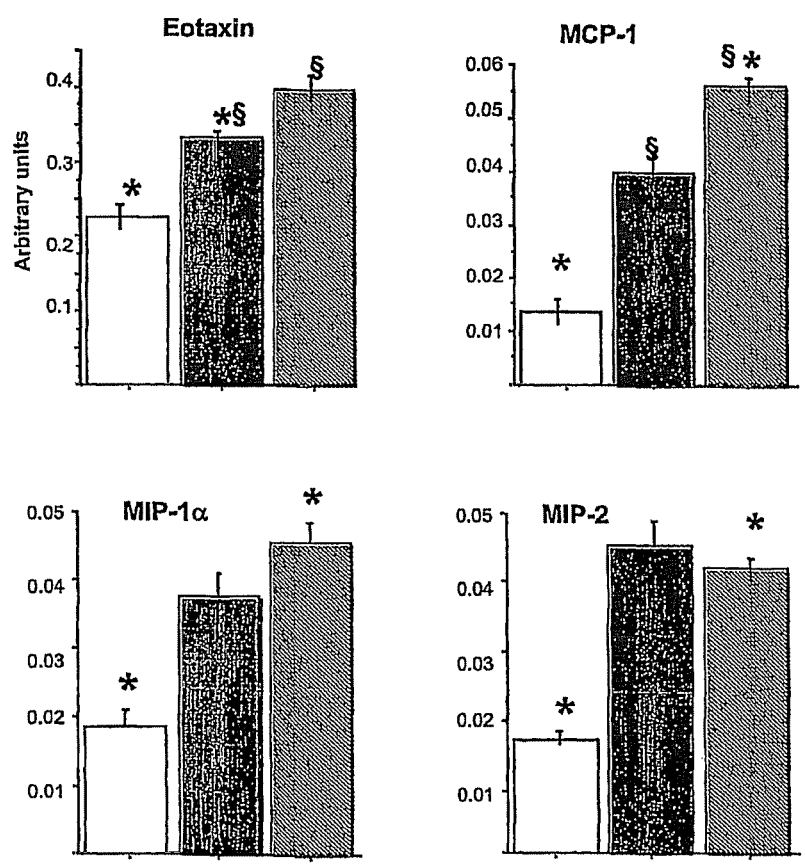

The results are shown in FIG. 12. It can be seen that there are significant differences in baseline mRNA levels between SP-D knock-out mice and wild-type mice. Specifically, levels of Eotaxin, the specific eosinophil chemotactic factor are increased by 100% in knock-out mice as compared to wild type. Furthermore, this is decreased by treatment with rSP-D (N/CRD). These observations are statistically significant at the 5% level using t-test for unpaired data. MCP-1 mRNA levels are increased 6 fold in knock-out mice as compared to wild type, and this is also decreased by treatment with rSP-D (N/CRD). A similar effect is observed on MIP-1alpha levels and on MIP 2 except that there is no significant effect of rSP-D (N/CRD) treatment on MIP-2 mRNA levels. A final observation is that TCA-3 levels are increased 4 fold in knock-out versus wildtype mice, but treatment with rSP-D (N/CRD) has no effect on the increased expression of TCA-3.

Example 9 rSP-D (N/CRD) Promotes Clearance of Apoptotic Alveolar Macrophages

The process of regulated cell death by apoptosis avoids cell necrosis and consequent release of pro-inflammatory intracellular contents. Given the excess of alveolar macrophage numbers in SP-D knock-out mice, the number of cells undergoing apoptosis in knock-out mice is measured and compared to wild type.

We hypothesised that lung injury mediated by the presence of large numbers of alveolar macrophages is due in part to impaired clearance of apoptotic alveolar macrophages with consequent triggering of an inflammatory response due to increased alveolar macrophage necrosis.

Flow Cytometry and Detection of Apoptotic and Necrotic Cells

Alveolar macrophages are isolated from mice by bronchoalveolar lavage as described above.

Figure 13A:
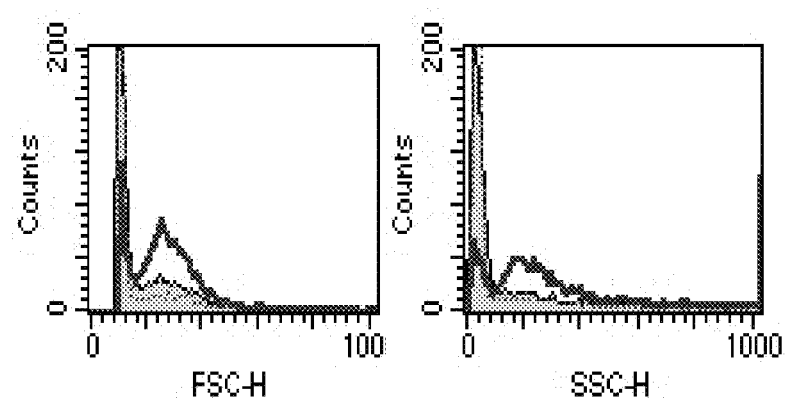
FIG. 13A shows a representative result of forward scatter (cell size) and side scatter (granularity) flow cytometry in SP-D deficient mice compared to wild-type mice.

FIG. 13A shows a representative result of forward scatter (cell size) and side scatter (granularity) flow cytometry in SP-D deficient mice compared to wild-type mice. Ten thousand cells are counted in each mouse from each group (n=6 per group). The histograms show a population of larger and more granular cells in SP-D deficient mice consistent with the cytospin appearances of enlarged foamy macrophages in SP-D deficient mice compared to those isolated from wild-type mice.

The effect of rSP-D treatment on the forward and side scatter of the cell population is shown using representative histogram overlays, and indicates a cell population with fewer abnormally large and granular alveolar macrophages, consistent with the cytospin appearances. Treatment with rhSP-A, PBS or BSA had no effect on the shape of forward and side scatter histograms.

Apoptosis and Necrosis in Alveolar Macrophages

Alveolar macrophages are isolated from mice by bronchoalveolar lavage as described above and assayed for apoptosis and necrosis by measuring binding of FITC labelled-Annexin V (which binds to surface phosphatidyl serine exposed on apoptotic cells) and Propidium Iodide (which binds necrotic cells) by FACS analysis.

Figure 13C:
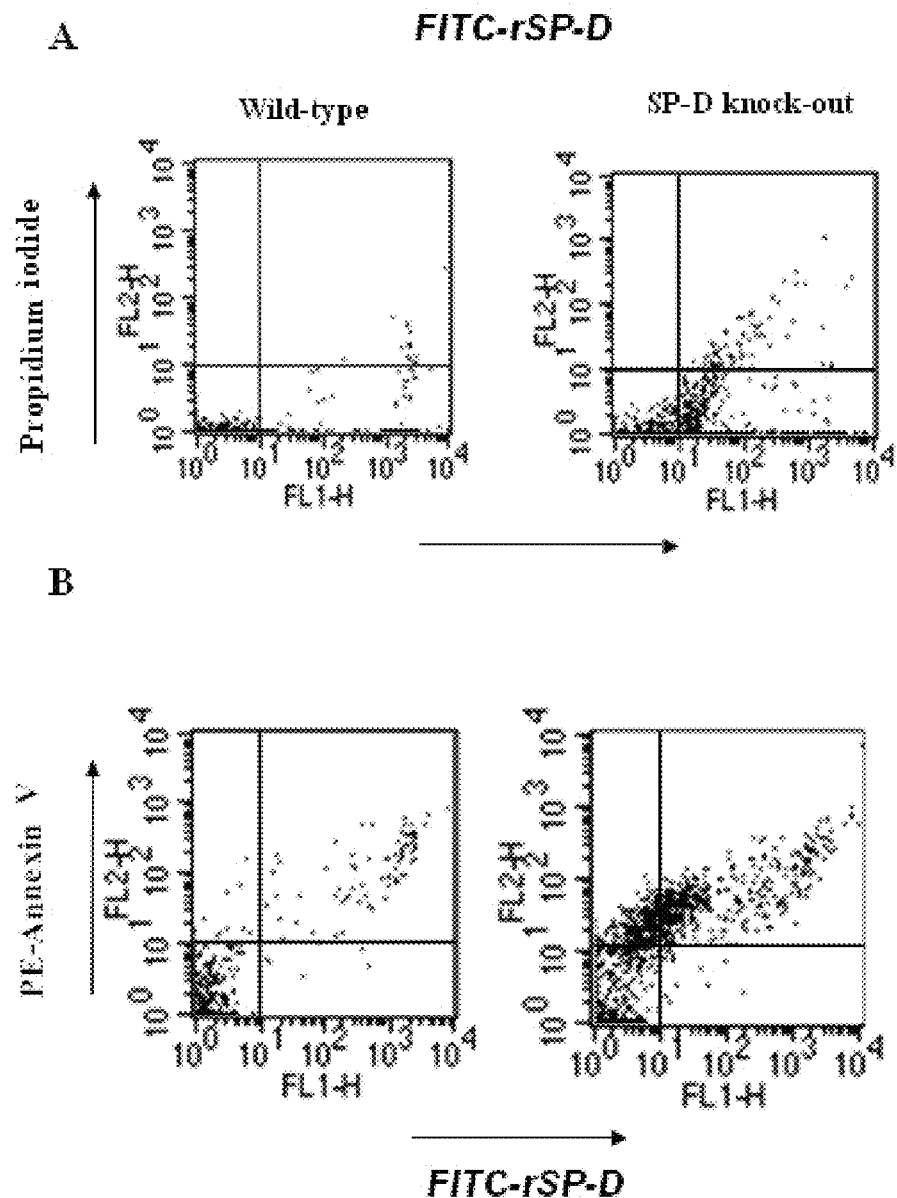
FIG. 13C shows the extent of co-labelling of FITC-labelled rSP-D with annexin V and/or PI positive cells.
Figure 13D:
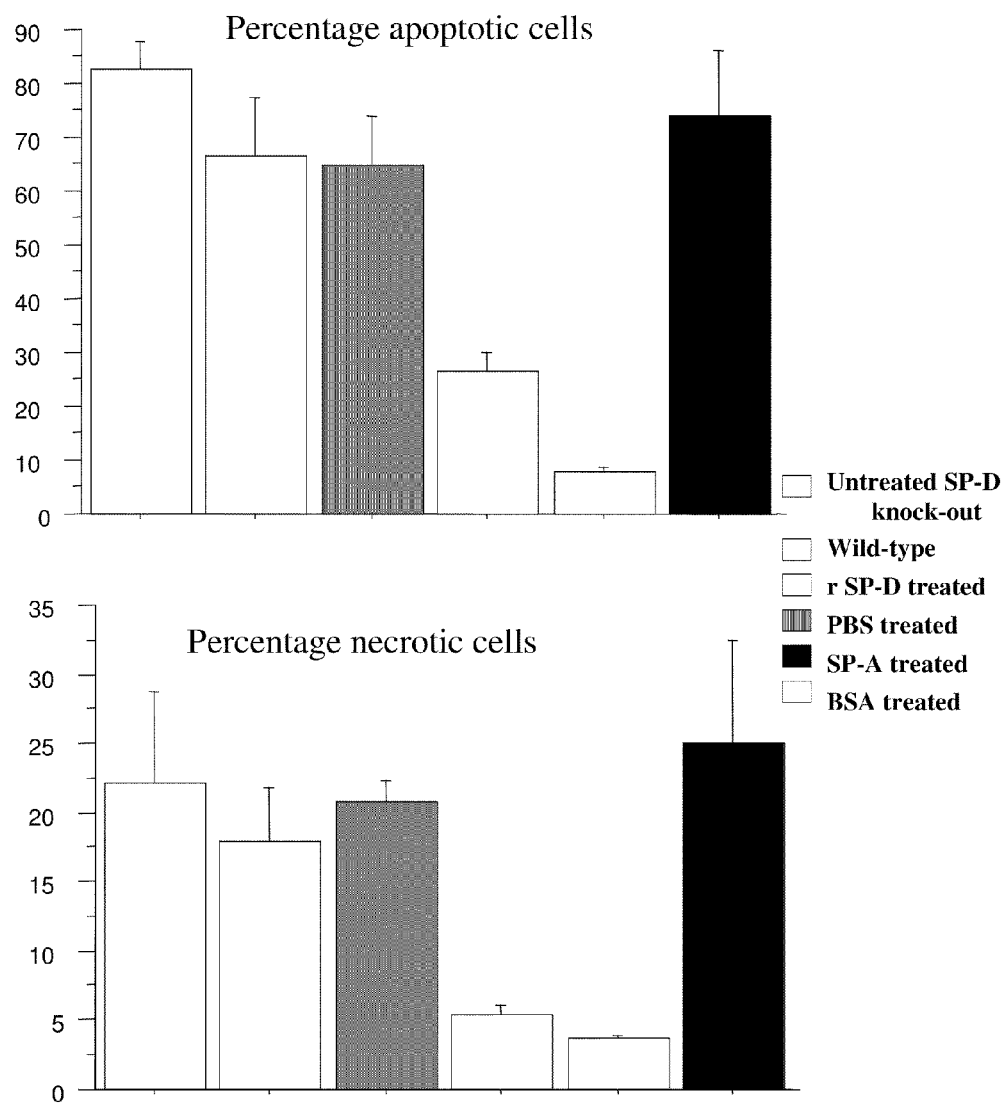
FIG. 13D is a graph showing percentage apoptotic cells (upper panel) and necrotic cells (lower panel) in bronchoalveolar lavage of untreated SP-D knock-out mice, wild-type mice, rSPD(n/CRD) treated mice, PBS treated mice, SP-A treated mice and BSA treated mice.

As shown in FIGS. 13B, 13C and 13D, there is a large difference in the number of apoptotic and necrotic macrophages in lavage from SP-D knock-out mice compared to wild-type.

Annexin V and PI Staining of Freshly Isolated Alveolar Macrophages

FIG. 13B shows the typical patterns of annexin V and PI staining of macrophages from SP-D deficient mice compared to wild-type mice. Consistently, the number of macrophages, staining with annexin V, is significantly higher in SP-D deficient mice compared to wild type, and there is a three to four fold increase in the number of cells that stained with both annexin V and PI in SP-D deficient mice. The arbitrary cut off shown in the Figure, dividing the cell population into quadrants, allows calculation of the percentages of cells staining with PI or annexin V alone in each case.

Co-labelling of Annexin V and/or PI positive Cells with FITC-Labelled rSP-D.

FIG. 13C shows the extent of co-labelling of FITC-labelled rSP-D with annexin V and/or PI positive cells. Results are representative of three experiments. The dot plots show preferential binding of FITC-rSP-D to early apoptotic (annexin V positive) and necrotic (PI positive) cells. Overall, a higher proportion of cells isolated from knock-out mice are bound by FITC-rSP-D, compared to wild-type (45+/−6% versus 15+/−1.8%). Of the small number of annexin V positive cells in wild-type mice, 80+/−6% are bound by FITC-rSP-D, compared with only 1+/−0.5% of annexin V negative cells. In knock-out mice, 55+/−4% of annexin V positive AM bound FITC-rSP-D, compared with only 3.5+/−1.7% of annexin V-negative cells. All cells which stained with PI from wild-type or knock-out mice are bound by FITC-rSP-D. Thus, there is a low level of binding of FITC-rSP-D to healthy cells (PI negative, annexin V negative) from wild-type mice and knockout mice compared to the binding to annexin V or PI positive cells. Co-incubation of freshly isolated cells with FITC-annexin V and unlabelled rSP-D did not significantly affect annexin V binding (not shown), indicating that there is no direct interaction between annexin V and rSP-D, nor any competition by rSP-D of annexin V binding to its phosphatidylserine ligand.

Analysis and Treatment with rSP-D

FIG. 13D shows that SP-D deficient mice have a ten fold increase in the proportion of apoptotic alveolar macrophages in bronchoalveolar lavage compared to wild-type mice (knock-out 74%+/−8% vs 6%+/−2% in wildtype) and a six fold increase in necrotic alveolar macrophages (25%+/−8% in knock-out versus 4+/−2% in wildtype). Intranasal replacement therapy for 3-6 weeks with r SP-D (N/CRD) increases clearance of apoptotic and necrotic alveolar macrophages from the alveolar space in SP-D deficient animals, whereas similar treatment with bovine serum albumin or surfactant protein A (SP-A) has no effect.

The effect of treatment with rSP-D on the percentages of cells staining with either PI or annexin V is also shown in the Figure.

The percentage of apoptotic macrophages are 25%+/−4% in rSP-D (N/CRD) treated mice versus 76%+/−10% in controls. Treatment with rSP-D (N/CRD) reduces the percentage of necrotic macrophages in lavage of SP-D knockout mice (around 25%) to levels comparable with wild type (5% versus 4%). The overall effect of treatment with rSP-D (N/CRD) is to decrease the absolute number of alveolar macrophages in the lung, along with levels of pro-inflammatory cytokines and excess surfactant phospholipids by 50%.

There is no significant effect of treatment with rhSP-A, BSA, or PBS on the percentage of cells staining with annexin V and/or PI. By contrast, rSP-D treatment resulted in a significant reduction in the number of annexin V and/or PI positive cells in the BAL of SP-D deficient mice, though the number of annexin V and/or PI positive cells is still significantly higher than wild-type.

Modulation of GM-CSF Levels in Bronchoalveolar Lavage

Modulation of GM-CSF levels in bronchoalveolar lavage are shown in FIG. 14. As can be seen, the concentration of GM-CSF in bronchoalveolar lavage of wild-type mice is about 50 pg/ml, compared to about 185 pg/ml in SP-D knock-out mice. Treatment of such knock-out mice with rSP-D (N/CRD) reduces the levels of GM-CSF to about 120 pg/ml. Results from flow cytometry and biochemical analyses are consistent with lung histology and cytospin examination of alveolar macrophages harvested from bronchoalveolar lavage.

Confocal Microscopy

Figure 15:
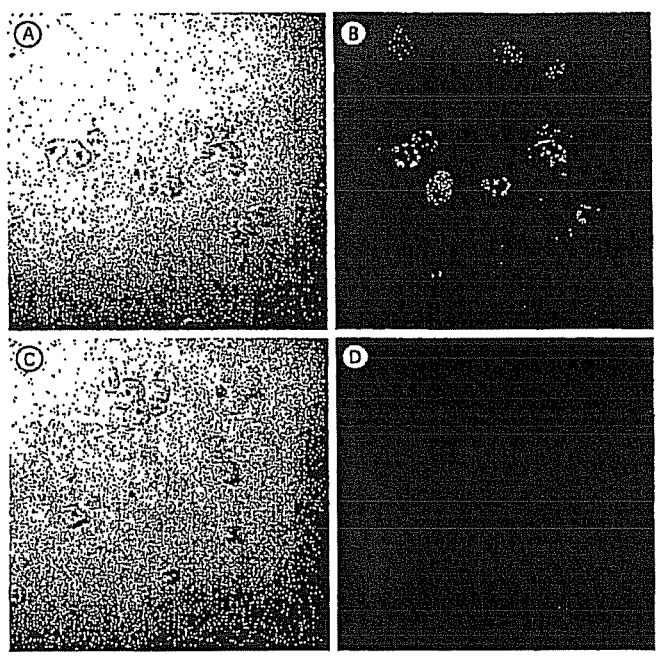
FIG. 15 shows confocal microscopy of macrophages from wild-type (panels A and B) and knock-out mice (panels C and D), stained with FITC-dUTP (green). Cells in advanced apoptosis stain green and cells in early apoptosis are identified by characteristic punctate staining of end labelled DNA fragments.

FIG. 15 shows confocal microscopy of macrophages from wild-type (panels A and B) and knock-out mice (panels C and D), stained with FITC-dUTP (green). Cells in advanced apoptosis stain green and cells in early apoptotis are identified by characteristic punctate staining of end labelled DNA fragments.

Figure 16B:
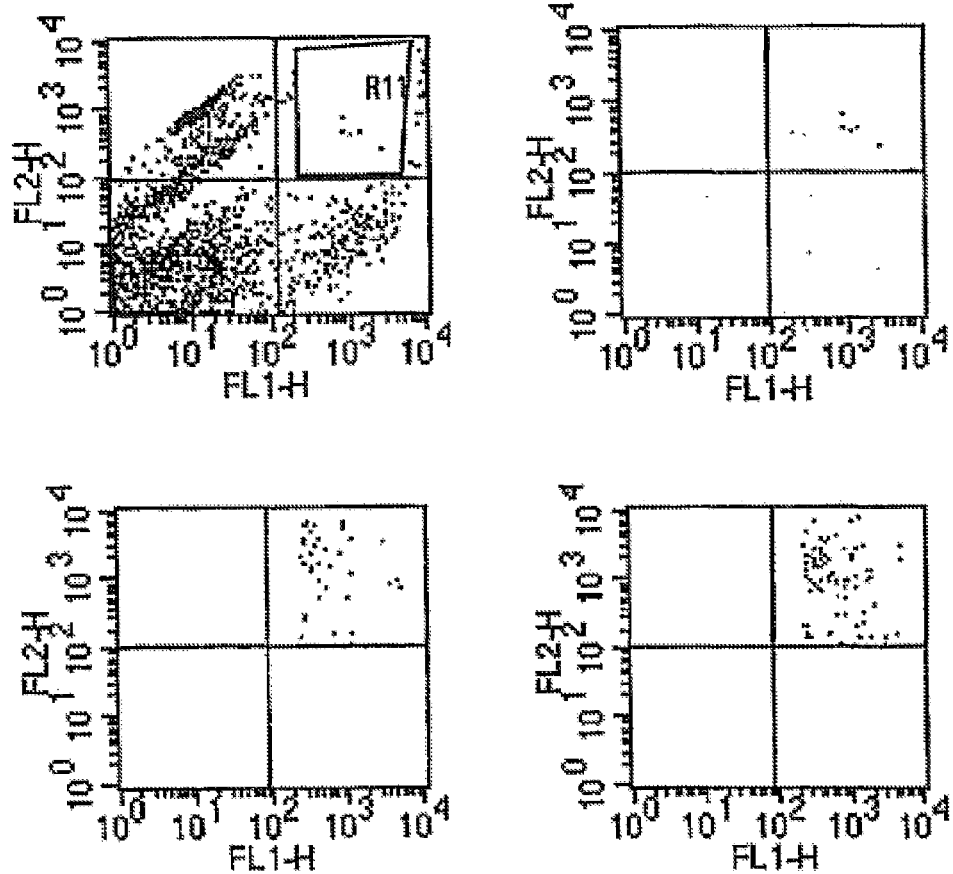

Detection of Phagocytosis of Orange Stained Necrotic and Apoptotic Macrophages by Green Stained Freshly Isolated Macrophages Cells are isolated from knock-out mice as described above and incubated with Cell Tracker™ Orange dye overnight at room temperature. Colabelling with Annexin V-FITC confirms that 80-90% of these cells are double labelled with orange dye and are Annexin V positive. Freshly isolated cells are incubated with Cell Tracker™ Green in accordance with the manufacturer' instructions. Many cells fail to stain with Cell Tracker™ Greenwhich depends on live cells (FIG. 16, lower left quadrant, panel A), and a proportion of cells were successfully labelled (FIG. 16, lower right quadrant, panel A)

Panel A shows the result of immediate mixing of orange and green cell populations. Using the gate indicated to exclude unstained cells and background double fluorescence (indicated on panel B), panels C and D show double labelling after coincubation of cells for 15 minutes at 37 degrees without SP-D (panel C) and with SP-D (panel D) at 4 mcg/ml. The number of double labelled cells is enhanced in the presence of SP-D by 80%.

These results in SP-D knock-out mice reveal a critical role for SP-D in regulating clearance of apoptotic and necrotic macrophages and indicate that rSP-D (N/CRD) based therapy provides a novel approach in a spectrum of lung disease involving alveolar macrophage mediated inflammatory processes and other diseases.

However, the shown data relating to involvement of SP-D in the regulation and clearance of apoptotic cells also have implications for abnormalities of development (e.g., abnormal post natal lung development in neonatal lung disease following premature birth), remodelling of inflamed tissues, cellular proliferation and cancer.

Example 10

Binding of SP-D and rSPD(n/CRD) (referred to as recombinant fragment SP-D, rSPD(n/CRD)) to DNA is tested in a variety of ways. In a first assay electron microscopy is used to demonstrate complexes between DNA and SP-D, and DNA and rf-SP-D. See FIG. 18. The images obtained by electron microscopy demonstrate that SP-D and rSPD(n/CRD) bind DNA effectively.

In a second assay, shown in FIG. 19, binding between rSPD(n/CRD) and the carbohydrate mannan is competed by deoxyribonucleotides, suggesting that SP-D binds to DNA via its carbohydrate binding capacity. The deoxyribonucleotides effectively compete for binding to SP-D with immobilised mannan, showing that the nucleotides are bound in solution.

In a third assay, shown in FIG. 20, alveolar macrophages isolated from the SP-D knock out mice (mainly apoptotic), were incubated with indicated concentrations of rSPD(n/CRD) followed by propidium iodide, and the red colour propidium iodide that was bound to the cell was determined by FACS analysis. In the presence of 4 and 20 μg/mL rSPD (nJCRD), 11.4 and 2.1% of the cells contained propidium iodide, respectively, compared with 16.8% in the absence of the protein. These results show that rSPD(n/CRD) binds DNA on the apoptotic cells.

To obtain evidence of the defect in the clearance of DNA in vivo, we isolated alveolar macrophages from SP-D knockout mice (SP-D$^{(-/-)}$) and compared their ability to take up DNA with that of wild type and SP-A knockout mice (SP-A$^{(-/-)}$). The data (FIG. 21) show that alveolar macrophages isolated from SP-D deficient mice were poor (4.0%) in clearing DNA compared with that of wild type (10.5%) or SP-A deficient mice (13.2). These results suggest that SP-D plays an important role in DNA clearing pathway in the lung.

REFERENCES

Platts-Mills, T. A., and M. D. Chapman. 1987. Dust mites: immunology, allergic disease, and environmental control. J Allergy Clin Immunol. 80:755-75.

Platts-Mills, T. A., B. B. Mitchell, M. D. Chapman, and P. W. Heymann. 1987. Dust mite allergy: its clinical significance. Hosp Pract (Off Ed). 22:91-3, 97-100.

Pollart, S. M., M. D. Chapman, and T. A. Platts-Mills. 1987. House dust sensitivity and environmental control. Prim Care. 14:591-603.

Arruda, L. K., B. J. Mann, and M. D. Chapman. 1992. Selective expression of a major allergen and cytotoxin, Asp f I, in *Aspergillus fumigatus*. Implications for the immunopathogenesis of *Aspergillus*-related diseases. J. Immunol. 149:3354-9.

Cai, G. Z., G. L. Griffin, R. M. Senior, W. J. Longmore, and M. A. Moxley. 1999. Recombinant SP-D carbohydrate recognition domain is a chemoattractant for human neutrophils. Am J. Physiol. 276:L131-6.

Hickling, T. P., H. Bright K. Wing, D. Gower, S. L. Martin, R B. Sim, and R Maihotra. 1999. A recombinant trimeric surfactant protein D carbohydrate recognition domain inhibits respiratory syncytial virus infection in vitro and in vivo. Eur J. Immunol. 29:3478-84.

Kishore, U., L. E. A. Leigh, P. Eggleton, P. Strong, M. V. Perdikoulis, A. C. Wiffis, and K. B. Reid. 1998. Functional characterization of a recombinant form of the C-terminal, globular head region of the B-chain of human serum complement protein, Clq. Biochem J. 333:27-32.

Madan, T., U. Kishore, A. Shah, P. Eggleton, P. Strong, 3. Y. Wang, S. S. Aggrawal, P. U. Sarma, and K. B. Reid. 1997. Lung surfactant proteins A and D can inhibit specific IgE binding to the allergens of *Aspergillus fumigatus* and block allergen-induced histamine release from human basophils. Clin Exp Immunol. 110:241-9.

Madan, T., U. Kishore, M. Singh, P. Strong, H. Clark, B. M. Hussain, K. B. Reid, and P. U. Sarma. 2001. Surfactant proteins A and D protect mice against pulmonary hypersensitivity induced by *Aspergillus fumigatus* antigens and allergens. J Clin Invest. 107:467-75.

Madan, T., U. Kishore, M. Singh, P. Strong, E. M. Hussain, K. B. Reid, and P. U. Sarnia. 2001. Protective role of lung surfactant protein d in a murine model of invasive pulmonary aspergillosis. Infect Immun. 69:2728-3 1.

Awasthi S, Coalson J J, Yoder B A, Crouch E, King R I. Deficiencies in lung surfactant proteins A and D are associated with lung infection in very premature neonatal baboons. Am J Respir Crit. Care Med. 2001 February; 163(2):389-97.

Wert S E, Yoshida M, LeVine A M, Ikegami M, Jones T, Fisher H I, Korfhagen T R, Whitsett I A. Increased metalloproteinase activity, oxidant production, and emphysema in surfactant protein D gene-inactivated mice. Proc Natl Acad Sci USA. 2000 May 23; 97(11):5972-7.

Madan, T., et al., *Surfactant proteins A and D protect mice against pulmonary hypersensitivity induced by Aspergillus fumigatus antigens and allergens*. J Clin Invest, 2001. 107(4): p. 467-75.

The following numbered citations are referred to in the section on "Surfactant Replacement Therapy":

1. Jobe A. Surfactant treatment for respiratory distress syndrome. Respir Care 1986; 31 (6):467-476.

2. Berry D. Neonatology in the 1990's: surfactant replacement therapy becomes a reality. Clin Pediatr 1991; 30(3):167-170.

3. Avery M E, Mead I. Surface properties in relation to atelectasis and hyaline membrane disease. Am J Dis Child 1959; 97:517-523.

4. von Neergard K. Neue Auffassungen uber einen Grundbegriff der: die Retraktionskraft der Lunge, abhaiigig von der Oberflachenspannung in den Alveolen. Z Ges Exp Med 1929; 66:373.

5. Hallman M, Teramo K, Ylikorkala 0, Merritt T A. Natural surfactant substitution in respiratory distress syndrome. J Perinat Med 1987; 15:463-468.

6. Stableman M T. Acute respiratory disorders in the newborn. In: Avery 0, ed. Neonatology. Philadelphia: J B Lippincott, 1975:221-249.

7. Horbar J D, Wright B C, Onstad L. Decreasing mortality associated with the introduction of surfactant therapy: an observational study of neonates weighing 601 to 1300 grams at birth. Pediatrics 1993; 92(2):191-196.

8. Lang M I, Hall R T, Reddy N S, Kurth C G, T A Merritt. A controlled trial of human surfactant replacement therapy for severe respiratory distress syndrome in very low birth weight infants. J Pediatr 1990; 116(2):295-300.

9 Hoekstra R E, Jackson J C, Myers T F, Frantz I D 111, Stern M E, Powers W F, et al. Improved neonatal survival following multiple doses of bovine surfactant in very premature neonates at risk for respiratory distress syndrome. Pediatrics 1991; 88(1):10-18.

10. Kattwinkel I, Bloom B T, Delmore P, Davis C L, Farrell E, Friss H, et al. Prophylactic administration of calf lung surfactant extract is more effective than early treatment of respiratory distress syndrome in neonates of 29 through 32 weeks' gestation. Pediatrics 1993; 92(1):90-98.

11. Merritt T A, Hallman M, Berry C, Pohjavuori M, Edwards D K, Jaaskelainen J, et al. Randomized, placebo-controlled trial of human surfactant given at birth versus rescue administration in very low birth weight infants with lung immaturity. J Pediatr 1991; 118(4):581-594.

12. Dunn M S, Shennan A T, Zayack D, Possmayer F. Bovine surfactant replacement therapy in neonates of less than 30 weeks' gestation: a randomized controlled trial of prophylaxis versus treatment. Pediatrics 1991; 87(3):377-386.

13 Long W, Thompson T, Sundell H, Schumacher R, Volberg F, Guthrie R, et al. Effects of two rescue doses of a synthetic surfactant on mortality rate and survival without bronchopulmonary dysplasia in 700- to 1350-gram infants with respiratory distress syndrome. I Pediatr 1991; 118(4): 595-605.

14. Liechty E A, Donovan B, Purobit D, Gilhooly I, Feldman B, Noguchi A, et al. Reduction of neonatal mortality after multiple doses of bovine surfactant in low birth weight neonates with respiratory distress syndrome. Pediatrics 1991; 88(1):19-28.

15. Long W, Corbet A, Cotton R, Courtney S, Mc Guiness 0, Walter D, et al. A controlled trial of synthetic surfactant in infants weighing 1250 g or more with respiratory distress syndrome. N Engl J Med 1991; 325(24):1696-1703.

16. Fujiwara T, Konisbi M, Chida S, Okuyama K, Ogawa Y, Takecuchi Y, et al. Surfactant replacement therapy with a single postventilatory dose of a reconstituted bovine surfactant in preterm neonates with respiratory distress syndrome: final analysis of a multicenter, double-blind, randomized trial and comparison with similar trials. Pediatrics 1990; 86(5): 753-764.

17 The OSIRIS Collaborative Group. Early versus delayed neonatal administration of a synthetic surfactant—the judgement of OSIRIS. Lancet 1992; 340(8832):1363-1369.

18. Ferrara T B, Hoekstra R E, Couser R I, Gaziano E P, Calvin S E, Payne N R, et al. Survival and follow-up of infants born at 23 to 26 weeks of gestational age: effects of surfactant therapy. I Pediatr 1994; 124(1): 119-124.

19. Hallman M, Merritt T A, Jarvenpaa A-L, Boynton B, Mannino F, Gluck L, et al. Exogenous human surfactant for treatment of severe respiratory distress syndrome: a randomized prospective clinical trial. I Pediatr 1985; 106(6):963-969.

20. Berry D D, Pramanik A K, Phillips J B ifi Buchter D S, Kanarek K S, Easa D, et al. Comparison of the effect of three doses of a synthetic surfactant on the alveolar-arterial oxygen gradient in infants weighing > or =1250 grams with respiratory distress syndrome. S Pediatr 1994; 124(2):294-301.

21. Gortner L, Bartmann P, Pohlandt F, Bernsau U, Porz F, Hellwege H H, et al. Early treatment of respiratory distress syndrome with bovine surfactant in very preterm infants: a multicenter controlled clinical trial. Pediatr Pulmonol 1992; 14(1):4-9.

22. Corbet Al, Long W A, Murphy D J, Garcia-Prats I A, Lombardy L R, Wold D E. Reduced mortality in small premature infants treated at birth with a single dose of synthetic surfactant. J Paediatr Child Health 1991; 27(4):245-249.

23. Bose C, Corbet A, Bose G, Garcia-Prats I, Lombardy L, Wold D, et al. Improved outcome at 28 days of age for very low birth weight infants treated with a single dose of a synthetic surfactant. J Pediatr 1990; 117:947-953.

24. Corbet A, Bucciarelli R, Goldman S, Mammel M, Wold D, Long W, and the American Exosurf Pediatric Study Group. Decreased mortality rate among small premature infants treated at birth with a single dose of synthetic surfactant: a multicenter controlled trial. I Pediatr 1991; 118(2):277-284.

25. Merritt TA, Hahiman M, Bloom B T, Berry C, Benirschke K, Sahn D, et al. Prophylactic treatment of very premature infants with human surfactant. N Engl J Med 1986; 315(13):785-790.

26. Kendig 3W, Notter R H, Cox C, Reubens L I, Davis T M, Maniscalco W M, et al. A comparison of surfactant as immediate prophylaxis and as rescue therapy in newborns of less than 30 weeks' gestation. N Engl J Med 1991; 324(13): 865-871.

27. Bgberts I, de Winter J P, Sedin G, deKleine M I, Broberger U, van Bel F, et al. Comparison of prophylaxis and rescue treatment with Curosurf in neonates less than 30 weeks' gestation: a randomized trial. Pediatrics 1993; 92(6): 768-774.

28. Soll R F, Hoekstra R E, Fangman J J, Corbet A T, Adams 3M, James L S, et al. Multicenter trial of single-dose modified bovine surfactant extract (Survanta) for prevention of respiratory distress syndrome. Pediatrics 1990; 85(6): 1092-1102.

29. Heldt G P, Pesonen E, Merritt T A, Elias W, Sahn D L. Closure of the ductus arteriosus and mechanics of breathing in preterm infants after surfactant replacement therapy. Pediatr Res 1989; 25(3):305-310.

30. Hallman M, Merritt T A, Bry K, Berry C. Association between neonatal care practices and efficacy of exogenous human surfactant: results of a bicenter randomized trial. Pediatrics 1992; 91(3):552-560.

31. Lotze A, Knight G R, Martin G R, Bulas D I, Hull W M, O'Donnell R M, et al. Improved pulmonary outcome after exogenous surfactant therapy for respiratory failure in term infants requiring extracorporeal membrane oxygenation. J Pediatr 1993; 122(2):261-268.

32. Raju T N, Langenberg P. Pulmonary hemorrhage and exogenous surfactant therapy: a meta-analysis. J Pediatr 1993; 123(4):603-610.

33. Horbar I D, Soil R F, Sutherland 3M, Kotagal U, Philip A G S, Kessler D L, et al. A multicenter randomized, placebo-controlled trial of surfactant therapy for respiratory distress syndrome. N Eng! J Med 1989; 320(15): 959-965.

34. Horbar 3D, Wright I L, Soll R E, Fanaroff A A, Korones S B, Shankaran S, et al. A multicenter randomized trial comparing two surfactants for the treatment of neonatal respiratory distress syndrome. J Pediatr 1993; 123(5): 757-766.

35. Hazan J, Chessex P, Piedboeuf B, Bourgeois M, Bard H, Long W. Energy expenditure during synthetic surfactant replacement therapy for neonatal respiratory distress syndrome. J Pediatr 1992; 120(2, Part 2):529-533.

36. Speer C P, Harms K, Herting E, Neumann N, Curstedt T, Robertson B. Early versus late surfactant replacement therapy in severe respiratory distress syndrome. Lung 1990; 168(Suppl):870-876.

37. Khammash H, Penman M, Wojtulewicz, J, Dunn M. Surfactant therapy in full-term neonates with severe respiratory failure. Pediatrics 1993; 92(1):135-139.

38. Stevenson D, Waither F, Long W, Sell M, Paul T, Gong A, et al. Controlled trial of a single dose of synthetic surfactant at birth in premature infants weighing 500 to 699 grams. J Pediatr 1992; 120(2, Part 2):S3-S12.

39. Dunn. M S, Shennan A T, Possmayer F. Single-versus multiple-dose surfactant replacement therapy in neonates of 30 to 36 weeks' gestation with respiratory distress syndrome. Pediatrics 1990; 86(4):564-571.

40. Hellstrom-Westas L, Bell A R, Skov L, Greisen G, Svenningsen N R. Cerebroelectrical depression following surfactant treatment in preterm neonates. Pediatrics 1992; 89(4):643-647.

41. Zola E M, Gunkel I H, Chan R K, Lim M O, Knox I, Feldman B H, et al. Comparison of three dosing procedures for administration of bovine surfactant to neonates with respiratory distress syndrome. J Pediatr 1992; 122(3):453-459.

42. Annibale D I, Hulsey T C, Wallin L A, Engstrom P C. Clinical diagnosis and management of respiratory distress in preterm neonates: effect of participation in a controlled trial. Pediatrics 1992; 90(3):397-400.

43. Goldman S L, Bosque E, McCann B, Lewis K. Pulmonary mechanics in premature infants one month after treatment with synthetic surfactant. J Pediatr 1992; 120(2, Part 2):S25-S28.

44. Speer C P, Robertson B, Curstedt T, Halhiday H L, Compagnone D, Gefeller O, et al. Randomized European multicenter trial of surfactant replacement therapy for severe neonatal respiratory distress syndrome: single versus multiple doses of Curosuil Pediatrics 1992; 89(1):13-20.

45. Gunkel I H, Banks P L. Surfactant therapy and intracranial hemorrhage: review of the literature and results of new analyses. Pediatrics 1993; 92(6):775-786.

46. Zola E M, Overbach A M, Gunkel 311, Mitchell B R, Nagle B T, DeMarco N G, et al. Treatment investigational new drug experience with Survanta (beractant). Pediatrics 1993; 91(3):546-551.

47. van Houten J, Long W, Mullett M, Finer N, Derleth D, McMurray B, et al. Pulmonary hemorrhage in premature infants after treatment with synthetic surfactant: an autopsy evaluation. J Pediatr 1992; 120(2, Part 2):S40-S44. Erratum appears in J Pediatr 1992; 120(5):762.

48. Rubin B K, Ramirez O, King M. Mucus rheology and transport in neonatal respiratory distress syndrome and the effect of surfactant therapy. Chest 1992; 101(4):1080-1085.

49. Goldsmith L S, Greenspan J S, Rubenstein S D, Wolfson M R, Shaffer T H. Immediate improvement in lung volume after exogenous surfactant: alveolar recruitment versus increased distention. J Pediatr 1991; 119(3):424-428.

50. Bhutani V K, Abbasi S, Long W A, Gerdes I S. Pulmonary mechanics and energetics in preterm infants who had respiratory distress syndrome treated with synthetic surfactant. J Pediatr 1992; 120(2, Part 2):518-524.

51. Bhat R, Dziedzic K, Bhutani V K, Vidyasagar D. Effect of single dose surfactant on pulmonary function. Crit. Care Med 1990; 18(6):590-595.

52. Abbasi S, Bhutani V K, Gerdes I S. Long-term pulmonary consequences of respiratory distress syndrome in preterm infants treated with exogenous surfactant. J Pediatr 1993; 122:446-452.

53 Davis 3M, Veness-Meehan K, Notter R H, Bhutani V K, Kendig J W, Shapiro D L. Changes in pulmonary mechanics after the administration of surfactant to infants with respiratory distress syndrome. N Engl J Med 1988; 319(8):476-479.

54. Armsby D H, Belion G, Carlisle K, Rector D, Baldwin R, Stevenson D K, et al. Delayed compliance increase in infants with respiratory distress syndrome following synthetic surfactant. Pediatr Pulmonol 1992; 14(4):206-213.

55. Couser R I, Ferrara T B, Bbert I, Hoekstra R E, Fangman I I. Effects of exogenous surfactant therapy on dynamic compliance during mechanical breathing in preterm infants with hyaline membrane disease. J Pediatr 1990; 116(1):119-124.

56. Svenningsen N R, Bjorklund L, Vilstrup C, Werner 0. Lung mechanics (FRC and static pressure-volume diagram) after endotracheal surfactant instillation: preliminary observations. Biol Neonate 1992; 61(Suppl 1):44-47.

57. Pfenninger J, Aebi C, Bachmann D, Wagner B P. Lung mechanics and gas exchange in ventilated preterm infants during treatment of hyaline membrane disease with multiple doses of artificial surfactant (Exosurf). Pediatr Pulmonol 1992; 14(1): 10-15.

58. Kelly E, Bryan H, Possmayer F, Fmdova H, Bryan C. Compliance of the respiratory system in newborn infants pre- and postsurfactant replacement therapy. Pediatr Pulmonol 1993; 15(4):225-230.

59. Yuksel B, Greenough A, Gamsu H R. Respiratory function at follow-up after neonatal surfactant replacement therapy. Respir Med 1993; 87(3):217-22 1.

60. Kaapa P, Seppanen M, Kero P, Saraste M. Pulmonary hemodynamics after synthetic surfactant replacement in neonatal respiratory distress syndrome. J Pediatr 1993; 123(1): 115-119.

61. Sitler C G, Turnage C S, McFadden B E, Smith E O, Adams 3M. Pump administration of exogenous surfactant: effects on oxygenation, heart rate, and chest wall movement of premature infants. J Perinatol 1993; 13(3):197-200.

62 Centers for Disease Control. Update: Universal Precautions for prevention of transmission of human immunodeficiency virus, hepatitis B virus, and other bloodborne pathogens in health-care settings. MMWR 1988; 37:377-382, 387-388.

Each of the applications and patents mentioned in this document, and each document cited or referenced in each of the these applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method for clearing necrotic and apoptotic cells, said method comprising administering a therapeutically effective amount of a recombinant Surfactant Protein D (n/Carbohydrate Recognition Domain) (rSPD(n/CRD)) polypeptide to an individual suffering from a lung disease or lung condition, other than an allergic lung condition, in which there is a need for a reduction in necrotic and apoptotic cells in the lung, wherein the rSPD(n/CRD) polypeptide is set out in SEQ ID NO: 1.

2. The method of claim 1 wherein the patient suffers from neonatal chronic lung disease, neonatal respiratory distress syndrome, adult respiratory distress syndrome, chronic obstructive pulmonary disease (COPD), sarcoidosis, cystic fibrosis, pulmonary fibrosis, emphysema, bacterial infection of the lung, viral infection of the lung, interstitial inflammatory lung disease, chronic inflammatory lung disease or neonatal chronic inflammatory lung disease.

3. The method of claim 1 or 2, wherein reduction of necrotic and apoptotic cells is determined by annexin V and propidium iodide staining.

* * * * *